United States Patent
Kim et al.

(10) Patent No.: US 9,199,966 B2
(45) Date of Patent: *Dec. 1, 2015

(54) COMPOUND FOR AN ORGANIC PHOTOELECTRIC DEVICE, ORGANIC PHOTOELECTRIC DEVICE, AND DISPLAY DEVICE INCLUDING THE SAME

(75) Inventors: Nam-Soo Kim, Uiwang-si (KR); Myeong-Soon Kang, Uiwang-si (KR); Ho-Kuk Jung, Uiwang-si (KR); Kyu-Yeol In, Uiwang-si (KR); Eui-Su Kang, Uiwang-si (KR); Seung-Gyoung Lee, Uiwang-si (KR); Young-Sung Park, Uiwang-si (KR); Hyon-Gyu Lee, Uiwang-si (KR); Mi-Young Chae, Uiwang-si (KR)

(73) Assignee: CHEIL INDUSTRIES, INC., Gumi-si, Kyeongsangbuk-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/168,015

(22) Filed: Jun. 24, 2011

(65) Prior Publication Data

US 2011/0248257 A1  Oct. 13, 2011

Related U.S. Application Data

(63) Continuation of application No. PCT/KR2009/007199, filed on Dec. 3, 2009.

(30) Foreign Application Priority Data

Dec. 24, 2008  (KR) .......... 10-2008-0133692
Aug. 5, 2009  (KR) .......... 10-2009-0072155

(51) Int. Cl.
*H01L 51/46* (2006.01)
*C07D 401/10* (2006.01)
(Continued)

(52) U.S. Cl.
CPC ............ *C07D 401/10* (2013.01); *C07D 403/10* (2013.01); *C09B 57/00* (2013.01);
(Continued)

(58) Field of Classification Search
CPC .... C07D 401/10; C07D 403/10; C09B 57/00; C09K 11/06; C09K 2211/1044; H01L 2251/308; H01L 51/0058; H01L 51/006; H01L 51/0067; H01L 51/0072; H01L 51/0077; H01L 51/5012; H01L 51/5048; H05B 33/14; Y02E 10/549

See application file for complete search history.

(56) References Cited

U.S. PATENT DOCUMENTS 8,343,640 B2 *  1/2013  Kim et al. ............ 428/690
8,383,932 B2 *  2/2013  Jung et al. ............ 136/256
(Continued)

FOREIGN PATENT DOCUMENTS

| CN | 1643105 A | 7/2005 |
| CN | 1723258 A | 1/2006 |

(Continued)

OTHER PUBLICATIONS

Computer-generated translation for JP 2004-031004 (publication date Jan. 2004).*

(Continued)

*Primary Examiner* — Dawn L Garrett
(74) *Attorney, Agent, or Firm* — Lee & Morse, P.C.

(57) ABSTRACT

A compound for an organic photoelectric device, an organic photoelectric device, and a display device including the same, the compound being represented by the following Chemical Formula 1:

[Chemical Formula 1]

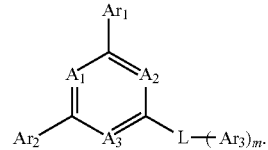

21 Claims, 3 Drawing Sheets

(51) Int. Cl.

| | |
|---|---|
| *C07D 403/10* | (2006.01) |
| *H01L 51/54* | (2006.01) |
| *C09K 11/06* | (2006.01) |
| *H01L 51/00* | (2006.01) |
| *H05B 33/14* | (2006.01) |
| *C09B 57/00* | (2006.01) |
| *H01L 51/50* | (2006.01) |

(52) U.S. Cl.
CPC ........... *C09K 11/06* (2013.01); *H01L 51/0058* (2013.01); *H01L 51/0067* (2013.01); *H01L 51/0072* (2013.01); *H05B 33/14* (2013.01); *C09K 2211/1044* (2013.01); *H01L 51/006* (2013.01); *H01L 51/0077* (2013.01); *H01L 51/5012* (2013.01); *H01L 51/5048* (2013.01); *H01L 2251/308* (2013.01); *Y02E 10/549* (2013.01)

(56) References Cited

U.S. PATENT DOCUMENTS

| | | | |
|---|---|---|---|
| 8,420,230 B2* | 4/2013 | Yang et al. | 428/690 |
| 8,470,454 B2* | 6/2013 | Kim et al. | 428/690 |
| 2004/0115476 A1 | 6/2004 | Oshiyama et al. | |
| 2005/0042475 A1* | 2/2005 | Pillow et al. | 428/690 |
| 2006/0041126 A1* | 2/2006 | Schafer et al. | 544/242 |
| 2006/0251918 A1 | 11/2006 | Iwakuma et al. | |
| 2007/0190355 A1* | 8/2007 | Ikeda et al. | 428/690 |
| 2007/0257600 A1* | 11/2007 | Matsuura et al. | 313/498 |
| 2007/0296328 A1 | 12/2007 | Matsuura et al. | |
| 2008/0145699 A1 | 6/2008 | Yabe et al. | |
| 2008/0199726 A1* | 8/2008 | Schafer et al. | 428/690 |
| 2009/0134780 A1 | 5/2009 | Ono et al. | |
| 2009/0236973 A1 | 9/2009 | Yabe et al. | |
| 2009/0281311 A1 | 11/2009 | Yamakawa et al. | |
| 2010/0038592 A1 | 2/2010 | Akino et al. | |
| 2010/0163857 A1 | 7/2010 | Kim et al. | |
| 2010/0200054 A1* | 8/2010 | Jung et al. | 136/256 |
| 2011/0215310 A1 | 9/2011 | Ono et al. | |
| 2011/0260153 A1* | 10/2011 | In et al. | 257/40 |
| 2012/0235129 A1 | 9/2012 | Iwakuma et al. | |

FOREIGN PATENT DOCUMENTS

| | | |
|---|---|---|
| CN | 1934213 A | 3/2007 |
| CN | 101248058 A | 8/2008 |
| EP | 1571193 A1 | 9/2005 |
| EP | 1718-121 A1 | 11/2006 |
| EP | 1820801 A1 | 8/2007 |
| EP | 1930329 A1 * | 6/2008 |
| EP | 2 383 323 A2 | 11/2011 |
| EP | 2 468 731 A1 | 6/2012 |
| JP | 2002-193952 | 7/2002 |
| JP | 2002-212181 A | 7/2002 |
| JP | 2003-045662 * | 2/2003 |
| JP | 2004-031004 * | 1/2004 |
| JP | 2004-178895 | 6/2004 |
| JP | 2004-253298 A | 9/2004 |
| JP | 2006-188493 | 7/2006 |
| JP | 2007-137829 | 6/2007 |
| JP | 2007-314503 | 12/2007 |
| JP | 2008-182216 A | 7/2008 |
| JP | 2012-28524 * | 2/2012 |
| KR | 10 2007-0030759 A | 3/2007 |
| KR | 10 2007-0090952 A | 9/2007 |
| WO | WO-2004/066685 A1 | 8/2004 |
| WO | WO-2005/076669 A1 | 8/2005 |
| WO | WO-2005/085387 A1 | 9/2005 |
| WO | WO 2007/029696 A1 | 3/2007 |
| WO | WO 2008/081852 A1 * | 7/2008 |
| WO | WO 2010/024572 A1 | 3/2010 |

OTHER PUBLICATIONS

Machine-generated translation for JP 2007-137829 A (publication date Jun. 2007).*
Machine-generated translation for JP 2002-193952 A (publication date Jul. 2002).*
Machine-generated translation for JP 2003-045662 A (publication date Feb. 2003).*
Cui, et al.; Diboron and Triboron Compounds Based on Linear and Star-Shaped Conjugated Ligands with 8-Hydroxyquinolate Functionality: Impact of Intermolecular Interaction and Boron Coordination on Luminescence; Journal of Organic Chemistry, 2006; pp. 6485-6496; vol. 71, No. 17; American Chemical Society, USA.
European Search Report in EP 09835188.5-2117/2376594, dated May 29, 2012 (Kim, et al.).
C.W. Tang et al. Organic Electroluminescent Diodes, Appl. Phy. Lett. 51 Sep. 21, 1987, pp. 913-915.
D.F. OBrien et al. Improved Energy Transfer in Electrophosphorescent Devices, Appl. Phy. Lett. vol. 74, No. 3, Jan. 18, 1999, pp. 442-444.
M.A. Baldo, et al. Very High-Efficiency Green Organic Light-Emitting Devices Based on Electrophosphorescence, Appl. Phy. Lett. vol. 75, No. 1, Jul. 5, 1999, pp. 4-6.
PCT Search Report in parent PCT/KR2009/007199, Date: 2009.
Taiwanese Search Report in TW 098141705, dated Nov. 29, 2012 (Kim, et al.).
Aziz, H., et al., "Degradation Phenomena in Small-Molecule Organic Light-Emitting Devices," *Chemistry of Materials*, 2004, vol. 16, No. 23, pp. 4522-4532.
Geffroy, B., et al., "Organic light-emitting diode (OLED) technology: materials, devices and display technologies," *Polymer International*, 2006, vol. 55, Iss. 6, pp. 572-582.
Chinese Search Report in CN 2009801474977, dated Apr. 7, 2013 (Kim, et al.).
Tokito, Thermal stability in oligomeric triphenylamine/tris(8-quinolinolato) aluminum electroluminescent devices, Appl. Phys. Lett. 70(15), Apr. 14, 1997, pp. 1929-1931.

* cited by examiner

COMPOUND FOR AN ORGANIC PHOTOELECTRIC DEVICE, ORGANIC PHOTOELECTRIC DEVICE, AND DISPLAY DEVICE INCLUDING THE SAME

CROSS-REFERENCE TO RELATED APPLICATION

This application is a continuation of pending International Application No. PCT/KR2009/007199, entitled "Novel Compound for Organic Photoelectric Device and Organic Photoelectric Device Including the Same," which was filed on Dec. 3, 2009, the entire contents of which are hereby incorporated by reference.

BACKGROUND

1. Field

Embodiments relate to a compound for an organic photoelectric device, an organic photoelectric device, and a display device including the same.

2. Description of the Related Art

An organic photoelectric device is a device in which a charge exchange occurs between an electrode and an organic material by using a hole or an electron.

An organic photoelectric device may be classified as follows in accordance with its driving principles. One organic photoelectric device is an electron device driven as follows: excitons are generated in an organic material layer by photons from an external light source; the excitons are separated into electrons and holes; and the electrons and holes are transferred to different electrodes from each other as a current source (voltage source).

Another organic photoelectric device is an electron device driven as follows: a voltage or a current is applied to at least two electrodes to inject holes and/or electrons into an organic material, e.g., semiconductor, positioned at an interface of the electrodes; and then the device is driven by the injected electrons and holes.

Organic photoelectric devices may include, e.g., an organic light emitting diode (OLED), an organic solar cell, an organic photo-conductor drum, an organic transistor, an organic memory device, etc., and may include, e.g., a hole injecting or transporting material, an electron injecting or transporting material, or a light emitting material.

An organic light emitting diode (OLED) has recently drawn attention due to an increase in demand for flat panel displays. In general, organic light emission refers to transformation of electrical energy to photo-energy.

The organic light emitting diode transforms electrical energy into light by applying current to an organic light emitting material. It has a structure in which a functional organic material layer is interposed between an anode and a cathode. The organic material layer may include multi-layer including different materials from each other, e.g., a hole injection layer (HIL), a hole transport layer (HTL), an emission layer, an electron transport layer (ETL), and an electron injection layer (EIL), in order to improve efficiency and stability of an organic light emitting diode.

In such an organic light emitting diode, when a voltage is applied between an anode and a cathode, holes from the anode and electrons from the cathode are injected to an organic material layer. The generated excitons generate light having certain wavelengths while shifting to a ground state.

The organic layer may have a structure in which a thin film (hole transport layer (HTL)) of a diamine derivative and a thin film of tris(8-hydroxy-quinolate)aluminum (Alq$_3$) are stacked.

A phosphorescent material emits lights by transiting the electrons from a ground state to an exited state, non-radiance transiting of a singlet exciton to a triplet exciton through intersystem crossing, and transiting a triplet exciton to a ground state to emit light.

As described above, in an organic light emitting diode, an organic material layer includes a light emitting material and a charge transport material, for example a hole injection material, a hole transport material, an electron transport material, an electron injection material, and so on.

The light emitting material is classified as blue, green, and red light emitting materials according to emitted colors, and yellow and orange light emitting materials to emit colors approaching natural colors.

When one material is used as a light emitting material, a maximum light emitting wavelength is shifted to a long wavelength or color purity decreases because of interactions between molecules, or device efficiency decreases because of a light emitting quenching effect. Therefore, a host/dopant system is included as a light emitting material in order to improve color purity and increase luminous efficiency and stability through energy transfer.

SUMMARY

Embodiments are directed to a compound for an organic photoelectric device, an organic photoelectric device, and a display device including the same.

The embodiments may be realized by providing a compound for an organic photoelectric device, the compound being represented by the following Chemical Formula 1:

[Chemical Formula 1]

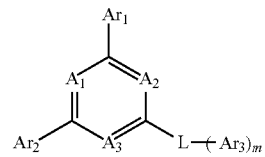

wherein in the above Chemical Formula 1, $A_1$ to $A_3$ are each independently carbon or nitrogen, provided that at least two of $A_1$ to $A_3$ are nitrogen, $Ar_1$ and $Ar_2$ are each independently a substituted or unsubstituted C6 to C30 aryl, $Ar_3$ is a substituted or unsubstituted carbazolyl, a substituted or unsubstituted C2 to C30 heteroaryl, a substituted or unsubstituted C2 to C30 arylamine, a substituted or unsubstituted C2 to C30 heteroarylamine, or a combination thereof, L is a substituted or unsubstituted phenylene, naphthalene, or anthracene, and m is an integer of 1 to 3.

$Ar_1$ and $Ar_2$ may each independently be a phenyl, a naphthyl, an anthracenyl, a phenanthrenyl, a pyrenyl, a perylenyl, a chrysenyl, or a combination thereof.

At least one of $Ar_1$ and $Ar_2$ may include a substituent, the substituent including a C1 to C30 alkyl, a C1 to C10 alkylsilyl, a C3 to C30 cycloalkyl, a C6 to C30 aryl, a C1 to C10 alkoxy, a fluoro, a trifluoroalkyl, a cyano, or a combination thereof.

$Ar_3$ may include imidazole, thiazolyl, oxazolyl, oxadiazolyl, triazolyl, pyridinyl, pyridazine, quinolinyl, isoquinolinyl, acridinyl, imidazopyridinyl, imidazopyrimidinyl, diphenyl amine, dinaphthyl amine, dibiphenyl amine, phenyl naphthyl amine, phenyl diphenyl amine, ditolyl amine, phenyl tolyl amine, carbazole, triphenyl amine, dipyridyl amine, or a combination thereof.

L may be phenylene.

The compound represented by Chemical Formula 1 may be represented by at least one of the following Chemical Formulae 2 to 10:

[Chemical Formula 2]

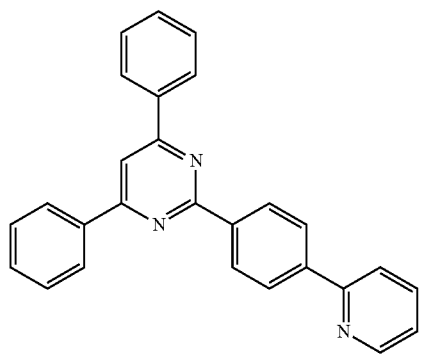

[Chemical Formula 3]

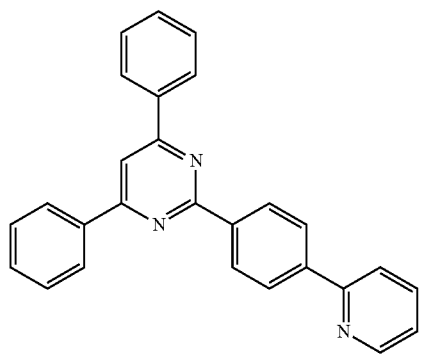

[Chemical Formula 4]

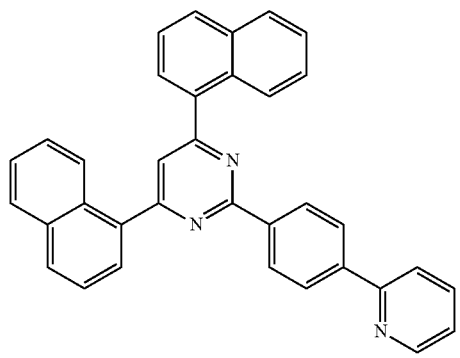

[Chemical Formula 5]

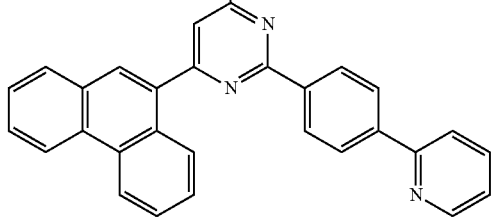

[Chemical Formula 6]

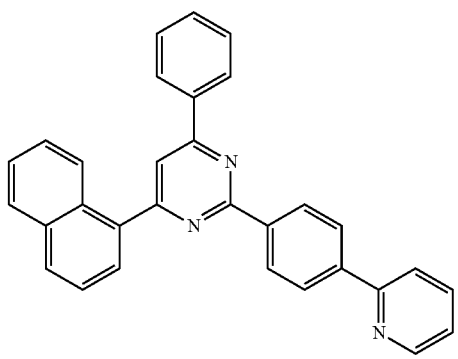

[Chemical Formula 7]

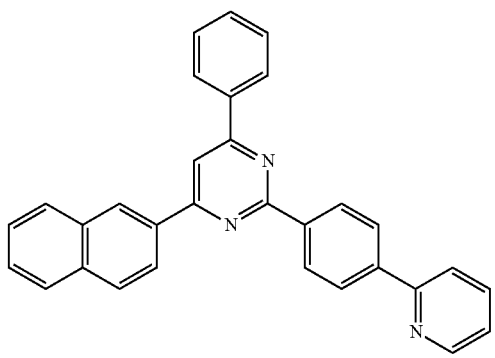

[Chemical Formula 8]

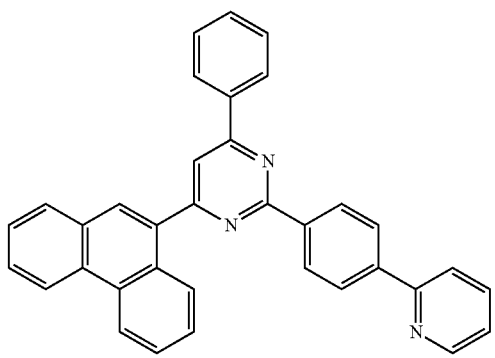

[Chemical Formula 9]
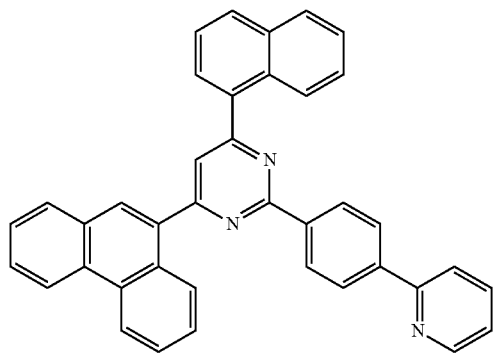
[Chemical Formula 10]
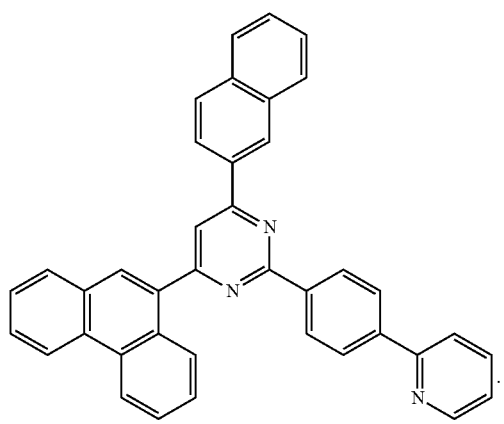
The compound represented by Chemical Formula 1 may be represented by Chemical Formula 1 is represented by at least one of the following Chemical Formulae 11 to 19:
[Chemical Formula 11]
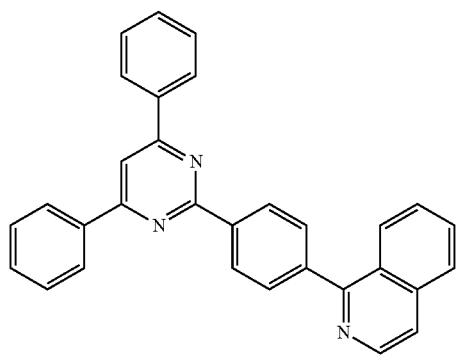
[Chemical Formula 12]
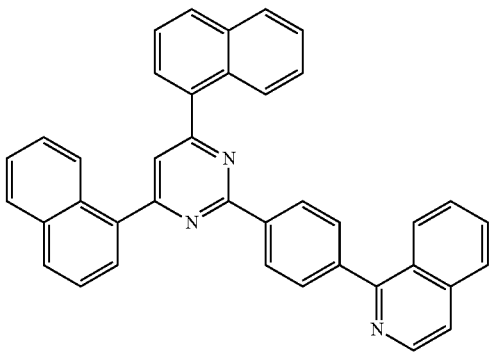
[Chemical Formula 13]
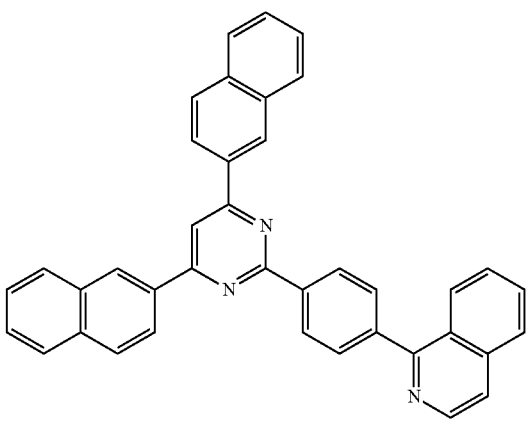
[Chemical Formula 14]
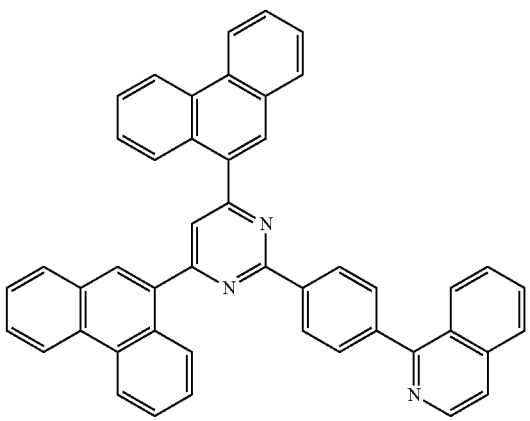
[Chemical Formula 15]
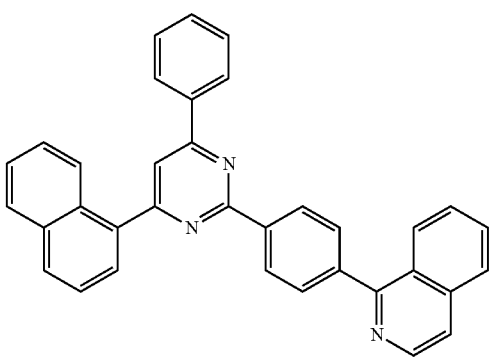

[Chemical Formula 16]
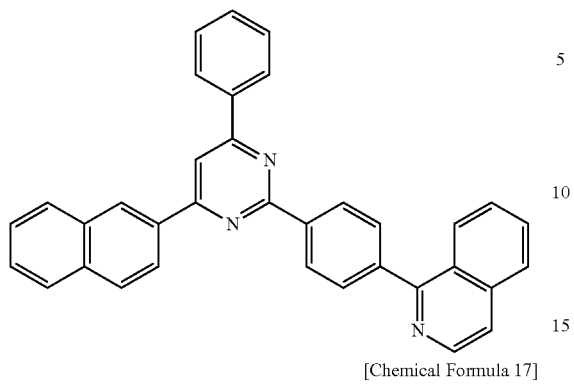
[Chemical Formula 17]
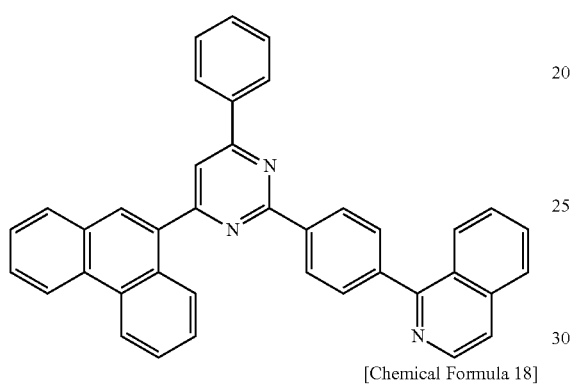
[Chemical Formula 18]
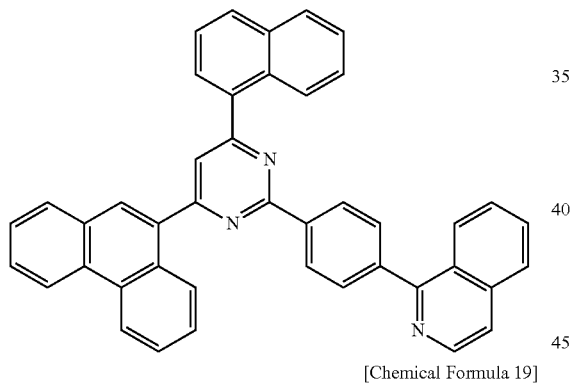
[Chemical Formula 19]
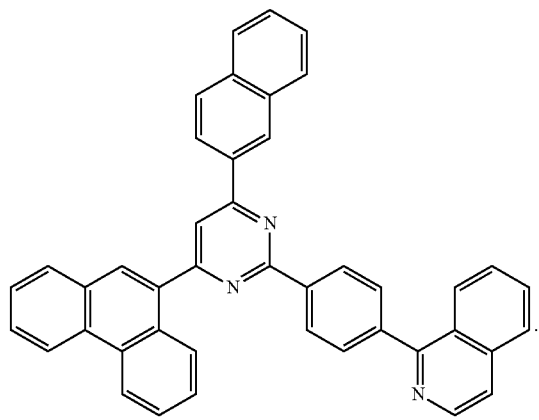
[Chemical Formula 20]
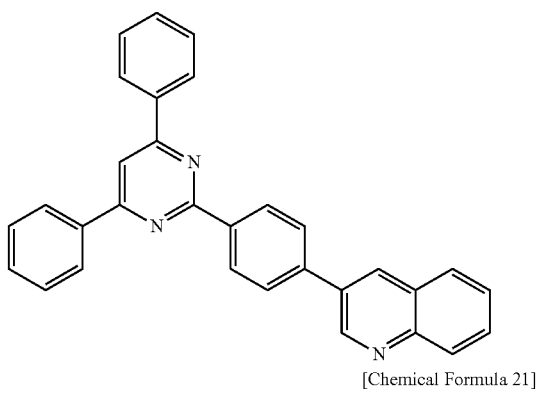
[Chemical Formula 21]
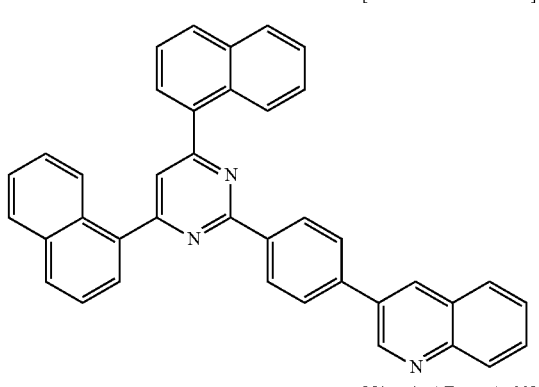
[Chemical Formula 22]
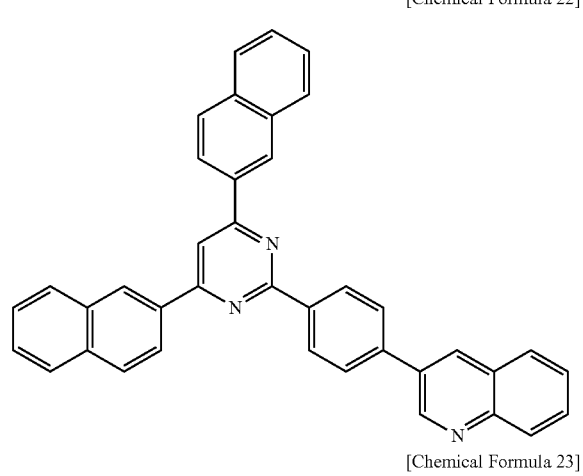
[Chemical Formula 23]
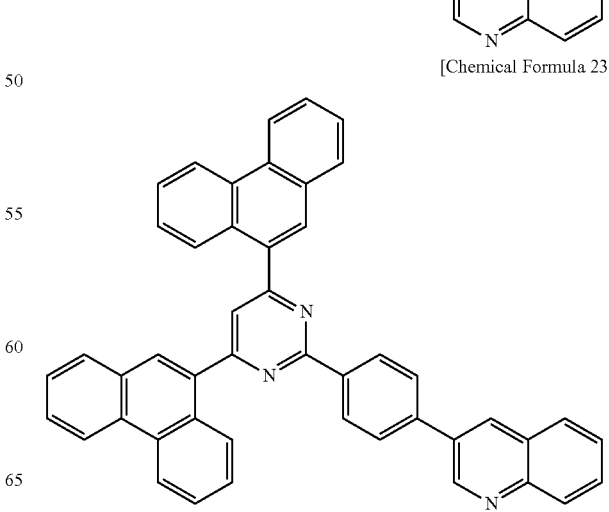
The compound represented by Chemical Formula 1 may be represented by Chemical Formula 1 is represented by at least one of the following Chemical Formulae 20 to 28:

[Chemical Formula 24]
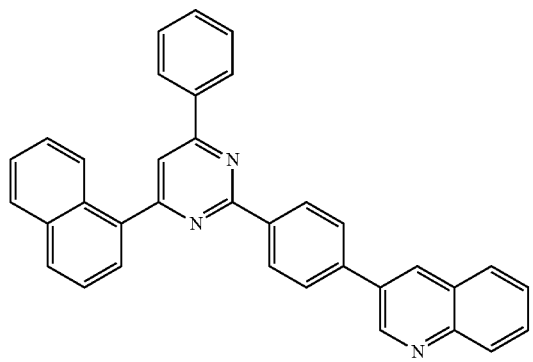
[Chemical Formula 25]
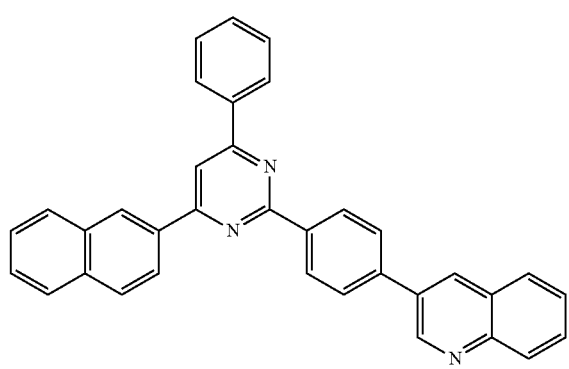
[Chemical Formula 26]
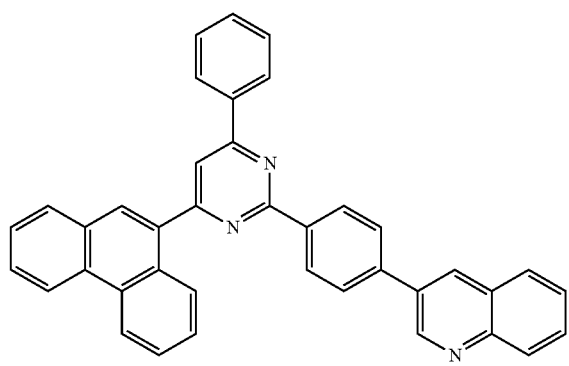
[Chemical Formula 27]
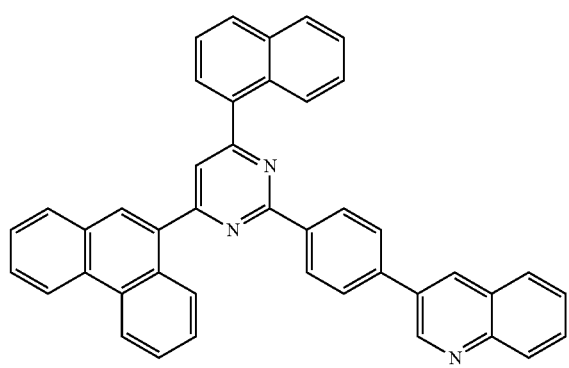
[Chemical Formula 28]
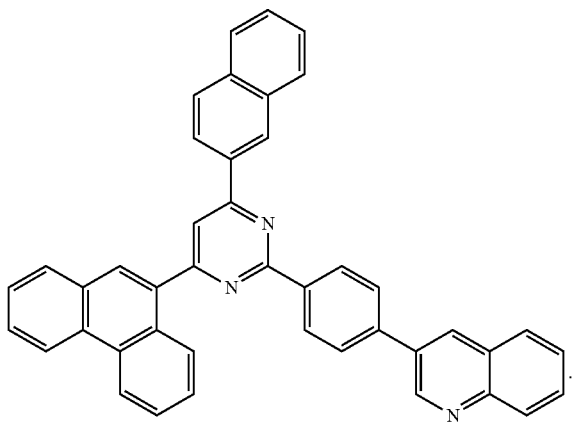
The compound represented by Chemical Formula 1 may be represented by Chemical Formula 1 is represented by at least one of the following Chemical Formulae 29 to 37:
[Chemical Formula 29]
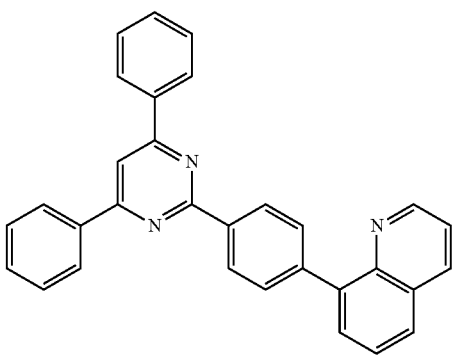
[Chemical Formula 30]
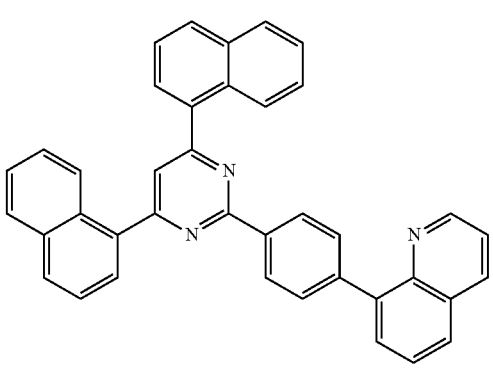

[Chemical Formula 31]
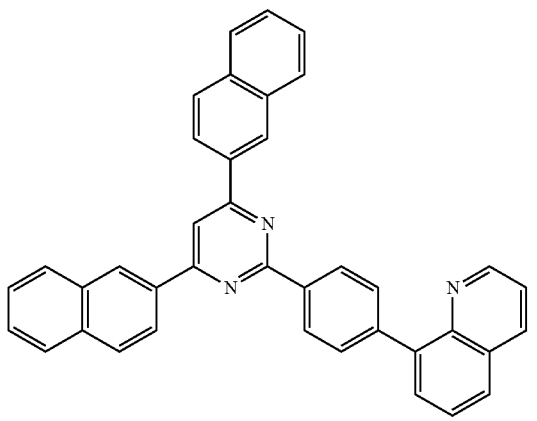
[Chemcial Formula 32]
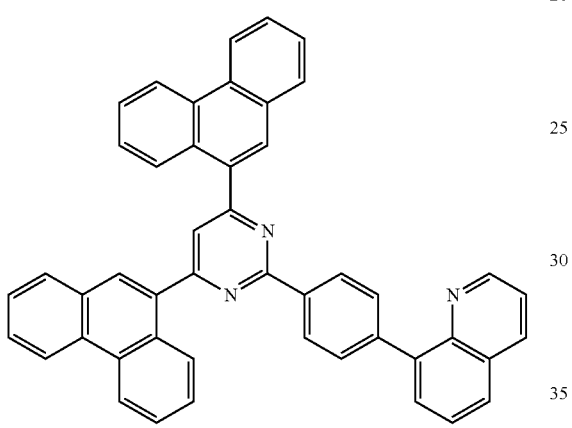
[Chemical Formula 33]
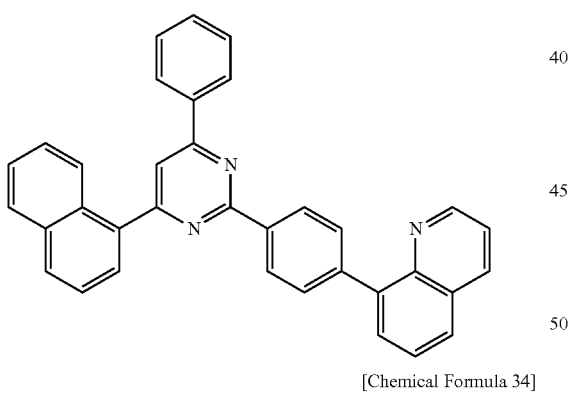
[Chemical Formula 34]
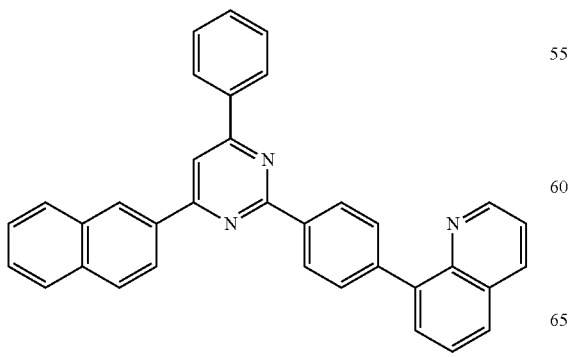
[Chemical Formula 35]
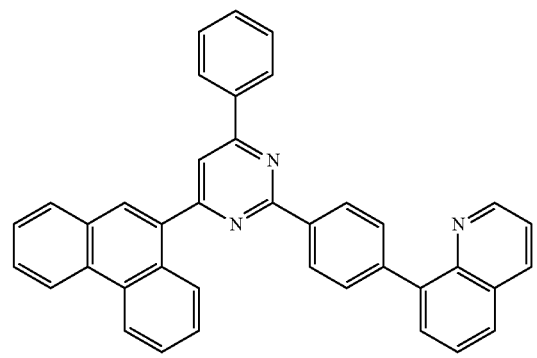
[Chemical Formula 36]
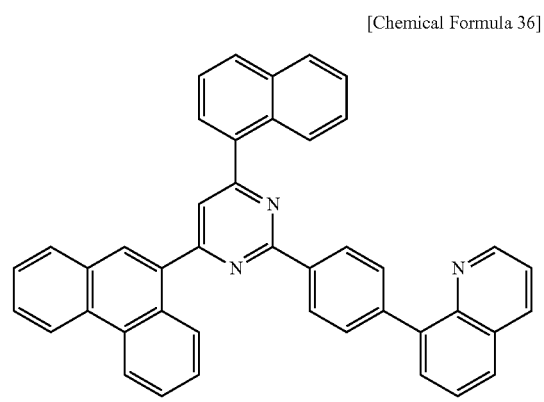
[Chemical Formula 37]
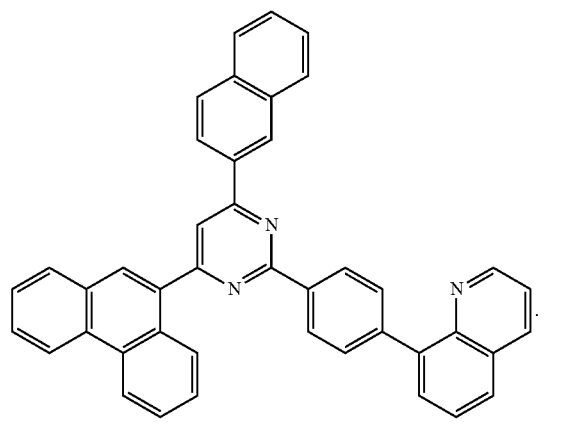
The compound represented by Chemical Formula 1 may be represented by Chemical Formula 1 is represented by at least one of the following Chemical Formulae 38 to 46:

[Chemical Formula 38]
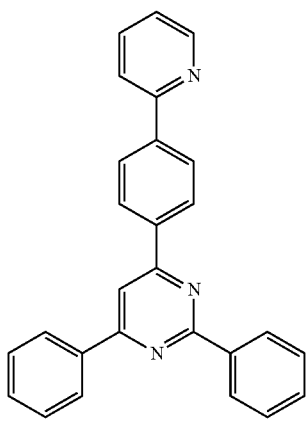
[Chemical Formula 39]
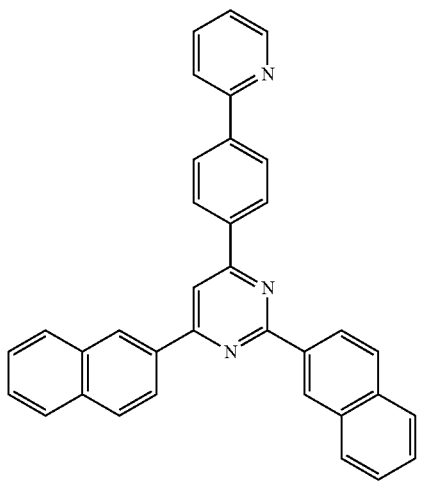
[Chemical Formula 40]
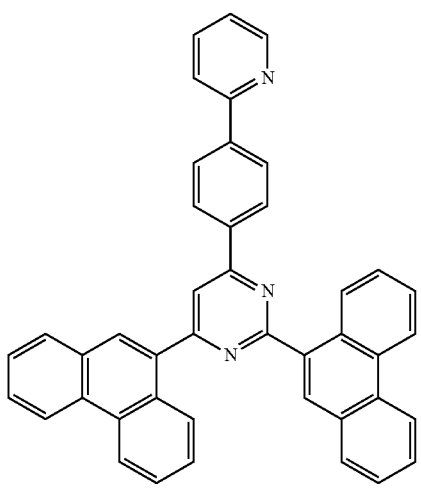
[Chemical Formula 41]
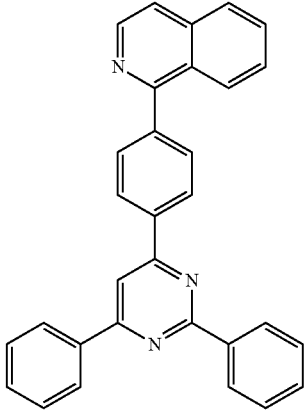
[Chemical Formula 42]
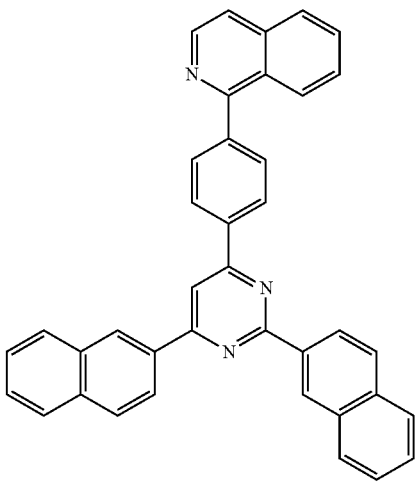
[Chemical Formula 43]
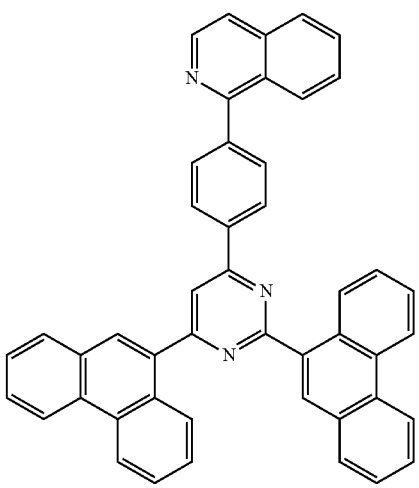

-continued
[Chemical Formula 44]
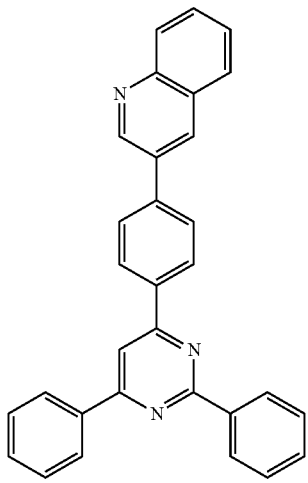
[Chemical Formula 45]
[Chemical Formula 46]
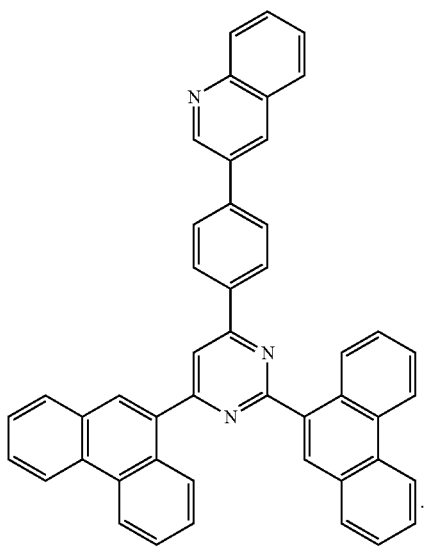
The compound represented by Chemical Formula 1 may be represented by Chemical Formula 1 is represented by at least one of the following Chemical Formulae 47 to 58:
[Chemical Formula 47]
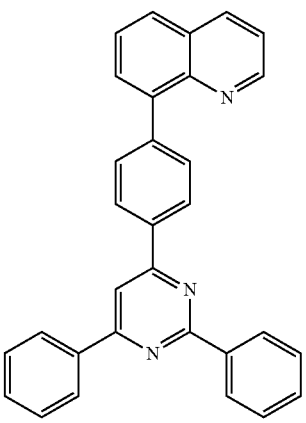
[Chemical Formula 48]
[Chemical Formula 49]

[Chemical Formula 50]
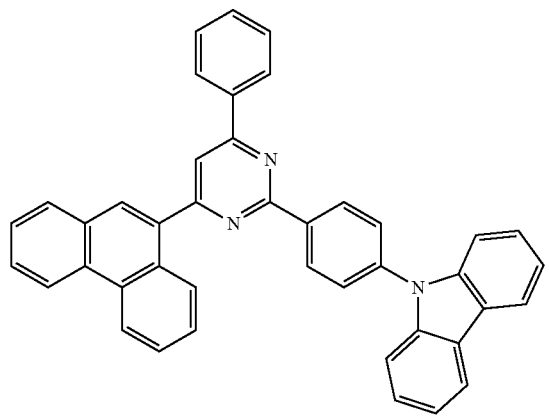
[Chemical Formula 51]
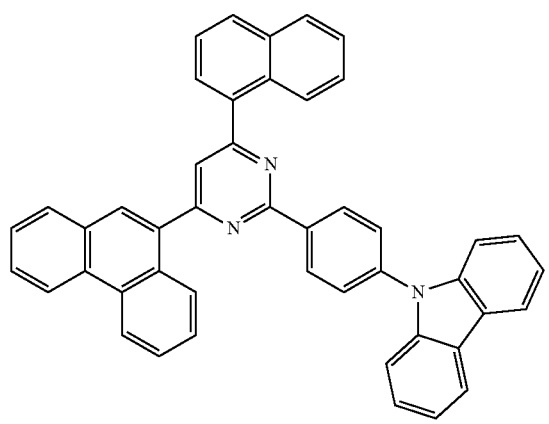
[Chemical Formula 52]
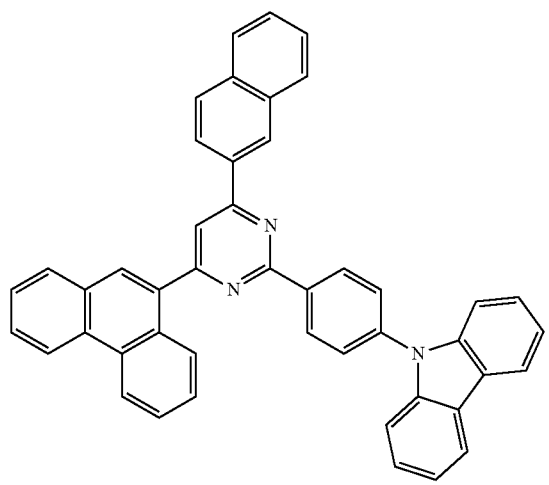
[Chemical Formula 53]
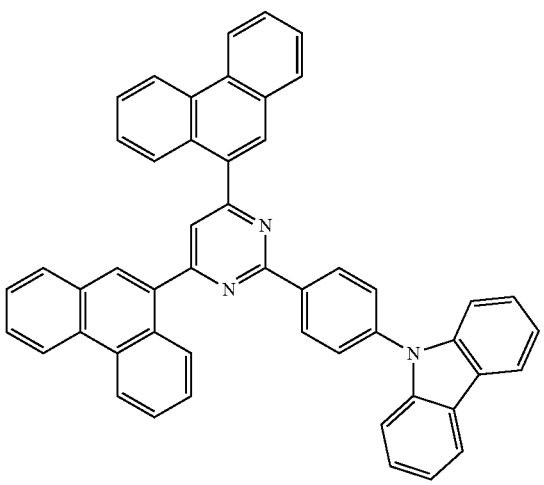
[Chemical Formula 54]
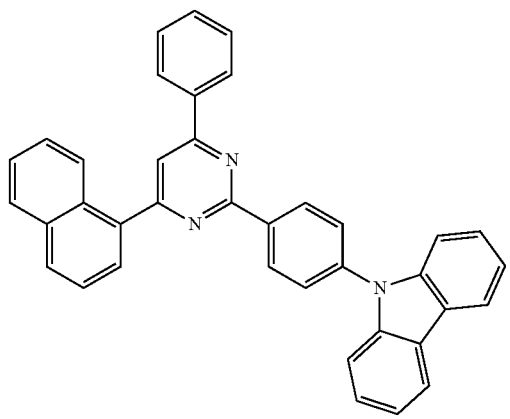
[Chemical Formula 55]
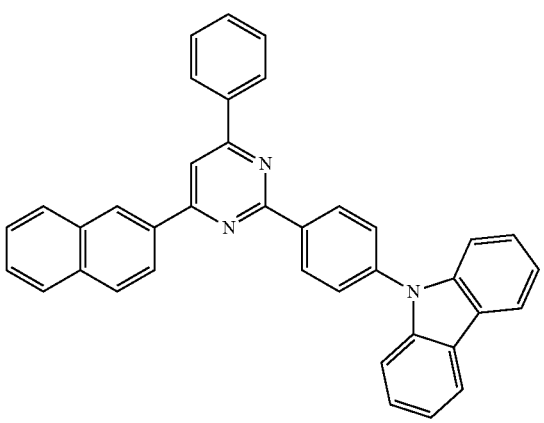

19
-continued

[Chemical Formula 56]

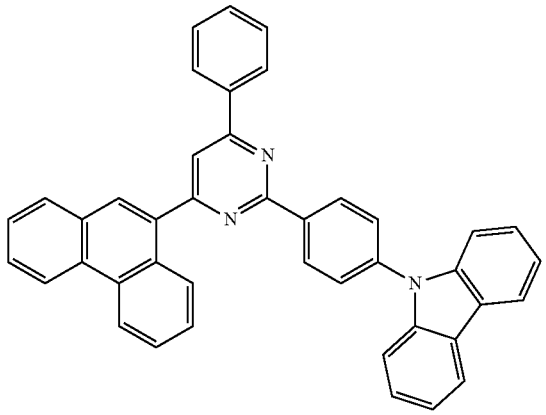

[Chemical Formula 57]

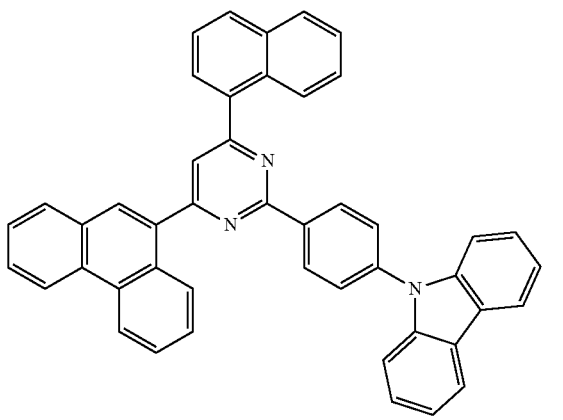

[Chemical Formula 58]

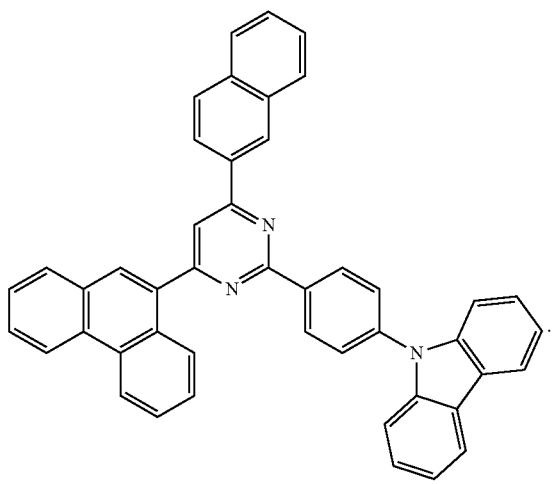

The embodiments may also be realized by providing an organic photoelectric device including an anode; a cathode; and at least one organic thin layer between the anode and cathode, wherein the at least one the organic thin layer includes the compound of an embodiment.

The at least one organic thin layer may include an emission layer, a hole transport layer (HTL), a hole injection layer (HIL), an electron injection layer (EIL), a hole blocking layer, or a combination thereof.

20

The compound may be included in an electron transport layer (ETL) or an electron injection layer (EIL) of the at least one organic thin layer.

The compound may be included in an emission layer of the at least one organic thin layer.

The compound may be a phosphorescent or fluorescent host in an emission layer of the at least one organic thin layer.

The compound may be a fluorescent blue dopant in an emission layer of the at least one organic thin layer.

The organic photoelectric device may be one of an organic light emitting diode, an organic solar cell, an organic transistor, an organic photo-conductor drum, and an organic memory device.

The embodiments may also be realized by providing a display device including the organic photoelectric device of an embodiment.

BRIEF DESCRIPTION OF THE DRAWINGS

The embodiments will become more apparent to those of ordinary skill in the art by describing in detail exemplary embodiments with reference to the attached drawings, in which.

DETAILED DESCRIPTION

Figure 1:
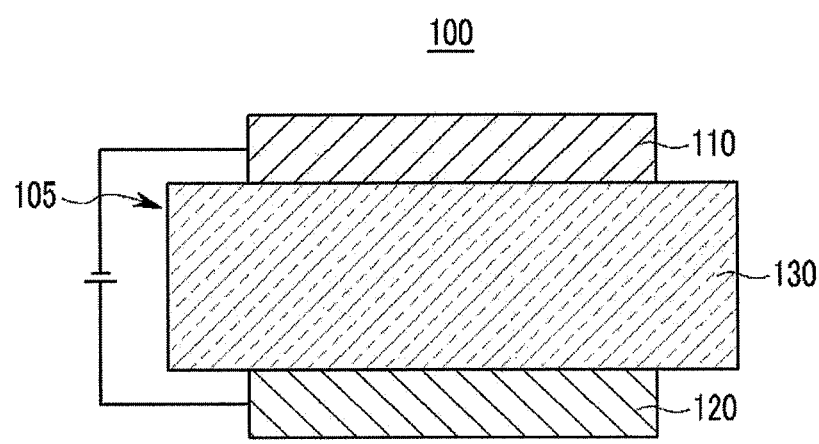
FIGS. 1 to 5 illustrate cross-sectional views of organic light emitting diodes including compounds according to the embodiments.

Korean Patent Application No. 10-2008-0133692, filed on Dec. 24, 2008, and Korean Patent Application No. 10-2009-0072155, filed on Aug. 5, 2009 in the Korean Intellectual Property Office, each entitled: "Novel Compound for Organic Photoelectric Device and Organic Photoelectric Device Including the Same," are incorporated by reference herein in their entirety.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. In addition, it will also be understood that when a layer is referred to as being "between" two layers, it can be the only layer between the two layers, or one or more intervening layers may also be present. Like reference numerals refer to like elements throughout.

As used herein, when specific definition is not otherwise provided, the term "substituted" may refer to one substituted with at least one of a C1 to C30 alkyl, a C1 to C10 alkylsilyl, a C3 to C30 cycloalkyl, a C6 to C30 aryl, a C1 to C10 alkoxy, a fluoro, a C1 to C10 trifluoroalkyl (such as a trifluoromethyl), and a cyano.

As used herein, when specific definition is not otherwise provided, the term "hetero" may refer to one including 1 to 3 atoms, including N, O, S, P, or Si, and remaining carbons in one ring.

As used herein, when a definition is not otherwise provided, the term "combination thereof" may refer to at least two substituents linked to each other, or condensed one of at least two substituents. In addition, the term "room temperature" may refer to a temperature of about 25° C.

The compound for an organic photoelectric device according to an embodiment may include a pyrimidine core, and an aryl moiety and a heteroaryl moiety linked or bonded to the core. For example, the compound for an organic photoelectric device may include various substituents linked to the pyrimidine core to have various energy band gaps, and therefore may satisfy properties desirable for an electron injection layer (EIL), an electron transport layer, and/or an emission layer. The compound having various energies (due to the various substituents) may reinforce electron transport capability, thereby resulting in improvement of efficiency and driving voltage as well as life-span characteristics due to excellent electrochemical and thermal stability during operation.

According to an embodiment, the compound for an organic photoelectric device (including the pyrimidine core) may be represented by the following Chemical Formula 1.

[Chemical Formula 1]

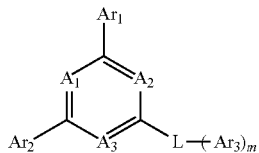

In the above Chemical Formula 1, $A_1$ to $A_3$ may each independently be carbon or nitrogen, provided that at least two of $A_1$ to $A_3$ are nitrogen, $Ar_1$ and $Ar_2$ may each independently be a substituted or unsubstituted C6 to C30 aryl, $Ar_3$ may be a substituted or unsubstituted carbazolyl, a substituted or unsubstituted C2 to C30 heteroaryl, a substituted or unsubstituted C2 to C30 arylamine, a substituted or unsubstituted C2 to C30 heteroarylamine, or a combination thereof, L may be a substituted or unsubstituted phenylene, naphthalene, or anthracene, and m may be an integer of 1 to 3.

When any of $A_1$ to $A_3$ is carbon, it may be represented by CR, where R is hydrogen or a C1 to C15 alkyl.

When $Ar_1$ and $Ar_2$ are each independently a substituted or unsubstituted C6 to C30 aryl, they may include one of phenyl, naphthyl, anthracenyl, phenanthrenyl, pyrenyl, perylenyl, and chrysenyl.

$Ar_1$ and $Ar_2$ may include a substituent, the substituent including, e.g., a C1 to C30 alkyl, a C1 to C10 alkylsilyl, a C3 to C30 cycloalkyl, a C6 to C30 aryl, a C1 to C10 alkoxy, a fluoro, a C1 to C10 trifluoroalkyl (such as a trifluoromethyl), a cyano, or a combination thereof. The pyrimidine core including the aryl may have excellent thermal stability and/or oxidation resistance, thereby resulting in improved life-span characteristics of an organic photoelectric device.

When $Ar_3$ includes a substituent of a n-type heteroaryl having excellent electron affinity, e.g., pyridinyl, quinolinyl, or isoquinolinyl, a n-type material having excellent electron transport capability may be provided. The n-type property may mean a property of a conductive characteristic depending upon a LUMO level, so as to have an anionic characteristic due to the electron formation. In an implementation, $Ar_3$ may include one of imidazole, thiazolyl, oxazolyl, oxadiazolyl, triazolyl, pyridinyl, pyridazine, quinolinyl, isoquinolinyl, acridinyl, imidazopyridinyl, imidazopyrimidinyl, diphenyl amine, dinaphthyl amine, dibiphenyl amine, phenyl naphthyl amine, phenyl diphenyl amine, ditolyl amine, phenyl tolyl amine, carbazole, triphenyl amine, and dipyridyl amine. The pyrimidine core including such a heteroaryl may have reinforced electron transport capability resulting in improvement of efficiency and a driving voltage. Accordingly, the compound of an embodiment may be suitable for a material for an electron injection and/or electron transport layer (ETL) material.

$Ar_3$ may be unsubstituted or substituted with, e.g., a C1 to C30 alkyl, a C1 to C10 alkylsilyl, a C3 to C30 cycloalkyl, a C6 to C30 aryl, a C1 to C30 alkoxy, a fluoro, a cyano, or a combination thereof. Herein, for example, the "combination thereof" may include a fluoroalkyl such as trifluoromethyl. However, $Ar_3$ is not limited thereto.

When L is phenylene, intermolecular interaction may increase to thereby improve thermal stability and π-conjugation length may be controlled to adjust light emission in a visible region. Accordingly, the compound of an embodiment may be applicable to an emission layer of an organic photoelectric device.

The compound represented by the above Chemical Formula 1, e.g., the compound according to an embodiment, may include the pyrimidine core and substituents of $Ar_1$ to $Ar_3$. The pyrimidine core may have relatively high thermal stability and/or oxidation resistance, and the substituents may include various substituents at 2, 4, and 6 positions due to reactivity difference.

Examples of the compound represented by the above Chemical Formula 1 may include compounds represented by the following Chemical Formulae 2 to 58, but are not limited thereto.

[Chemical Formula 2]

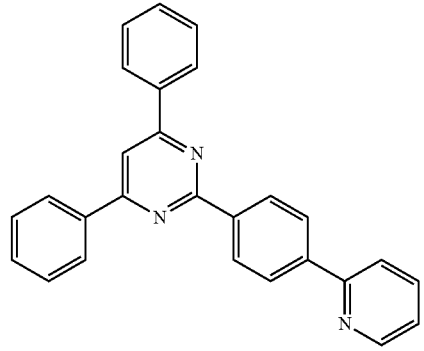

[Chemical Formula 3]

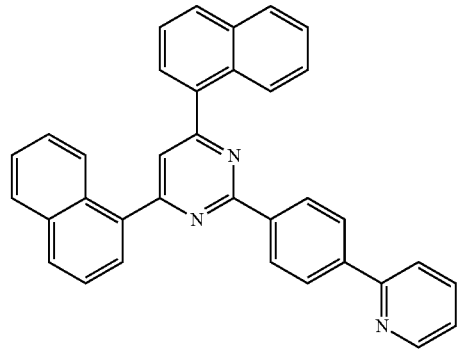

[Chemical Formula 4]
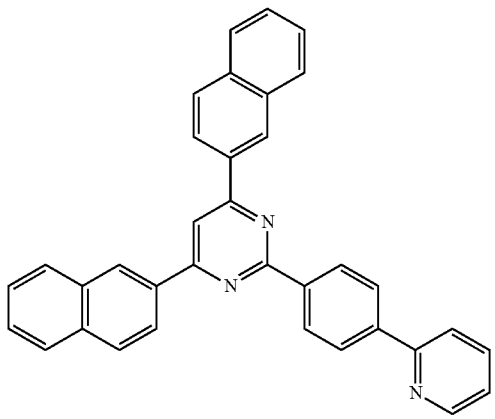
[Chemical Formula 5]
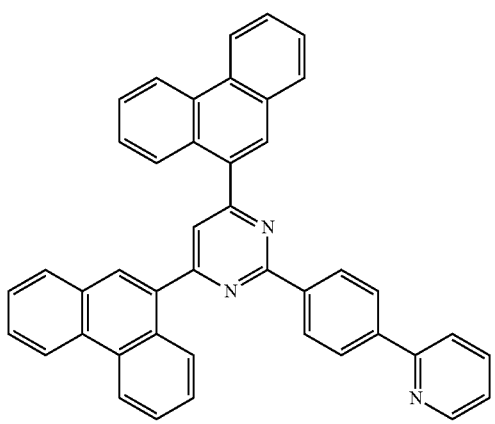
[Chemical Formula 6]
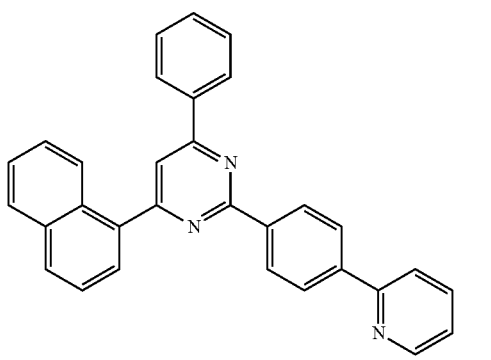
[Chemical Formula 7]
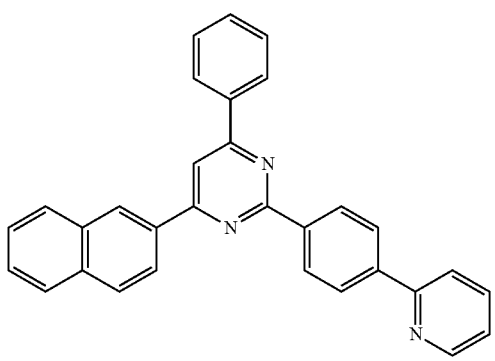
[Chemical Formula 8]
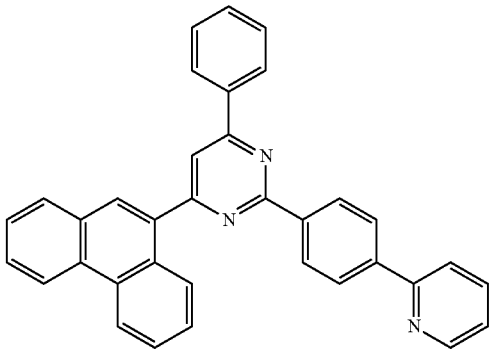
[Chemical Formula 9]
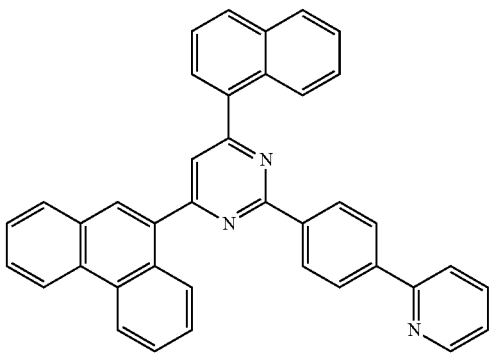
[Chemical Formula 10]
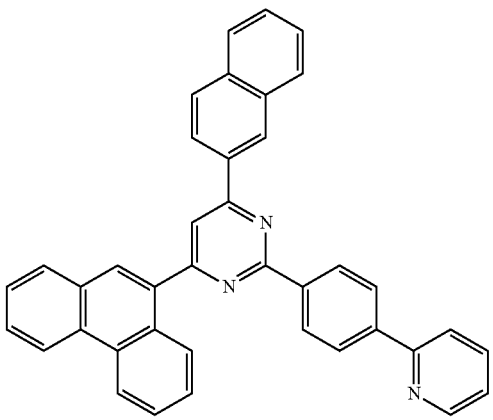
[Chemical Formula 11]
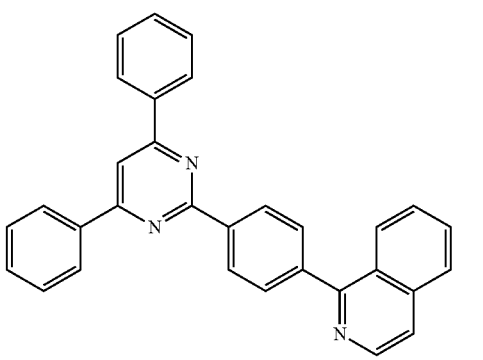

[Chemical Formula 12]
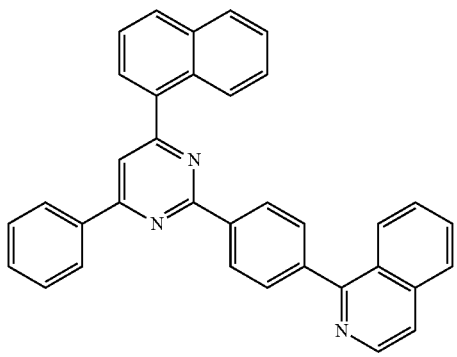
[Chemical Formula 13]
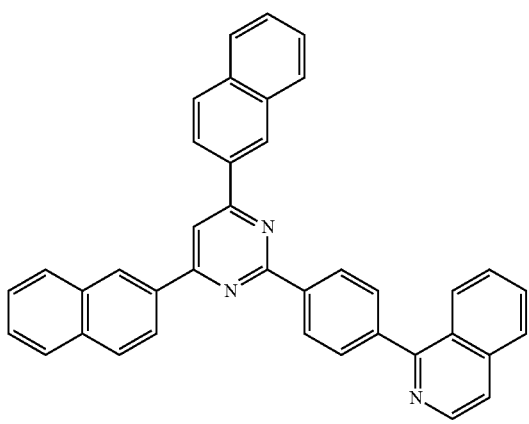
[Chemical Formula 14]
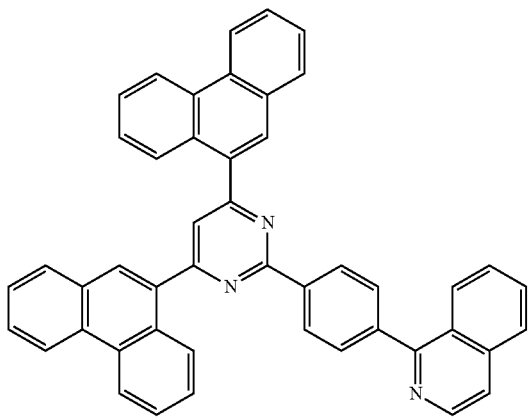
[Chemical Formula 15]
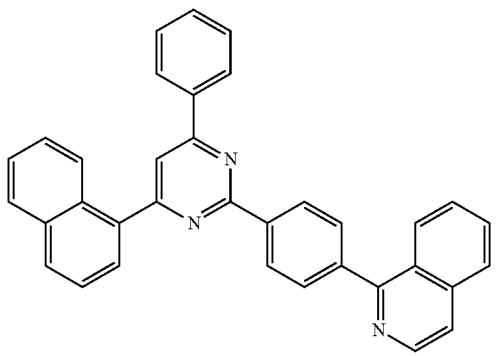
[Chemical Formula 16]
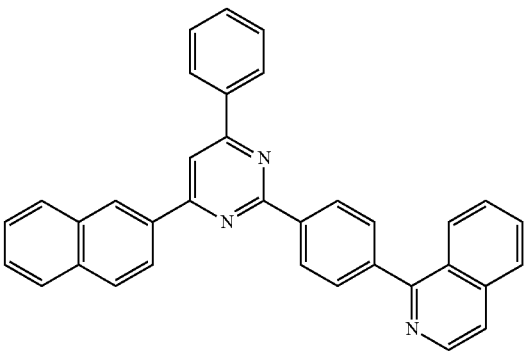
[Chemical Formula 17]
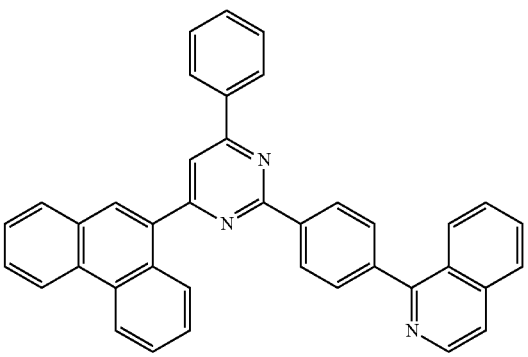
[Chemical Formula 18]
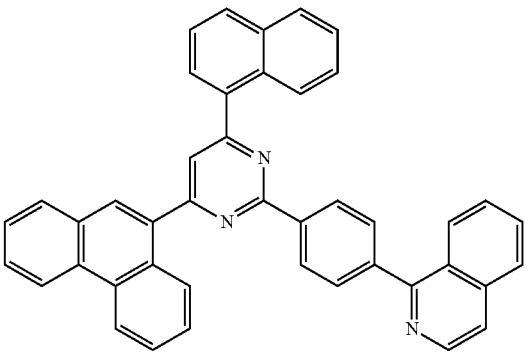
[Chemical Formula 19]
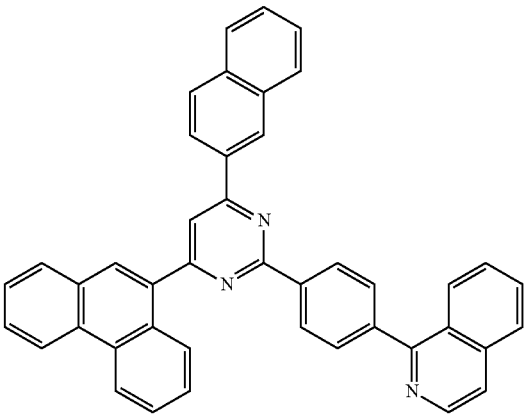

[Chemical Formula 20]
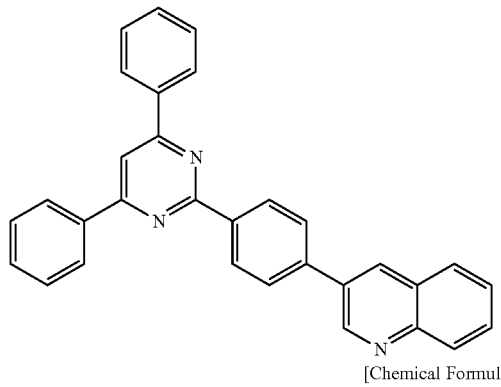
[Chemical Formula 21]
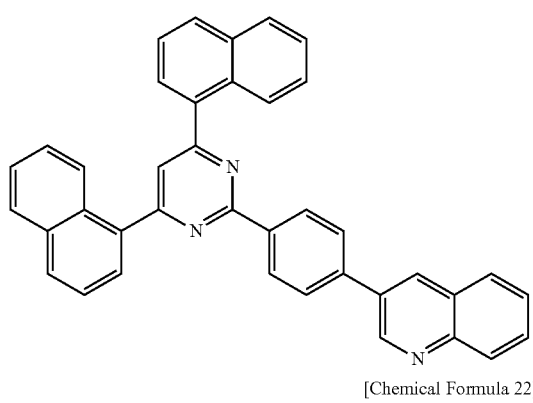
[Chemical Formula 22]
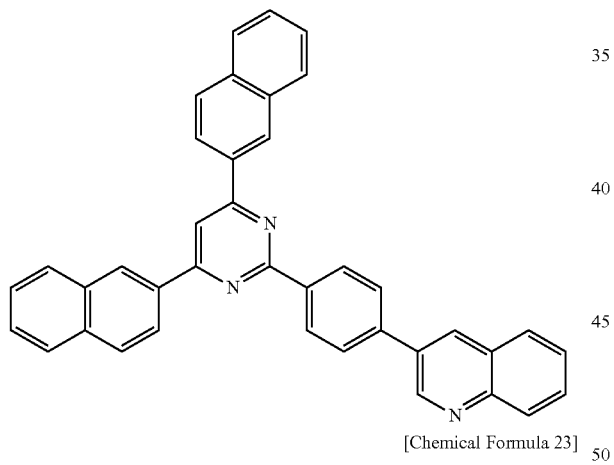
[Chemical Formula 23]
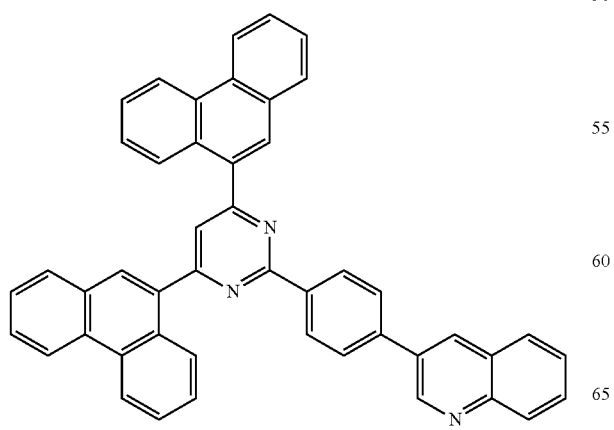
[Chemical Formula 24]
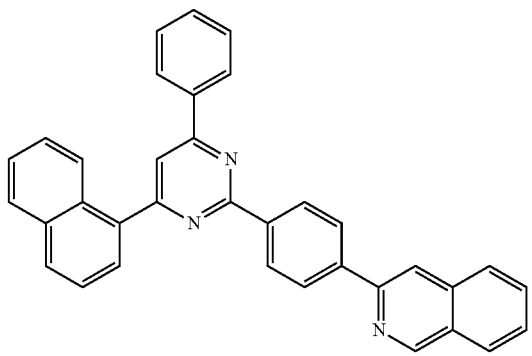
[Chemical Formula 25]
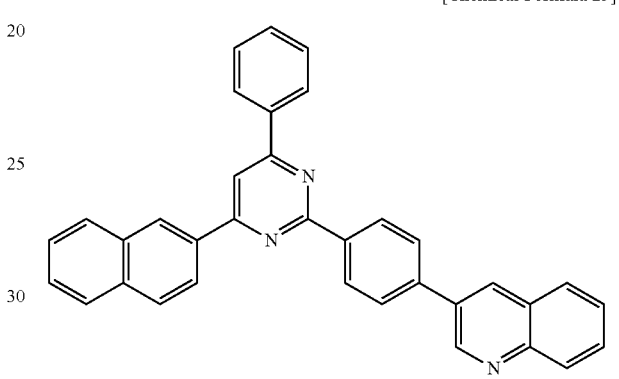
[Chemical Formula 26]
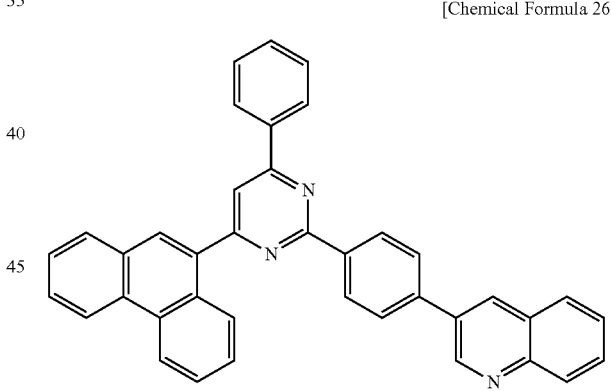
[Chemical Formula 27]
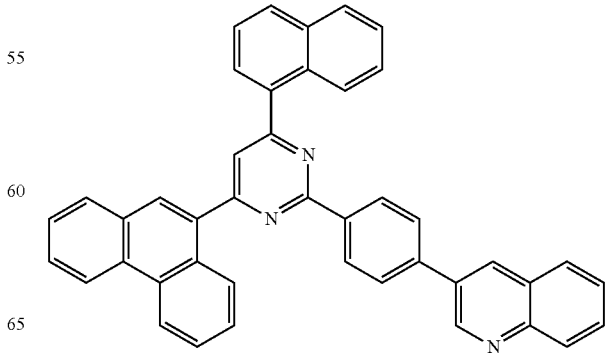

[Chemical Formula 28]
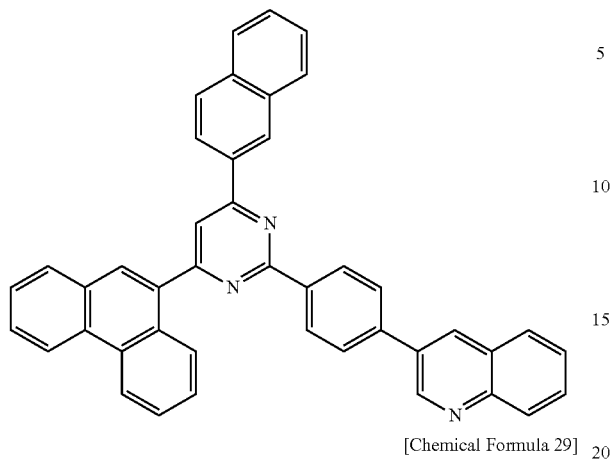
[Chemical Formula 29]
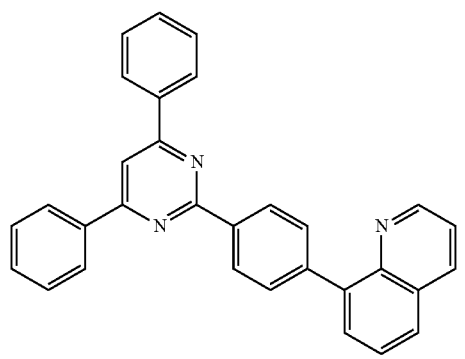
[Chemical Formula 30]
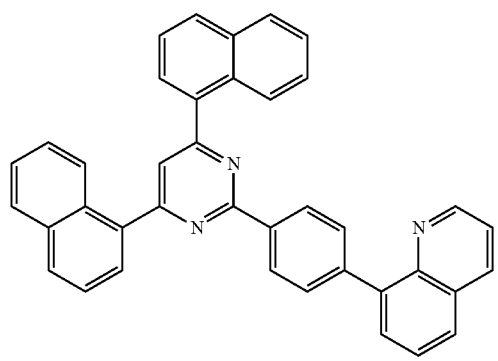
[Chemical Formula 31]
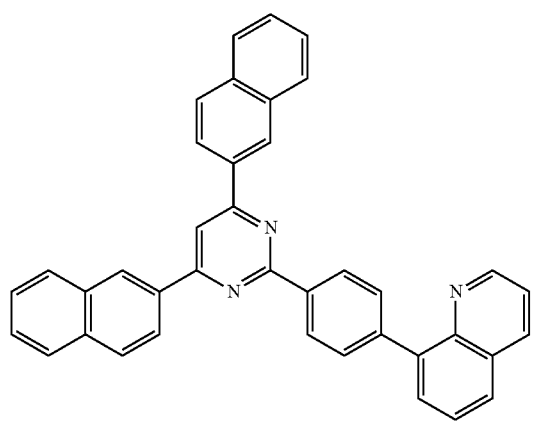
[Chemical Formula 32]
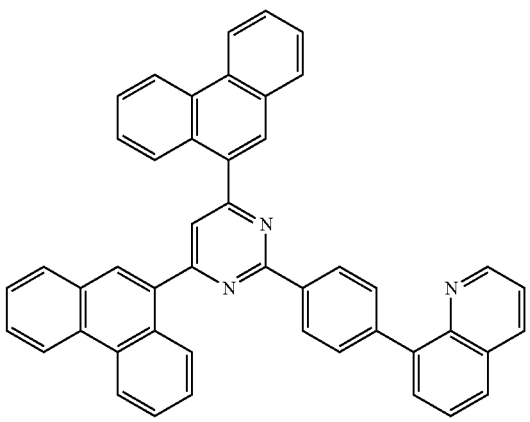
[Chemical Formula 33]
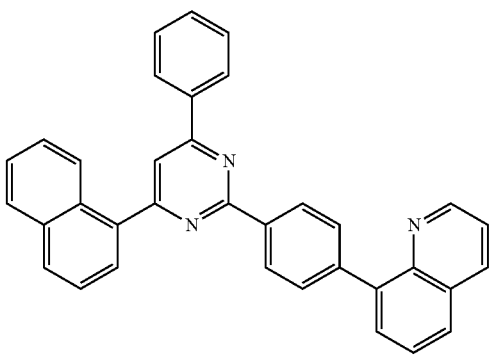
[Chemical Formula 34]
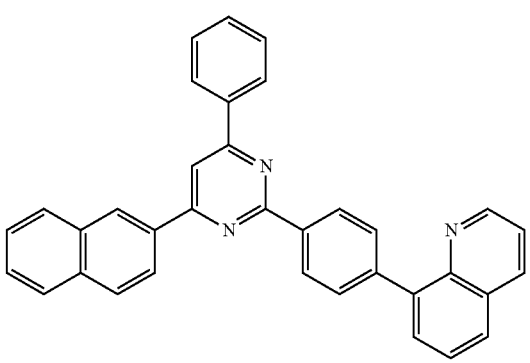
[Chemical Formula 35]

[Chemical Formula 36]
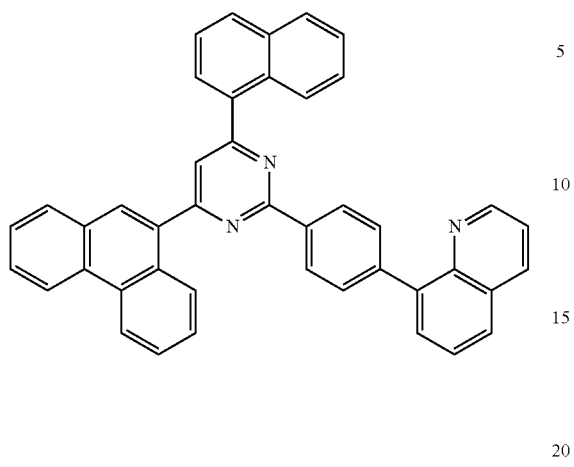
[Chemical Formula 37]
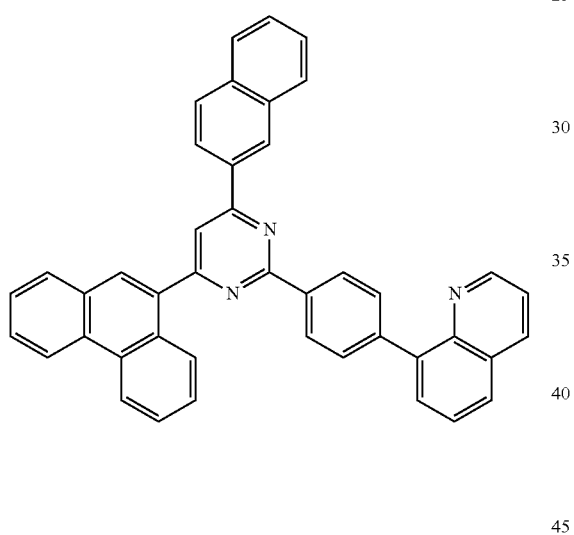
[Chemical Formula 38]
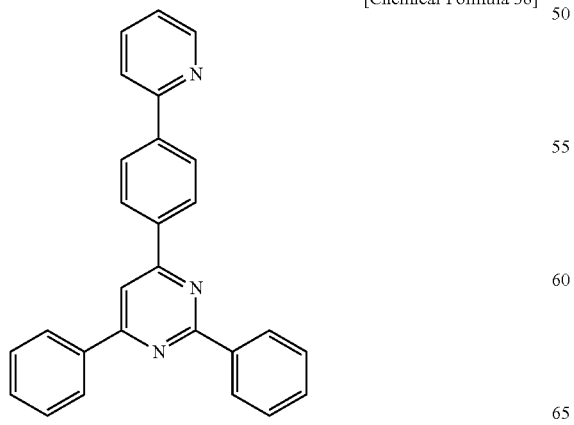
[Chemical Formula 39]
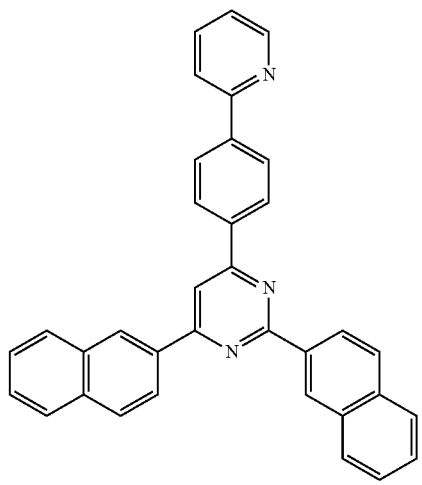
[Chemical Formula 40]
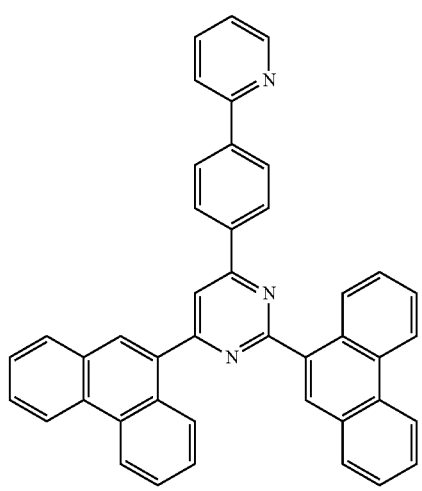
[Chemical Formula 41]
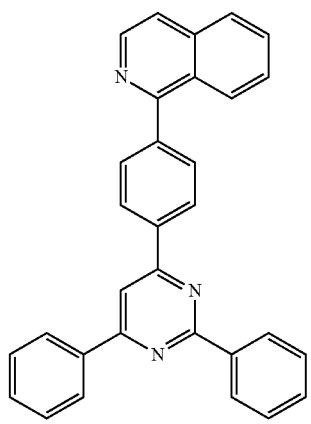

[Chemical Formula 42]
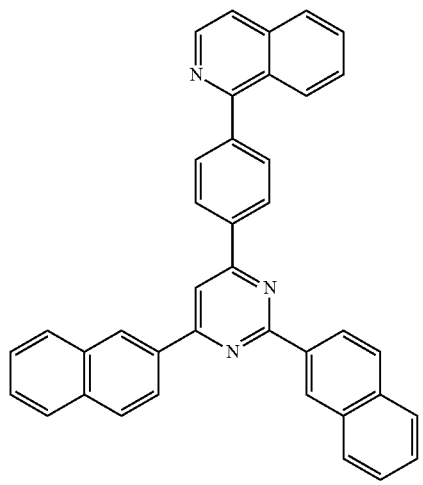
[Chemical Formula 43]
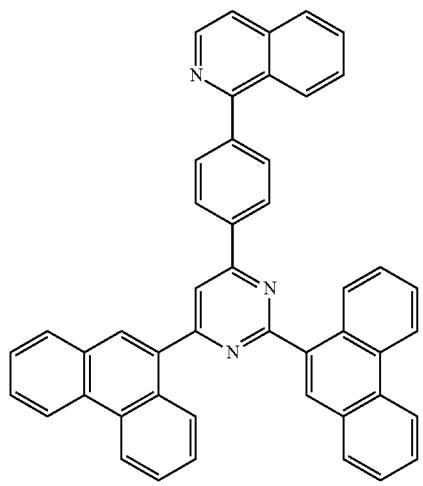
[Chemical Formula 44]
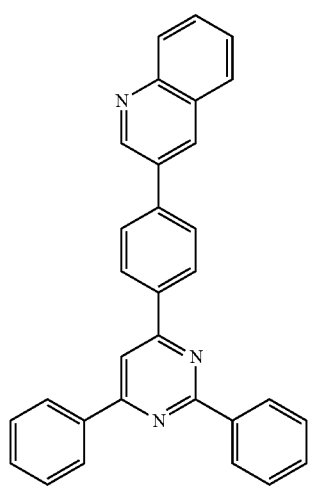
[Chemical Formula 45]
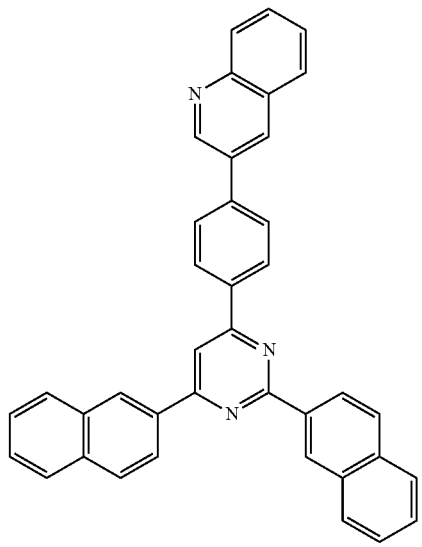
[Chemical Formula 46]
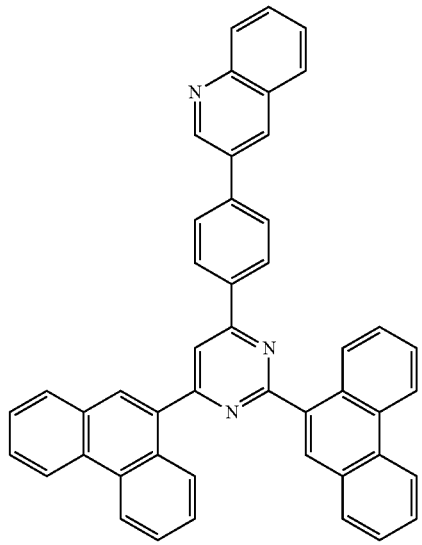
[Chemical Formula 47]
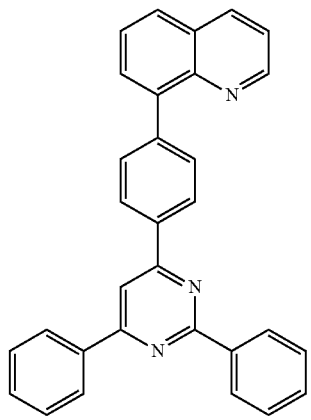

[Chemical Formula 48]
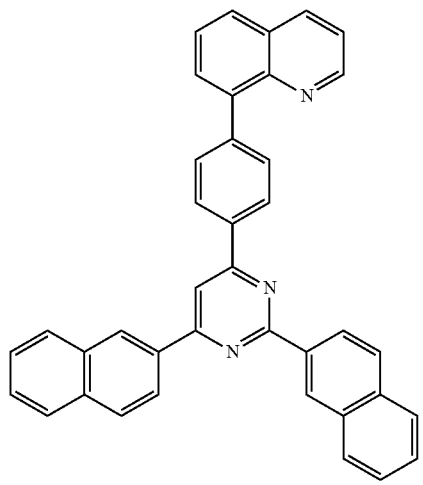
[Chemical Formula 49]
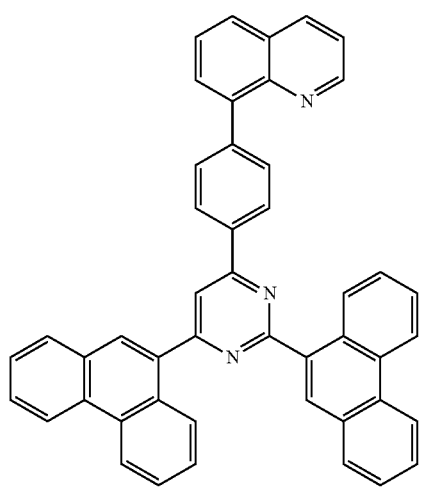
[Chemical Formula 50]
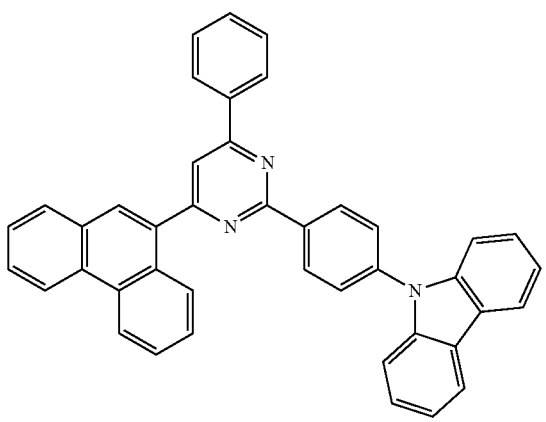
[Chemical Formula 51]
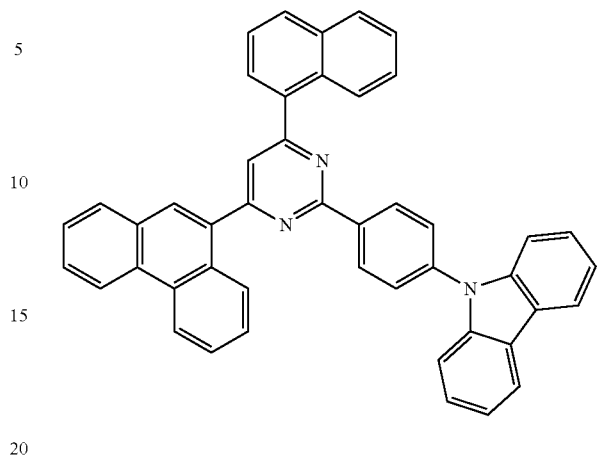
[Chemical Formula 52]
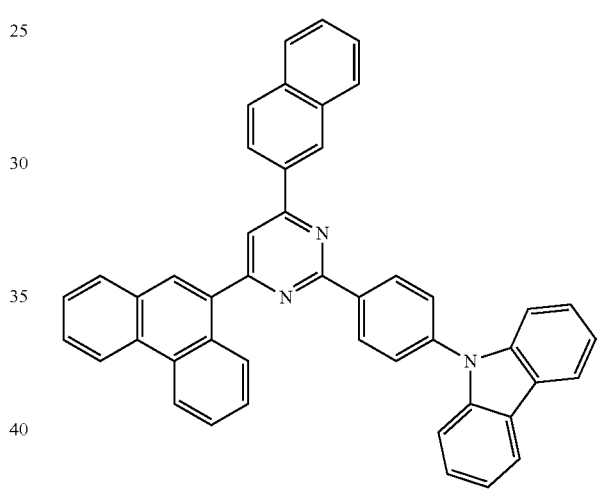
[Chemical Formula 53]
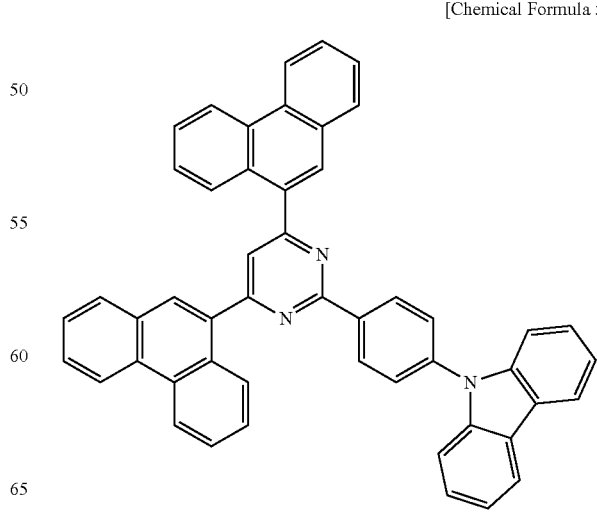

[Chemical Formula 54]

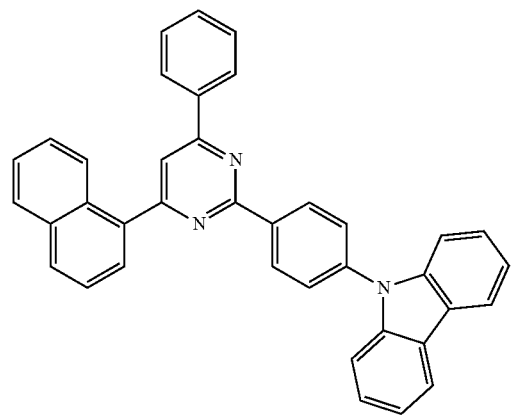

[Chemical Formula 55]

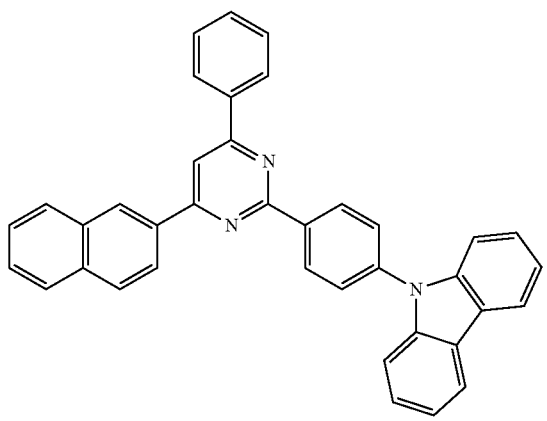

[Chemical Formula 56]

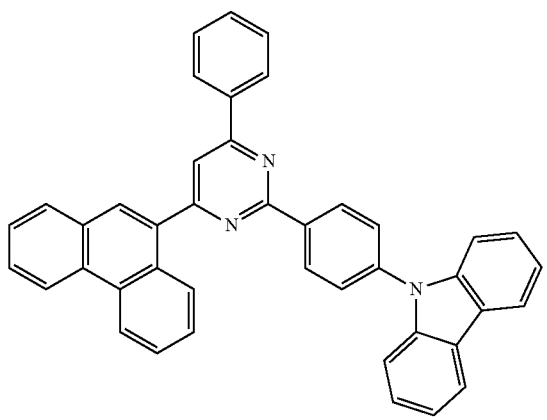

[Chemical Formula 57]

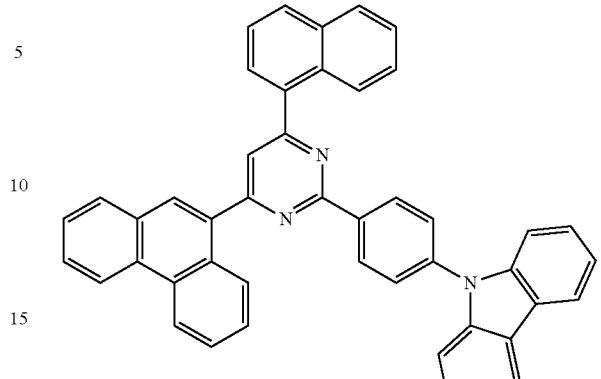

[Chemical Formula 58]

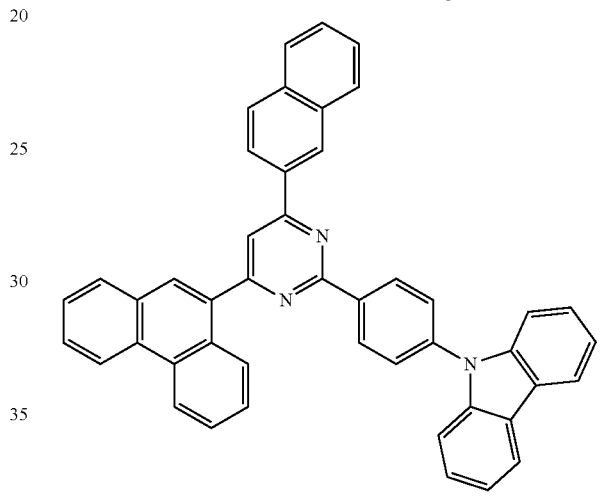

The compound for an organic photoelectric device including the above compounds may play a role in, e.g., light emission, electron injection, and/or transport, and also as a light emitting host (with an appropriate dopant). The compound for an organic photoelectric device may be used for, e.g., phosphorescent or fluorescent host materials, blue light emitting dopant materials, or electron transport materials.

The compound for an organic photoelectric device according to an embodiment may improve life-span and electrochemical and thermal stability, and may decrease driving voltage (thereby improving the life-span and efficiency characteristics) of an organic photoelectric device when included in an organic thin layer.

Another embodiment provides an organic photoelectric device including the compound for the organic photoelectric device. The organic photoelectric device may include, e.g., an organic light emitting diode, an organic solar cell, an organic transistor, an organic photo-conductor drum, an organic memory device, and the like. In an organic solar cell, the compound may be included in an electrode or an electrode buffer layer and may thereby improve quantum efficiency. In an organic transistor, the compound may be used as an electrode material in a gate, a source-drain electrode, and the like.

Hereinafter, an organic light emitting diode will be described in more detail.

The organic light emitting diode may include an anode and a cathode, and at least one organic thin layer between the anode and cathode. The organic thin layer may include the compound for an organic photoelectric device.

The organic thin layer may include, e.g., an emission layer as well as a hole transport layer (HTL), a hole injection layer (HIL), an electron transport layer (ETL), an electron injection layer (EIL), a hole blocking layer, and combinations thereof. At least one layer may include the compound for an organic photoelectric device according to an embodiment. For example, the electron transport layer (ETL) or electron injection layer (EIL) may include the compound of an embodiment. When the compound of an embodiment is included in the emission layer, the compound may act as a phosphorescent or fluorescent host or, in an implementation, a fluorescent blue dopant material.

FIGS. 1 to 5 illustrate cross-sectional views showing an organic light emitting diode including the material for an organic photoelectric device according to the embodiments.

Referring to FIGS. 1 to 5, organic light emitting diodes 100, 200, 300, 400, and 500 according to the embodiments may include at least one organic thin layer 105 between an anode 120 and a cathode 110.

The anode 120 may include an anode material laving a large work function to facilitate hole injection into an organic thin layer. The anode material may include a metal, e.g., nickel, platinum, vanadium, chromium, copper, zinc, and gold, or alloys thereof; a metal oxide, e.g., zinc oxide, indium oxide, indium tin oxide (ITO), and indium zinc oxide (IZO); a combined metal and oxide, e.g., ZnO:Al or $SnO_2$:Sb; or a conductive polymer, e.g., poly(3-methylthiophene), poly[3,4-(ethylene-1,2-dioxy)thiophene] (PEDT), polypyrrole, and/or polyaniline, but is not limited thereto. In an implementation, the anode may include a transparent electrode including ITO (indium tin oxide).

The cathode 110 may include a cathode material having a small work function to facilitate electron injection into an organic thin layer. The cathode material may include a metal, e.g., magnesium, calcium, sodium, potassium, titanium, indium, yttrium, lithium, gadolinium, aluminum, silver, tin, and/or lead, or alloys thereof; or a multi-layered material, e.g., LiF/Al, Liq/Al, $LiO_2$/Al, LiF/Ca, LiF/Al, and $BaF_2$/Ca, but is not limited thereto. In an implementation, the cathode may include a metal electrode including aluminum.

Referring to FIG. 1, the organic photoelectric device 100 may include an organic thin layer 105 including only an emission layer 130.

Figure 2:
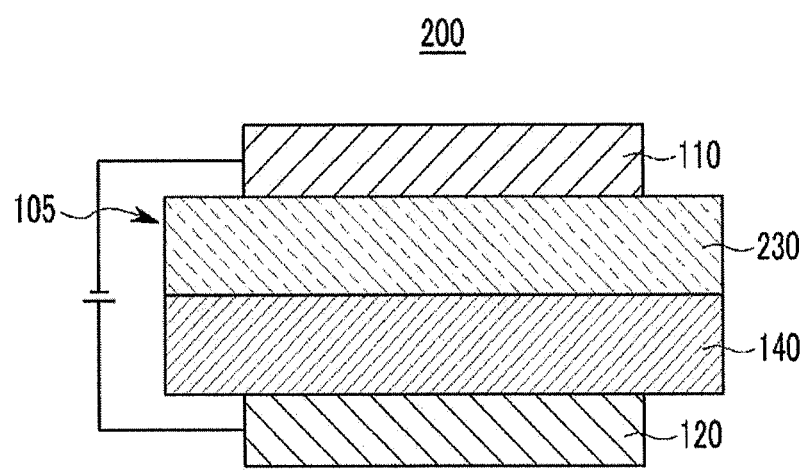

Referring to FIG. 2, a double-layered organic photoelectric device 200 may include an organic thin layer 105 including an emission layer 230 (including an electron transport layer (ETL)) and a hole transport layer (HTL) 140. For example, the emission layer 230 may function as an electron transport layer (ETL); and the hole transport layer (HTL) 140 layer may have an excellent binding property with a transparent electrode, e.g., ITO, and/or an excellent hole transporting property.

Figure 3:
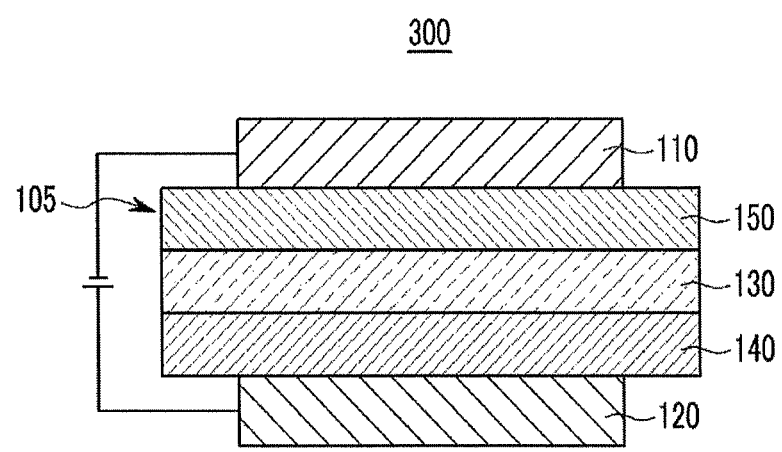

Referring to FIG. 3, a three-layered organic photoelectric device 300 may include an organic thin layer 105 including an electron transport layer (ETL) 150, an emission layer 130, and a hole transport layer (HTL) 140. The emission layer 130 may be independently installed; and layers having an excellent electron transporting property and/or an excellent hole transporting property may be separately stacked.

Figure 4:
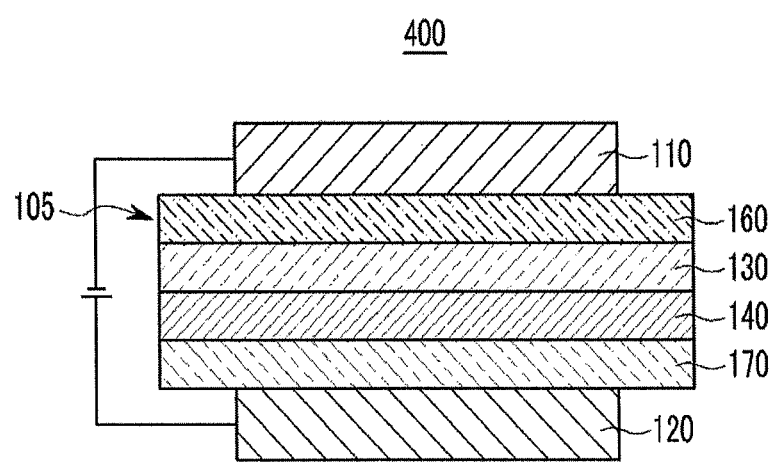

As shown in FIG. 4, a four-layered organic photoelectric device 400 may include an organic thin layer 105 including an electron injection layer (EIL) 160, an emission layer 130, a hole transport layer (HTL) 140, and a hole injection layer (HIL) 170 (for binding with the anode 120 of ITO).

Figure 5:
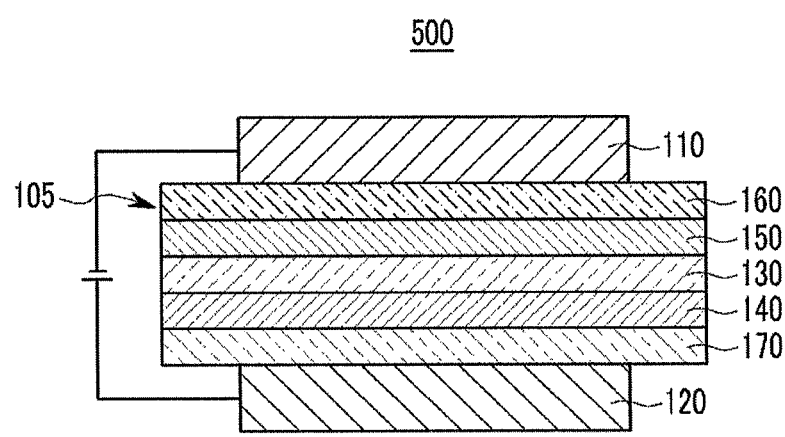

As shown in FIG. 5, a five layered organic photoelectric device 500 may include an organic thin layer 105 including an electron transport layer (ETL) 150, an emission layer 130, a hole transport layer (HTL) 140, and a hole injection layer (HIL) 170, and may further include an electron injection layer (EIL) 160 to achieve a low voltage.

In FIG. 1 to FIG. 5, the organic thin layer 105 (including at least one of an electron transport layer (ETL) 150, an electron injection layer (EIL) 160, an emission layer 130 and 230, a hole transport layer (HTL) 140, a hole injection layer (HIL) 170, and combinations thereof) may include the material for an organic photoelectric device according to an embodiment. The material or compound for the organic photoelectric device may be used for the electron transport layer (ETL) 150 or electron injection layer (EIL) 160. When the material or compound is used for the electron transport layer (ETL), it is possible to provide an organic photoelectric device having a simplified structure, e.g., without an additional hole blocking layer (not shown).

Furthermore, when the compound for an organic photoelectric device is included in the emission layer 130 or 230, the material or compound for the organic photoelectric device may be included as a phosphorescent or fluorescent host or a fluorescent blue dopant.

The organic light emitting diode may be fabricated by forming an anode on a substrate; forming an organic thin layer in accordance with a dry coating method, e.g., an evaporation, a sputtering, a plasma plating, and an ion plating, or a wet coating method, e.g., spin coating, dipping, and flow coating; and providing a cathode thereon.

Another embodiment provides a display device including the organic photoelectric device according to the above-described embodiment.

The following Examples and Comparative Examples are provided in order to set forth particular details of one or more embodiments. However, it will be understood that the embodiments are not limited to the particular details described. Further, the Comparative Examples are set forth to highlight certain characteristics of certain embodiments, and are not to be construed as either limiting the scope of the invention as exemplified in the Examples or as necessarily being outside the scope of the invention in every respect.

Preparing a Compound for an Organic Photoelectric Device

Example 1

Synthesis of Chemical Formula 4 Compound

The compound of the above Chemical Formula 4 was synthesized in accordance with the following Reaction Scheme 1 in two steps.

Reaction Scheme 1

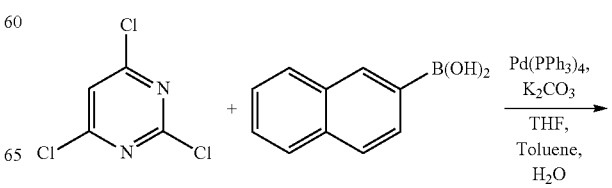

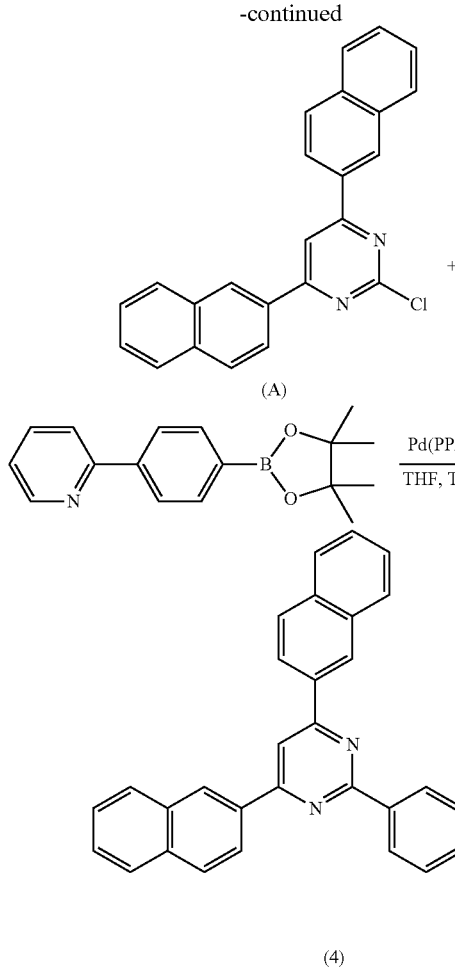

(A)

(4)

First Step; Synthesis of Intermediate Product A 20.0 g (109 mmol) of 2,4,6-trichloropyrimidine, 37.5 g (218 mmol) of 2-naphthylboronic acid, and 6.3 g (5.5 mmol) of tetrakis(triphenylphosphine)palladium were suspended in a mixed solvent of 600 ml of tetrahydrofuran and 400 ml of toluene to provide a suspension. The suspension was added to a solution in which 60.3 g (436 mmol) of potassium carbonate was dissolved in 400 ml of water; and the obtained mixture was heated and refluxed for 9 hours. After separating the reaction fluid into two layers, an organic layer was washed with a saturated sodium chloride aqueous solution and dried with anhydrous sodium sulfate.

The organic solvent was distilled and removed under reduced pressure, and then the residue was recrystallized with toluene. The obtained crystal was separated by filtration and washed with toluene to obtain 29.5 g (yield: 73.8%) of intermediate product (A).

Second Step; Synthesis of Chemical Formula 4 Compound 5.0 g (14 mmol) of the intermediate product (A) (obtained in the first step), 4.2 g (15 mmol) of 2-(4-(4,4,5,5-tetramethyl-1,3,2-dioxaborolan-2-yl)phenyl)pyridine and 0.39 g (0.3 mmol) of tetrakis(triphenylphosphine)palladium were suspended in a mixed solvent of 150 ml of tetrahydrofuran and 100 ml of toluene to provide a suspension. The suspension was added to a solution in which 3.8 g (27 mmol) of potassium carbonate was dissolved in 100 ml of water. The obtained mixture was heated and refluxed for 12 hours. After separating the reaction fluid into two layers, an organic layer was washed with a saturated sodium chloride aqueous solution and dried with anhydrous sodium sulfate.

The organic solvent was distilled and removed under reduced pressure, and then the residue was recrystallized with toluene. The obtained crystal was separated by filtration and washed with toluene to obtain 5.3 g (yield: 80.5%) of the compound of Chemical Formula 4.

MS[M+1]486.

Example 2

Synthesis of Chemical Formula 10 Compound

The compound of the above Chemical Formula 10 was synthesized in accordance with the following Reaction Scheme 2 in three steps.

[Reaction Scheme 2]

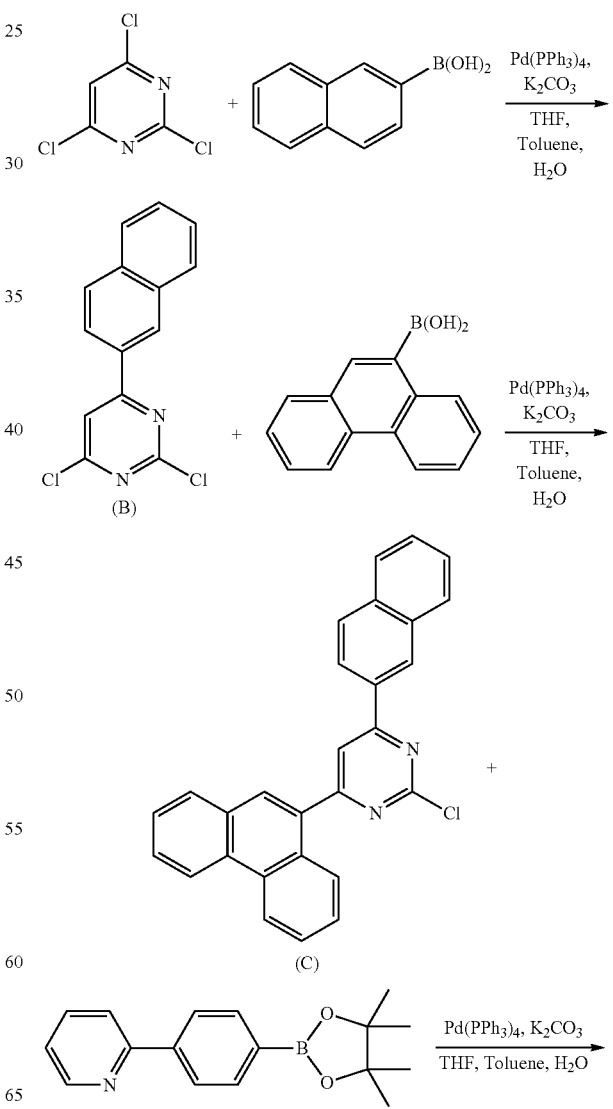

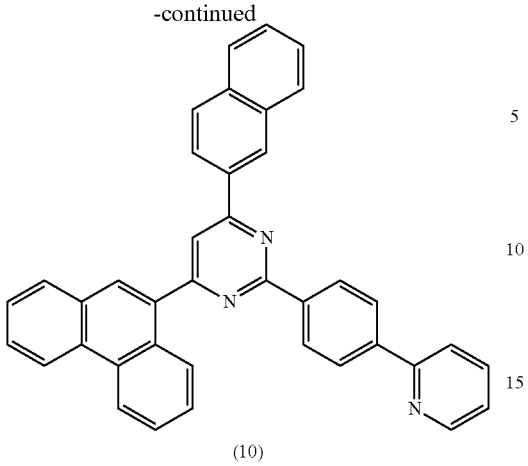

(10)

First Step; Synthesis of Intermediate Product (B)

20.0 g (109 mmol) of 2,4,6-trichloropyrimidine, 18.8 g (109 mmol) of 2-naphthylboronic acid, and 3.2 g (2.8 mmol) of tetrakis(triphenylphosphine)palladium were suspended in a mixed solvent of 600 ml of tetrahydrofuran and 400 ml of toluene to provide a suspension. The suspension was added to a solution in which 30.2 g (218 mmol) of potassium carbonate was dissolved in 400 ml of water, and the obtained mixture was heated and refluxed for 9 hours. After separating the reaction fluid into two layers, an organic layer thereof was washed with a saturated sodium chloride aqueous solution and dried with anhydrous sodium sulfate.

The organic solvent was distilled and removed under reduced pressure, and then the residue was recrystallized with toluene. The obtained crystal was separated by filtration and washed with toluene to obtain 20.1 g (yield: 67.1%) of intermediate product (B).

Second Step; Synthesis of Intermediate Product (C)

20.0 g (73 mmol) of the intermediate product (B) obtained in the first step, 16.2 g (73 mmol) of 9-phenanthreneboronic acid, and 2.1 g (1.8 mmol) of tetrakis(triphenylphosphine)palladium were suspended in a mixed solvent of 600 ml of tetrahydrofuran and 400 ml of toluene to provide a suspension. The suspension was added to a solution in which 20.2 g (146 mmol) of potassium carbonate was dissolved in 400 ml of water, and the obtained mixture was heated and refluxed for 9 hours. After separating the reaction fluid into two layers, an organic layer thereof was washed with a saturated sodium chloride aqueous solution and dried with anhydrous sodium sulfate.

The organic solvent was distilled and removed under reduced pressure, and then the residue was recrystallized with toluene. The obtained crystal was separated by filtration and washed with toluene to obtain 19.4 g (yield: 63.9%) of intermediate product (C).

Third Step; Synthesis of Chemical Formula 10 Compound 5.8 g (14 mmol) of the intermediate product (C) obtained in the second step, 4.2 g (15 mmol) of 2-(4-(4,4,5,5-tetramethyl-1,3,2-dioxaborolan-2-yl)phenyl)pyridine and 0.39 g (0.3 mmol) of tetrakis(triphenylphosphine)palladium were suspended in a mixed solvent of 170 ml of tetrahydrofuran and 115 ml of toluene to provide a suspension. The suspension was added to a solution in which 3.8 g (27 mmol) of potassium carbonate was dissolved in 115 ml of water. The obtained mixture was heated and refluxed for 12 hours. After separating the reaction fluid into two layers, an organic layer thereof was washed with a saturated sodium chloride aqueous solution and dried with anhydrous sodium sulfate.

The organic solvent was distilled and removed under reduced pressure, and then the residue was recrystallized with toluene. The extracted crystal was separated by filtration and washed with toluene to obtain 5.1 g (yield: 67.5%) of the compound of Chemical Formula 10.

MS[M+1]536.

Example 3

Synthesis of Chemical Formula 13 Compound

The compound of the above Chemical Formula 13 was synthesized in accordance with the following Reaction Scheme 3.

Reaction Scheme 3

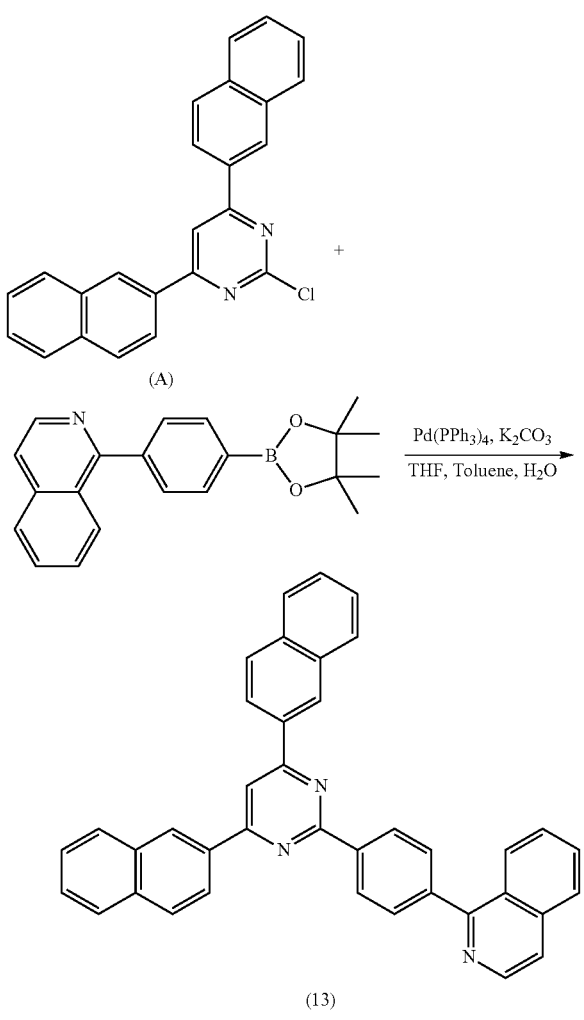

(13)

5.0 g (14 mmol) of the intermediate product (A) obtained in the first step of Example 1, 5.0 g (15 mmol) of 1-(4-(4,4,5,5-tetramethyl-1,3,2-dioxaborolan-2-yl)phenyl)isoquinoline, and 0.39 g (0.3 mmol) of tetrakis(triphenylphosphine)palladium were suspended in a mixed solvent of 150 ml of tetrahydrofuran and 100 ml of toluene to provide a suspension. The suspension was added to a solution in which 3.8 g (27 mmol)

of potassium carbonate was dissolved in 100 ml of water. The obtained mixture was heated and refluxed for 12 hours. After separating the reaction fluid into two layers, an organic layer thereof was washed with a saturated sodium chloride aqueous solution and dried with anhydrous sodium sulfate.

The organic solvent was distilled and removed under reduced pressure, and then the residue was recrystallized with toluene. The extracted crystal was separated by filtration and washed with toluene to obtain 6.2 g (yield: 82.2%) of the compound of Chemical Formula 13.

MS[M+1]536.

Example 4

Synthesis of Chemical Formula 22 Compound

The compound of the above Chemical Formula 22 was synthesized in accordance with the following Reaction Scheme 4.

Reaction Scheme 4

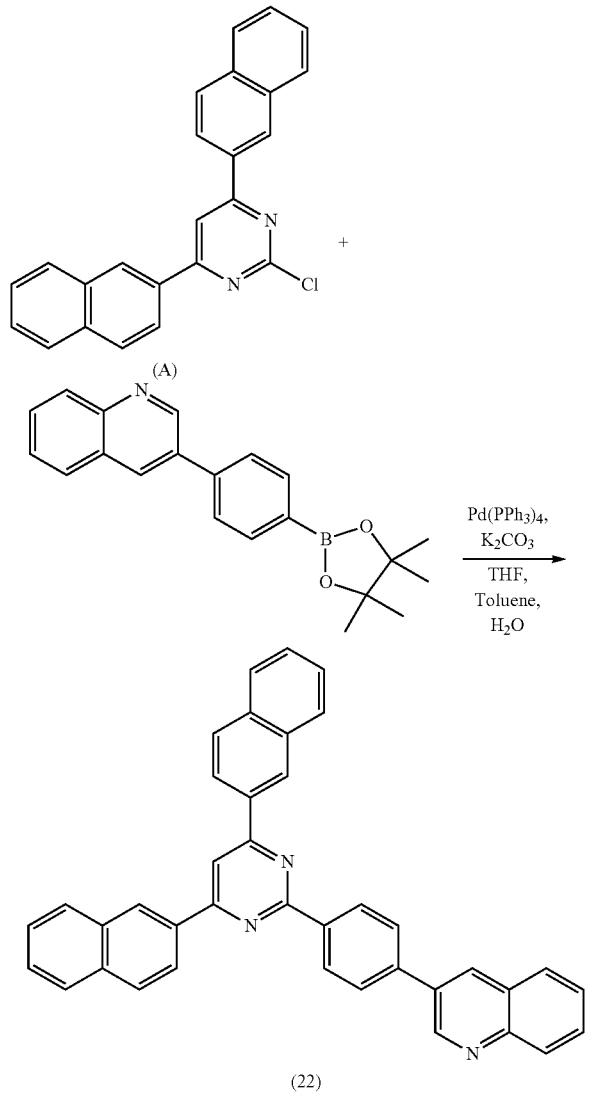

(22)

5.0 g (14 mmol) of the intermediate product (A) obtained in the first step of Example 1, 5.0 g (15 mmol) of 3-(4-(4,4,5,5-tetramethyl-1,3,2-dioxaborolan-2-yl)phenyl)quinoline and 0.39 g (0.3 mmol) of tetrakis(triphenylphosphine)palladium were suspended in a mixed solvent of 150 ml of tetrahydrofuran and 100 ml of toluene to provide a suspension. The suspension was added to a solution in which 3.8 g (27 mmol) of potassium carbonate was dissolved in 100 ml of water. The obtained mixture was heated and refluxed for 12 hours. After separating the reaction fluid into two layers, an organic layer thereof was washed with a saturated sodium chloride aqueous solution and dried with anhydrous sodium sulfate.

The organic solvent was distilled and removed under reduced pressure, and then the residue was recrystallized with toluene. The extracted crystal was separated by filtration and washed with toluene to obtain 4.8 g (yield: 63.4%) of the compound of Chemical Formula 22.

MS[M+1]536.

Example 5

Synthesis of Chemical Formula 28 Compound

The compound of the above Chemical Formula 28 was synthesized in accordance with the following Reaction Scheme 5.

Reaction Scheme 5

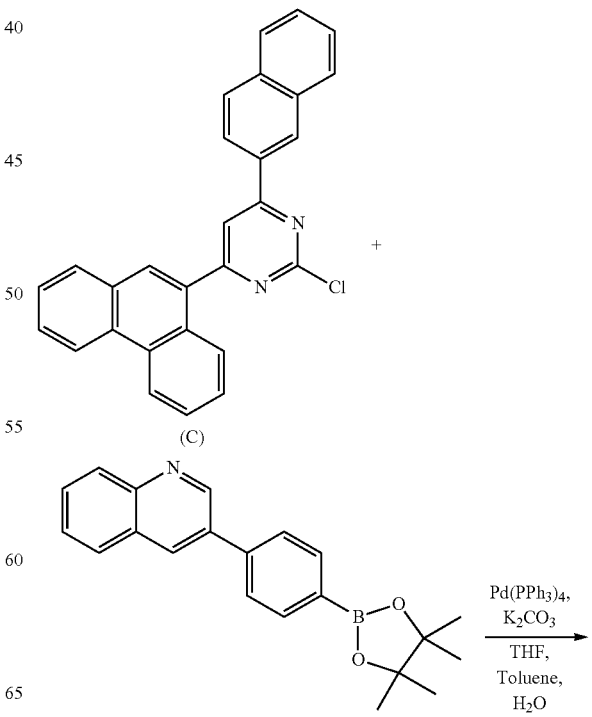

(C)

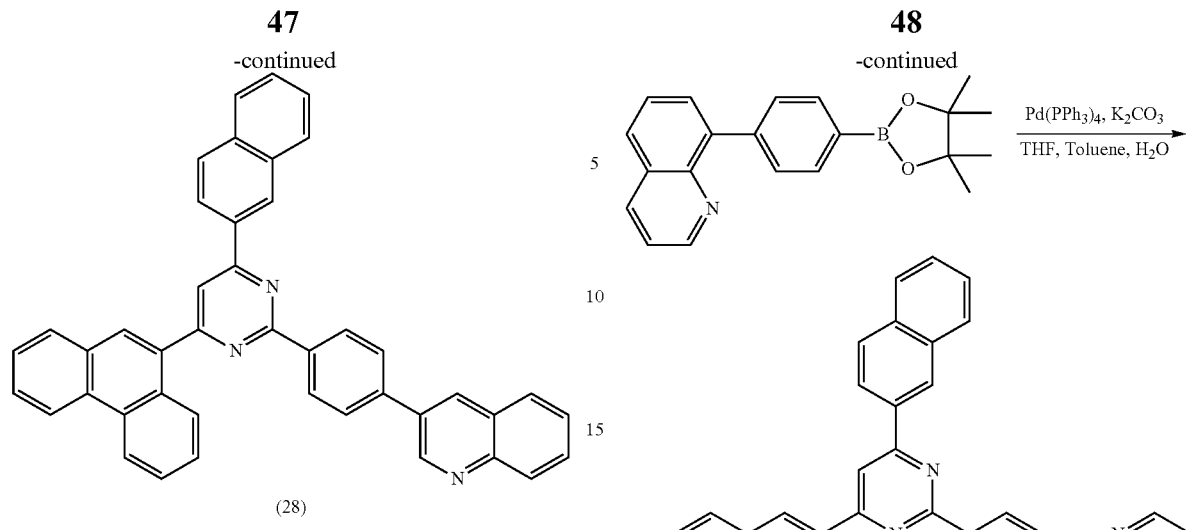

(28)

5.8 g (14 mmol) of the intermediate product (C) obtained in the first step of Example 2, 5.0 g (15 mmol) of 3-(4-(4,4,5,5-tetramethyl-1,3,2-dioxaborolan-2-yl)phenyl)quinoline, and 0.39 g (0.3 mmol) of tetrakis(triphenylphosphine)palladium were suspended in a mixed solvent of 170 ml of tetrahydrofuran and 115 ml of toluene to provide a suspension. The suspension was added to a solution in which 3.8 g (27 mmol) of potassium carbonate was dissolved in 115 ml of water. The obtained mixture was heated and refluxed for 12 hours. After separating the reaction fluid into two layers, an organic layer thereof was washed with a saturated sodium chloride aqueous solution and dried with anhydrous sodium sulfate.

The organic solvent was distilled and removed under reduced pressure, and then the residue was recrystallized with toluene. The extracted crystal was separated by filtration and washed with toluene to obtain 5.1 g (yield: 61.9%) of the compound of Chemical Formula 28.

MS[M+1]586.

Example 6

Synthesis of Chemical Formula 31 Compound

The compound of the above Chemical Formula 31 was synthesized in accordance with the following Reaction Scheme 6.

Reaction Scheme 6

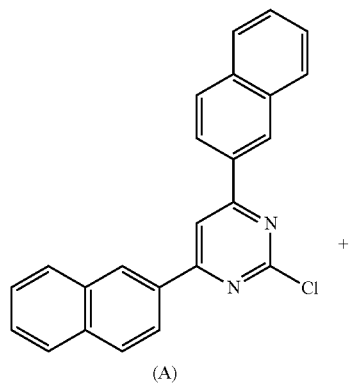

(A)

(31)

5.0 g (14 mmol) of the intermediate product (A) obtained in the first step of Example 1, 5.0 g (15 mmol) of 8-(4-(4,4,5,5-tetramethyl-1,3,2-dioxaborolan-2-yl)phenyl)quinoline, and 0.39 g (0.3 mmol) of tetrakis(triphenylphosphine)palladium were suspended in a mixed solvent of 150 ml of tetrahydrofuran and 100 ml of toluene to provide a suspension. The suspension was added to a solution in which 3.8 g (27 mmol) of potassium carbonate was dissolved in 100 ml of water. The obtained mixture was heated and refluxed for 12 hours. After separating the reaction fluid into two layers, an organic layer thereof was washed with a saturated sodium chloride aqueous solution and dried with anhydrous sodium sulfate.

The organic solvent was distilled and removed under reduced pressure, and then the residue was recrystallized with toluene. The extracted crystal was separated by filtration and washed with toluene to obtain 6.0 g (yield: 79.5%) of the compound of Chemical Formula 31.

MS[M+1]536.

Example 7

Synthesis of Chemical Formula 45 Compound

The compound of the above Chemical Formula 45 was synthesized in accordance with the following Reaction Scheme 7 in two steps.

Reaction Scheme 7

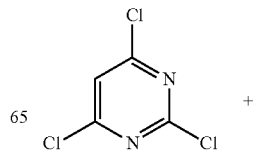

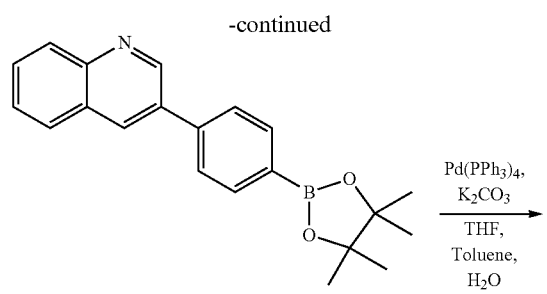

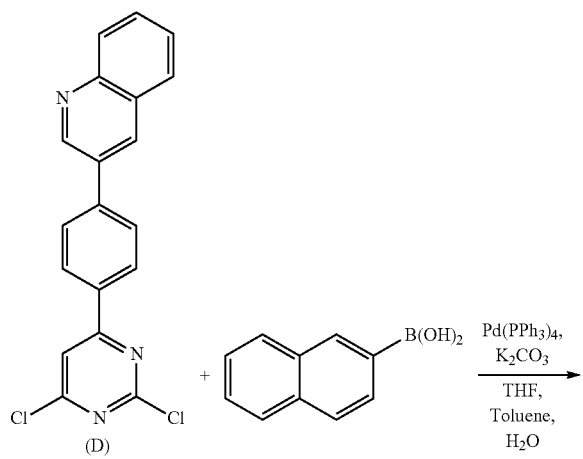

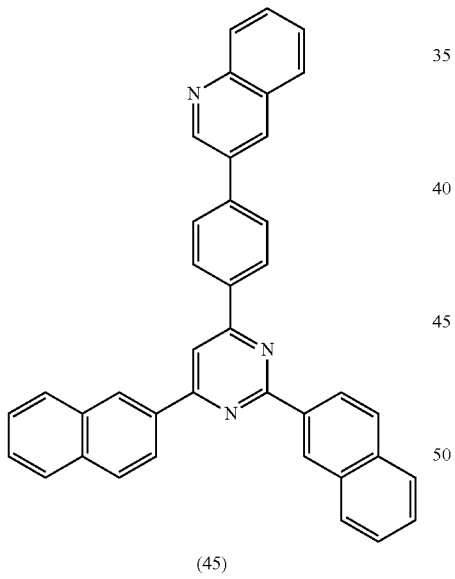

(45)

First Step; Synthesis of Intermediate Product (D)

20.0 g (109 mmol) of 2,4,6-trichloropyrimidine, 39.7 g (120 mmol) of 3-(4-(4,4,5,5-tetramethyl-1,3,2-dioxaborolan-2-yl)phenyl)quinoline, and 3.2 g (2.7 mmol) of tetrakis(triphenylphosphine)palladium were suspended in a mixed solvent of 600 ml of tetrahydrofuran and 400 ml of toluene to provide a suspension. The suspension was added to a solution in which 30.2 g (218 mmol) of potassium carbonate was dissolved in 400 ml of water, and the obtained mixture was heated and refluxed for 9 hours. After separating the reaction fluid into two layers, an organic layer thereof was washed with a saturated sodium chloride aqueous solution and dried with anhydrous sodium sulfate.

The organic solvent was distilled and removed under reduced pressure, and then the residue was recrystallized with toluene. The obtained crystal was separated by filtration and washed with toluene to obtain 26.3 g (yield: 68.5%) of intermediate product (D).

Second Step; Synthesis of Chemical Formula 45 Compound 4.9 g (14 mmol) of the intermediate product (D) obtained in the first step, 5.3 g (31 mmol) of 2-naphthylboronic acid, and 0.8 g (0.7 mmol) of tetrakis(triphenylphosphine)palladium were suspended in a mixed solvent of 150 ml of tetrahydrofuran and 100 ml of toluene to provide a suspension. The suspension was added to a solution in which 7.6 g (56 mmol) of potassium carbonate was dissolved in 400 ml of water, and the obtained mixture was heated and refluxed for 12 hours. After separating the reaction fluid into two layers, an organic layer thereof was washed with a saturated sodium chloride aqueous solution and dried with anhydrous sodium sulfate.

The organic solvent was distilled and removed under reduced pressure, and then the residue was recrystallized with toluene. The obtained crystal was separated by filtration and washed with toluene to obtain 5.4 g (yield: 72.0%) of the compound of Chemical Formula 45.

MS[M+1]536.

Example 8

Synthesis of Chemical Formula 46 Compound

The compound of the above Chemical Formula 46 was synthesized in accordance with the following Reaction Scheme 8.

[Reaction Scheme 8]

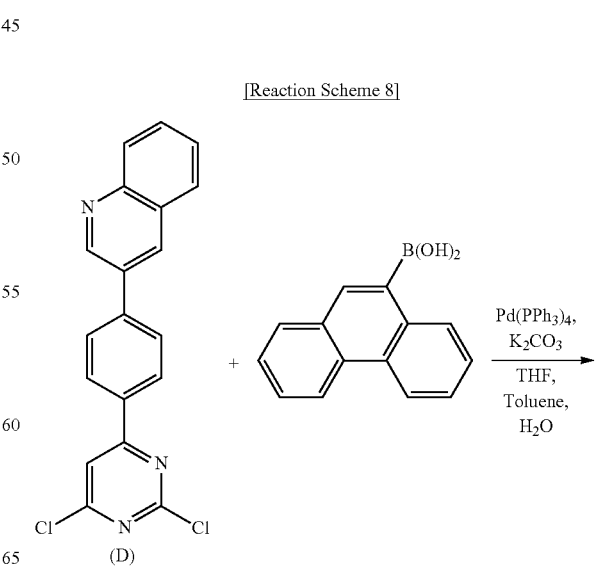

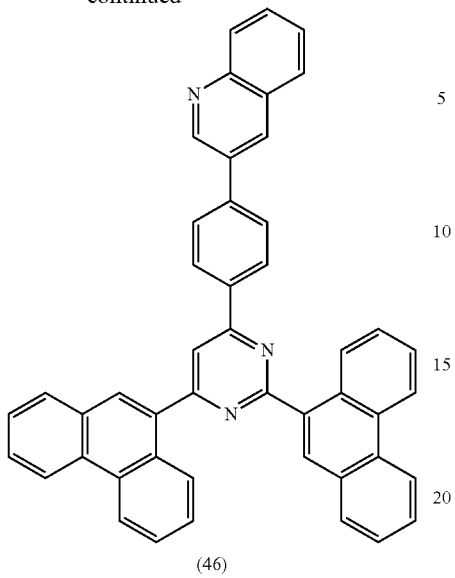

(46)

4.9 g (14 mmol) of the intermediate product (D) obtained in Example 7, 6.8 g (31 mmol) of 9-phenanthreneboronic acid, and 0.8 g (0.7 mmol) of tetrakis(triphenylphosphine)palladium were suspended in a mixed solvent of 150 ml of tetrahydrofuran and 100 ml of toluene to provide a suspension. The suspension was added to a solution in which 7.6 g (56 mmol) of potassium carbonate was dissolved in 100 ml of water. The obtained mixture was heated and refluxed for 12 hours. After separating the reaction fluid into two layers, an organic layer thereof was washed with a saturated sodium chloride aqueous solution and dried with anhydrous sodium sulfate.

The organic solvent was distilled and removed under reduced pressure, and then the residue was recrystallized with toluene. The extracted crystal was separated by filtration and washed with toluene to obtain 6.7 g (yield: 75.3%) of the compound of Chemical Formula 46.

MS[M+1]636.

Example 9

Synthesis of Chemical Formula 23 Compound

For the specific example of the compound for an organic photoelectric device, compound of the above Chemical Formula 23 was synthesized in accordance with the following Reaction Scheme 9 in two steps.

Reaction Scheme 9

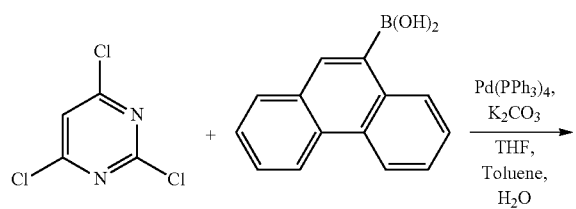

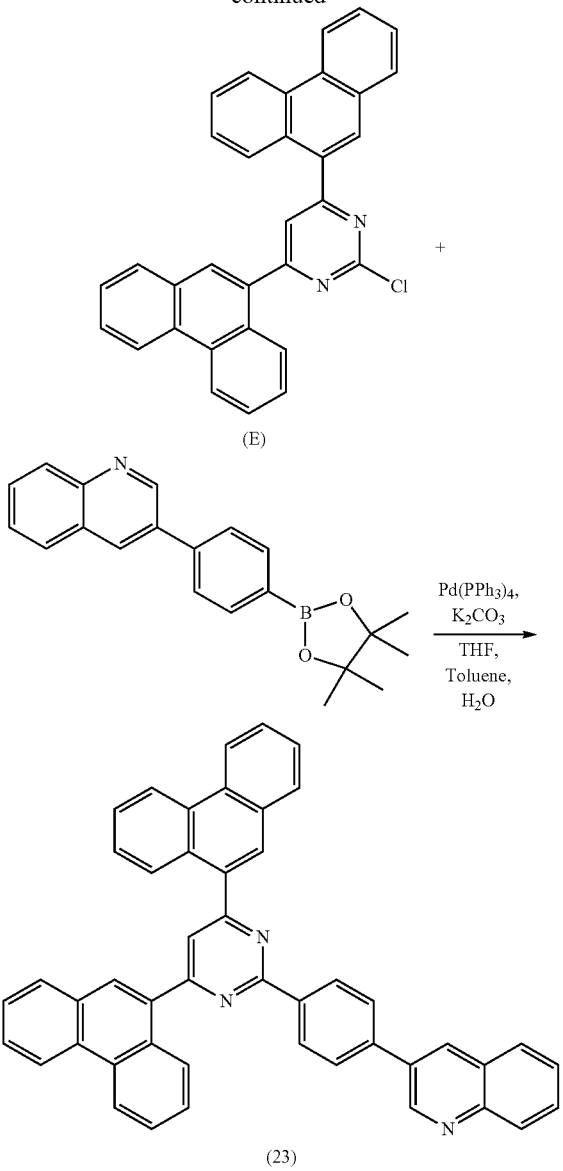

First Step; Synthesis of Intermediate Product (E)

20.0 g (109 mmol) of 2,4,6-trichloropyrimidine, 48.4 g (218 mmol) of 9-phenanthreneboronic acid, and 6.3 g (5.5 mmol) of tetrakis(triphenylphosphine)palladium were suspended in a mixed solvent of 600 ml of tetrahydrofuran and 400 ml of toluene to provide a suspension. The suspension was added to a solution in which 60.3 g (436 mmol) of potassium carbonate was dissolved in 400 ml of water, and the obtained mixture was heated and refluxed for 9 hours. After separating the reaction fluid into two layers, an organic layer thereof was washed with a saturated sodium chloride aqueous solution and dried with anhydrous sodium sulfate.

The organic solvent was distilled and removed under reduced pressure, and then the residue was recrystallized with toluene. The obtained crystal was separated by filtration and washed with toluene to obtain 35.2 g (yield: 69.1%) of intermediate product (E).

Second Step; Synthesis of Chemical Formula 23 Compound 6.5 g (14 mmol) of the intermediate product (E) obtained in the first step, 5.0 g (15 mmol) of 3-(4-(4,4,5,5-tetramethyl-1, 3,2-dioxaborolan-2-yl)phenyl)quinoline and 0.39 g (0.3 mmol) of tetrakis(triphenylphosphine)palladium were suspended in a mixed solvent of 150 ml of tetrahydrofuran and 100 ml of toluene to provide a suspension. The suspension was added to a solution in which 3.8 g (27 mmol) of potassium carbonate was dissolved in 100 ml of water, and the obtained mixture was heated and refluxed for 12 hours. After separating the reaction fluid into two layers, an organic layer thereof was washed with a saturated sodium chloride aqueous solution and dried with anhydrous sodium sulfate.

The organic solvent was distilled and removed under reduced pressure, and then the residue was recrystallized with toluene. The obtained crystal was separated by filtration and washed with toluene to obtain 7.3 g (yield: 81.5%) of the compound of Chemical Formula 23.

MS[M+1]636.

Example 10

Synthesis of Chemical Formula 52 Compound

The compound of the above Chemical Formula 52 was synthesized in accordance with the following Reaction Scheme 10 in three steps.

Reaction Scheme 10

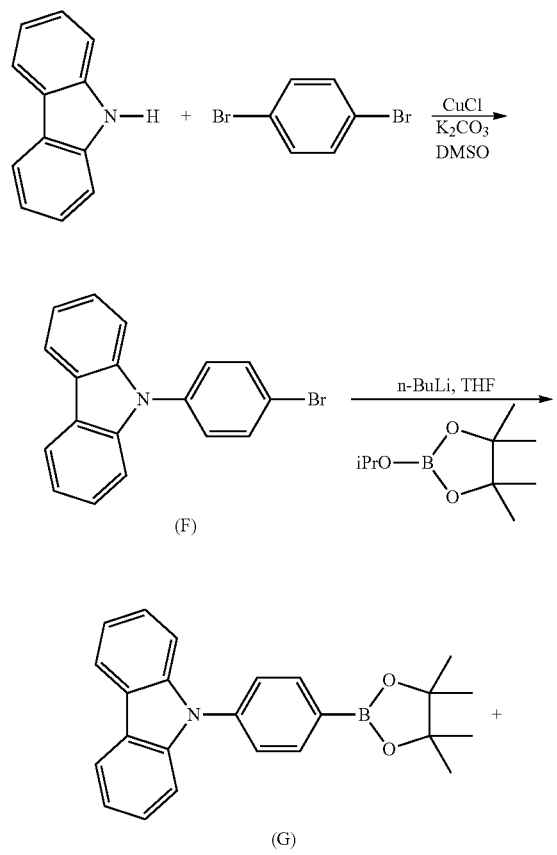

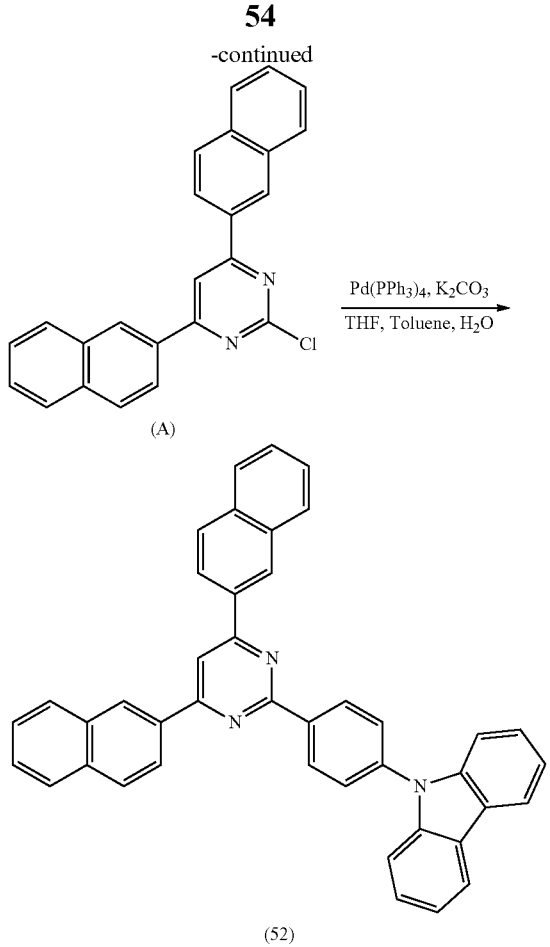

First Step; Synthesis of Intermediate Product (F)

50.8 g (304 mmol) of carbazole, 71.6 g (304 mmol) of 1,4-dibromobenzene, 3.76 g (38 mmol) of cuprous chloride, and 83.9 g (607 mmol) of potassium carbonate were suspended in 322 ml of dimethylsulfoxide, and refluxed for 8 hours under a nitrogen atmosphere. The reaction fluid was cooled to room temperature and recrystallized using methanol.

The obtained crystal was separated by filtration and the residue was purified using a silica gel column chromatography to obtain 59.9 g (yield: 61.3%) of the intermediate product (F).

Second Step; Synthesis of Intermediate Product (G)

37.8 g (117 mmol) of the intermediate product (F) was dissolved in 378 ml of tetrahydrofuran, and (1.6 M) 100.5 ml (161 mmol) of a n-butyllithium hexane solution was added at −70° C. under an argon atmosphere. The obtained solution was agitated at −70 to −40° C. for 1 hour. After the obtained reaction fluid was cooled to −70° C., 47.9 ml (235 mmol) of isopropyltetramethyldioxaborolane was added dropwise. The obtained solution was agitated at −70° C. for 1 hour, and then a temperature was increased to room temperature followed by agitating for 6 hours. 200 ml of water was added to the obtained solution, followed by agitating for 20 minutes.

After separating the reaction fluid into two layers, an organic layer was washed with a saturated sodium chloride aqueous solution and dried with anhydrous sodium sulfate.

The organic solvent was distilled and removed under reduced pressure, and then the residue was recrystallized with toluene. The obtained crystal was separated by filtration and washed with toluene to obtain 28.9 g (yield: 66.7%) of an intermediate product (G).

Third Step: Synthesis of Chemical Formula 52 Compound 4.4 g (12 mmol) of the compound (A), 5.2 g (14 mmol) of the intermediate product (G), and 0.36 g (0.3 mmol) of tetrakis(triphenylphosphine)palladium were suspended in a mixed solvent of 130 ml of tetrahydrofuran and 90 ml of toluene to provide a suspension. The suspension was added to a solution in which 3.4 g (25 mmol) of potassium carbonate was dissolved in 90 ml of water, and the obtained mixture was heated and refluxed for 12 hours. After separating the reaction fluid into two layers, an organic layer thereof was washed with a saturated sodium chloride aqueous solution and dried with anhydrous sodium sulfate.

The organic solvent was distilled and removed under reduced pressure, and then the residue was recrystallized with toluene. The obtained crystal was separated by filtration and washed with toluene to obtain 5.4 g (yield: 78.3%) of the compound of Chemical Formula 52.

MS[M+1]574.

Example 11

Synthesis of Chemical Formula 5 Compound

The compound of the above Chemical Formula 5 was synthesized in accordance with the following Reaction Scheme 11 in three steps.

Reaction Scheme 11

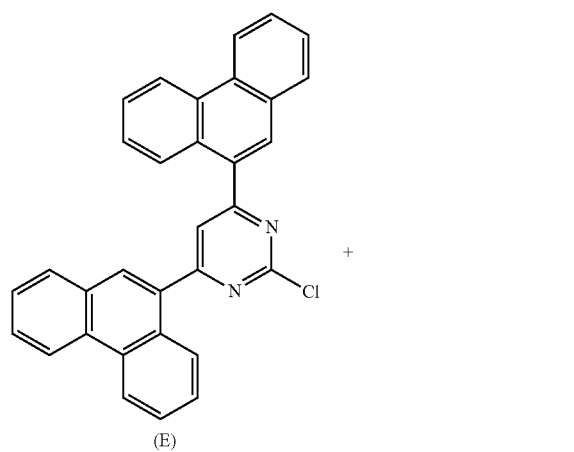

(E)

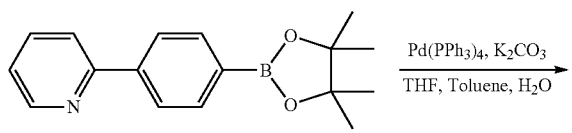

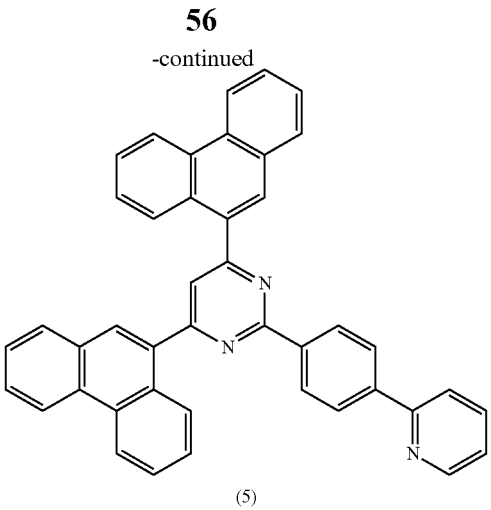

(5)

6.5 g (14 mmol) of the intermediate product (E) obtained in the first step of Example 9, 4.2 g (15 mmol) of 2-(4-(4,4,5,5-tetramethyl-1,3,2-dioxaborolan-2-yl)phenyl)pyridine, and 0.39 g (0.3 mmol) of tetrakis(triphenylphosphine)palladium were suspended in a mixed solvent of 195 ml of tetrahydrofuran and 130 ml of toluene to provide a suspension. The suspension was added to a solution in which 3.8 g (27 mmol) of potassium carbonate was dissolved in 400 ml of water, and the obtained mixture was heated and refluxed for 12 hours. After separating the reaction fluid into two layers, an organic layer thereof was washed with a saturated sodium chloride aqueous solution and dried with anhydrous sodium sulfate.

The organic solvent was distilled and removed under reduced pressure, and then the residue was recrystallized with toluene. The obtained crystal was separated by filtration and washed with toluene to obtain 5.4 g (yield: 65.3%) of the compound of Chemical Formula 5.

MS[M+1]586.

Fabricating Organic Photoelectric Device

Example 12

A 1000 Å-thick ITO layer was provided for an anode and a 1000 Å-thick aluminum (Al) layer was provided for a cathode.

A method of fabricating an organic photoelectric device is described in more detail below. A 15 Ω/cm² ITO glass substrate was prepared to have a size of 50 mm×50 mm×0.7 mm, and was cleaned in acetone, isopropyl alcohol, and pure water for 5 minutes, respectively, and then washed with UV and ozone for 30 minutes.

On the glass substrate, for a hole injection layer (HIL) $N^1,N^{1'}$-(biphenyl-4,4'-diyl)bis($N^1$-(naphthalen-2-yl)-$N^4,N^4$-diphenylbenzene-1,4-diamine) was deposited at a thickness of 65 nm. Then, for a hole transport layer (HTL), N,N'-di(1-naphthyl)-N,N'-diphenylbenzidine (NPB) was deposited at a thickness of 40 nm.

For an emission layer, 5 wt % N,N,N',N'-tetrakis(3,4-dimethylphenyl)chrysene-6,12-diamine (fluorescent blue dopant) and 95 wt % of 9-(3-(naphthalen-1-yl)phenyl)-10-(naphthalen-2-yl)anthracene (fluorescent blue host) were deposited at a thickness of 25 nm.

For an electron transport layer (ETL), the compound of Chemical Formula 4 obtained in Example 1 was deposited at a thickness of 35 nm.

On the electron transport layer (ETL), for an electron injection layer (EIL), Liq was vacuum-deposited at a thickness of 0.5 nm, and Al was vacuum-deposited at a thickness of 100 nm to provide a Liq/Al electrode. The structure of the obtained organic photoelectric device is shown in FIG. 5.

Example 13

An organic photoelectric device was fabricated in accordance with the same procedure as in Example 12, except that, for an electron transport layer (ETL), the compound of Chemical Formula 22 in Example 4 was used instead of the compound of Chemical Formula 4 in Example 1.

Example 14

An organic photoelectric device was fabricated in accordance with the same procedure as in Example 12, except that, for an electron transport layer (ETL), the compound of Chemical Formula 28 in Example 5 was used instead of the compound of Chemical Formula 4 in Example 1.

Example 15

An organic photoelectric device was fabricated in accordance with the same procedure as in Example 12, except that, for an electron transport layer (ETL), the compound of Chemical Formula 45 in Example 7 was used instead of the compound of Chemical Formula 4 in Example 1.

Example 16

An organic photoelectric device was fabricated in accordance with the same procedure as in Example 12, except that, for an electron transport layer (ETL), the compound of Chemical Formula 46 in Example 8 was used instead of the compound of Chemical Formula 4 in Example 1.

Example 17

An organic photoelectric device was fabricated in accordance with the same procedure as in Example 12, except that, for an electron transport layer (ETL), the compound of Chemical Formula 23 in Example 9 was used instead of the compound of Chemical Formula 4 in Example 1.

Example 18

An organic photoelectric device was fabricated in accordance with the same procedure as in Example 12, except that, for an electron transport layer (ETL), the compound of Chemical Formula 5 in Example 11 was used instead of the compound of Chemical Formula 4 in Example 1.

Comparative Example 1

An organic photoelectric device was fabricated in accordance with the same procedure as in Example 12, except that, for an electron transport layer (ETL), the compound $Alq_3$ (35 nm) represented by the following Chemical Formula 59 was used instead of the compound of Chemical Formula 4 in Example 1.

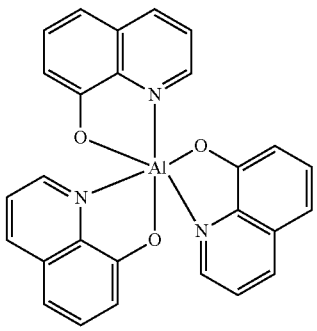

[Chemical Formula 59]

Experimental Examples

Performance Measurement of the Organic Photoelectric Device

Each organic photoelectric device according to Examples 12 to 18 and Comparative Example 1 was measured regarding luminous efficiency according to a voltage. The measurement method is as follows.

1) Measurement of Current Density Change Depending on Voltage Change

The fabricated organic photoelectric devices according to Examples 12 to 18 and Comparative Example 1 were increased in voltage from 0 V to 14 V and measured regarding a current value in a unit device by using a current-voltage device (Keithley 2400®). Then, current densities were measured by dividing the current values by areas.

2) Measurement of Luminance Change Depending on Voltage Change

The organic photoelectric devices according to Examples 12 to 18 and Comparative Example 1 were increased in voltage from 0 V to 14 V and measured regarding luminance using a luminance meter (Minolta Cs-1000A).

3) Measurement of Electric Power Efficiency

Electric power efficiency was calculated from the current density and the luminance measured from the "1) Measurement of current density change depending on voltage change" and "2) Measurement of luminance change depending on voltage change", and voltage (V). The results are shown in the following Table 1.

TABLE 1

| | Luminance 1000 $cd/m^2$ | | | | |
|---|---|---|---|---|---|
| | Driving voltage | Current efficiency | Electric power efficiency | Color coordinate CIE | |
| | (V) | (cd/W) | (lm/W) | x | y |
| Example 12 | 5.2 | 11.10 | 6.70 | 0.15 | 0.23 |
| Example 13 | 6.0 | 9.3 | 4.85 | 0.15 | 0.23 |
| Example 14 | 6.6 | 8.5 | 4.04 | 0.15 | 0.23 |
| Example 15 | 6.4 | 7.2 | 3.55 | 0.15 | 0.23 |
| Example 16 | 7.2 | 8.6 | 3.75 | 0.15 | 0.23 |
| Example 17 | 7.7 | 8.0 | 3.27 | 0.15 | 0.23 |
| Example 18 | 5.2 | 12.0 | 7.35 | 0.15 | 0.23 |
| Comparative Example 1 | 7.3 | 6.84 | 2.94 | 0.15 | 0.23 |

Referring to Table 1, it may be seen that the organic photoelectric devices according to Examples 12-18 (in which the electron transport layer was formed with the material for an organic photoelectric device according to an embodiment) exhibited excellent efficiency performance together with a low driving voltage, compared to the case of using the electron transport layer of $Alq_3$ according to Comparative Example 1. Accordingly, the organic compound according to an embodiment exhibited high thermal stability, a low driving voltage, and high luminous efficiency as shown in the performance result of the organic photoelectric device. Thus, it is anticipated that the organic compound may improve the life-span of an organic photoelectric device. Without being bound by theory is believed that the aryl substituent may improve electrochemical and thermal stability, resulting in improvement of life-span of the device.

By way of summation and review, in order to implement the above excellent performance of an organic light emitting diode, a material constituting an organic material layer, e.g., a hole injection material, a hole transport material, a light emitting material, an electron transport material, an electron injection material, and a light emitting material such as a host and/or a dopant should be stable and have good efficiency. Such a material may also be useful for other organic photoelectric devices.

Embodiments provide a compound for an organic photoelectric device having excellent life-span, efficiency, electrochemical stability, and thermal stability due to excellent electron transport capability and thermal stability characteristics of the compound.

The embodiments provide a compound for an organic photoelectric device that can act as a light emitting material or an electron injection and/or transport material, and also as a light emitting host along with an appropriate dopant.

The embodiments also provide an organic photoelectric device including the compound, the device exhibiting improved life-span, efficiency, driving voltage, electrochemical stability, and thermal stability.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic photoelectric device, the compound being represented by the following Chemical Formula 1:

[Chemical Formula 1]

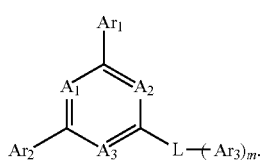

wherein in the above Chemical Formula 1, $A_1$ to $A_3$ are each independently carbon or nitrogen, provided that at least two of $A_1$ to $A_3$ are nitrogen, $Ar_1$ and $Ar_2$ are each independently a substituted or unsubstituted C6 to C30 aryl, $Ar_3$ is a substituted or unsubstituted imidazole, a substituted or unsubstituted thiazolyl, a substituted or unsubstituted oxazolyl, a substituted or unsubstituted oxadiazolyl, a substituted or unsubstituted triazolyl, a substituted or unsubstituted pyridinyl, a substituted or unsubstituted quinolinyl, a substituted or unsubstituted isoquinolinyl, a substituted or unsubstituted acridinyl, a substituted or unsubstituted imidazopyridinyl, a substituted or unsubstituted imidazopyrimidinyl, or a combination thereof, L is an unsubstituted phenylene, a substituted or unsubstituted naphthalene, or a substituted or unsubstituted anthracene, provided that when L is an unsubstituted phenylene, the ring including $A_1$ to $A_3$ is linked to the para position of L with respect to $Ar_3$, m is an integer of 1 to 3, and a moiety of Chemical Formula 1 that includes L and $Ar_3$ is different from $Ar_1$ or $Ar_2$.

2. The compound as claimed in claim 1, wherein $Ar_1$ and $Ar_2$ are each independently a phenyl, a naphthyl, an anthracenyl, a phenanthrenyl, a pyrenyl, a perylenyl, a chrysenyl, or a combination thereof.

3. The compound as claimed in claim 1, wherein at least one of $Ar_1$ and $Ar_2$ include a substituent, the substituent including a C1 to C30 alkyl, a C1 to C10 alkylsilyl, a C3 to C30 cycloalkyl, a C6 to C30 aryl, a C1 to C10 alkoxy, a fluoro, a trifluoroalkyl, a cyano, or a combination thereof.

4. The compound as claimed in claim 1, wherein L is an unsubstituted phenylene.

5. The compound as claimed in claim 1, wherein the compound represented by Chemical Formula 1 is represented by at least one of the following Chemical Formulae 2 to 10:

[Chemical Formula 2]

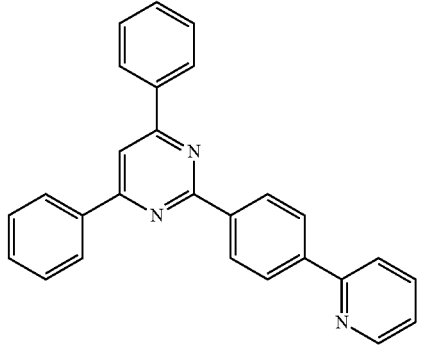

[Chemical Formula 3]

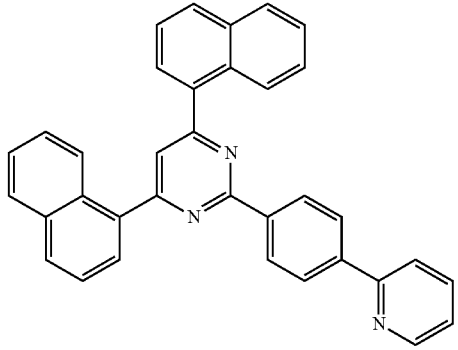

[Chemical Formula 4]
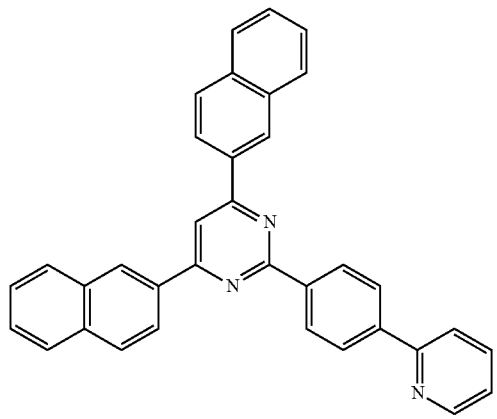
[Chemical Formula 5]
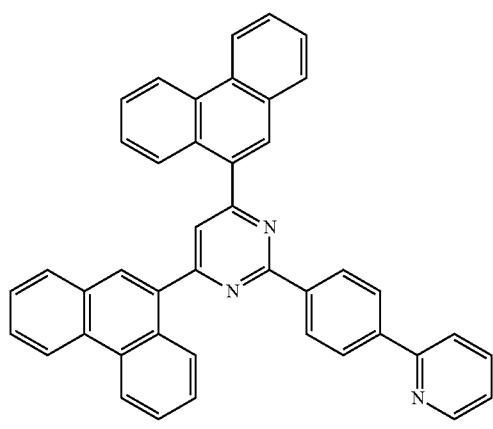
[Chemical Formula 6]
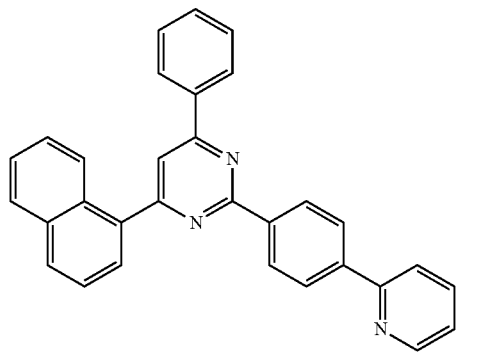
[Chemical Formula 7]
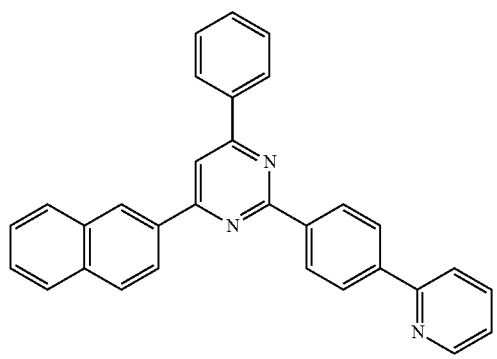
[Chemical Formula 8]
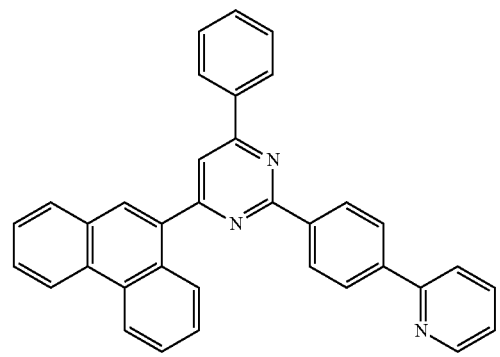
[Chemical Formula 9]
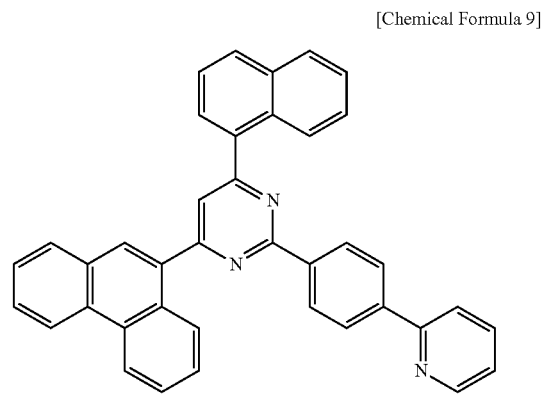
[Chemical Formula 10]
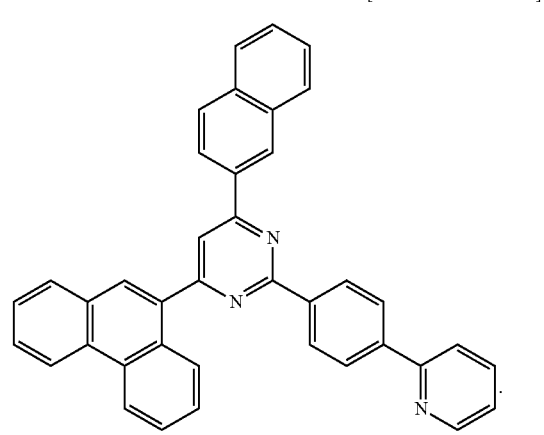
6. The compound as claimed in claim 1, wherein the compound represented by Chemical Formula 1 is represented by at least one of the following Chemical Formulae 11 to 19:

[Chemical Formula 11]
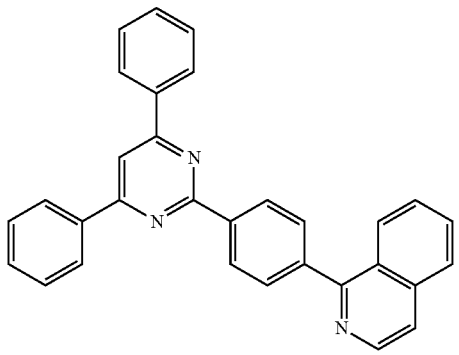
[Chemical Formula 12]
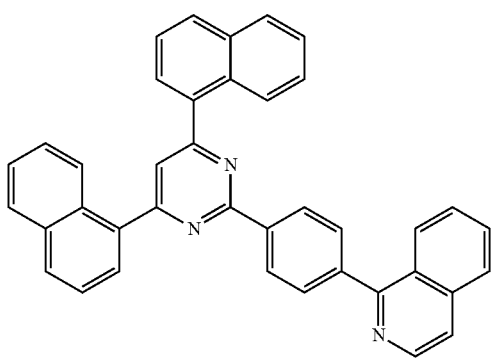
[Chemical Formula 13]
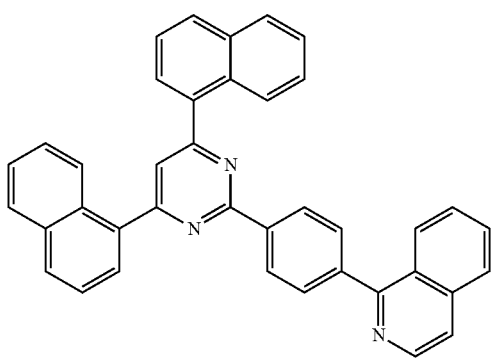
[Chemical Formula 14]
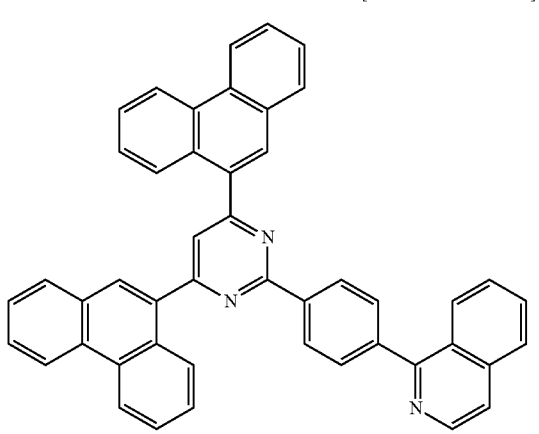
[Chemical Formula 15]
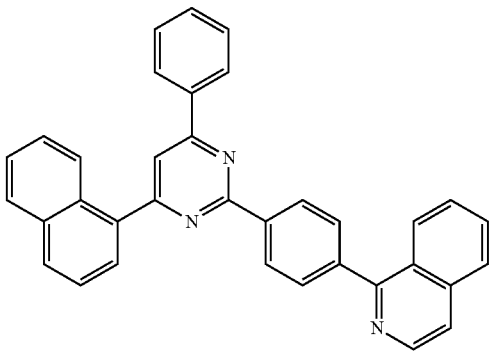
[Chemical Formula 16]
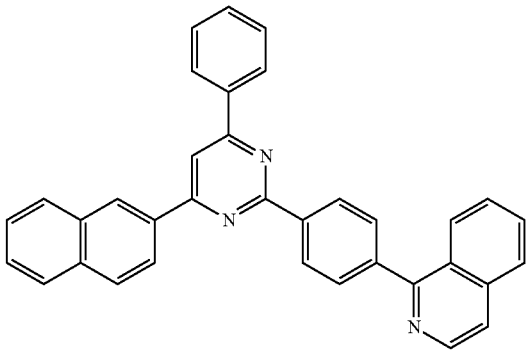
[Chemical Formula 17]
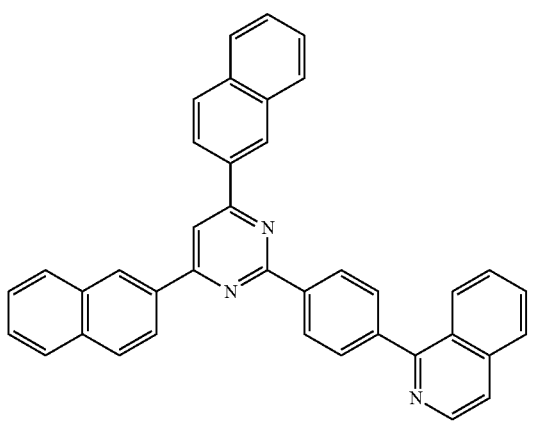
[Chemical Formula 18]
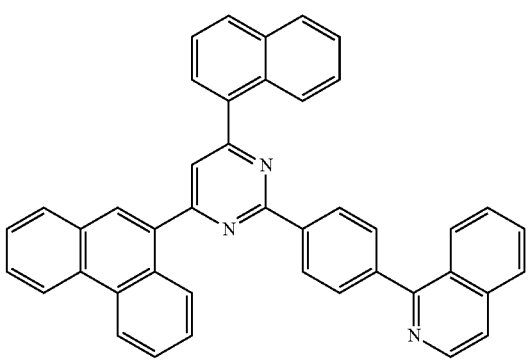

[Chemical Formula 19]
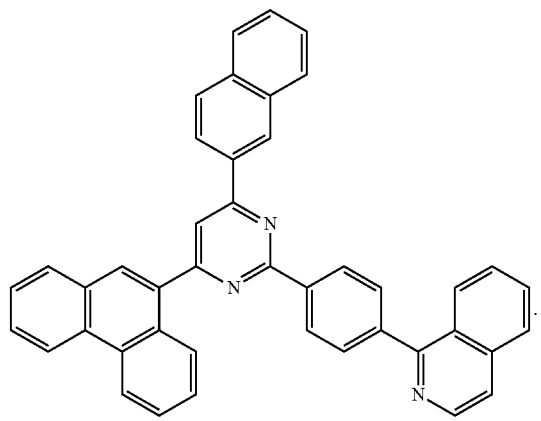
7. The compound as claimed in claim 1, wherein the compound represented by Chemical Formula 1 is represented by at least one of the following Chemical Formulae 20 to 28:
[Chemical Formula 20]
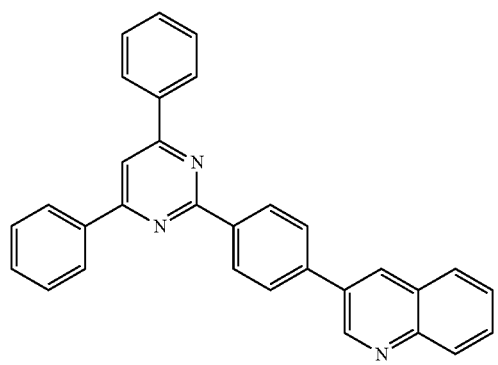
[Chemical Formula 21]
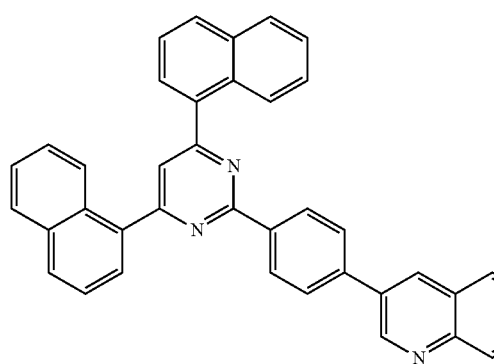
[Chemical Formula 22]
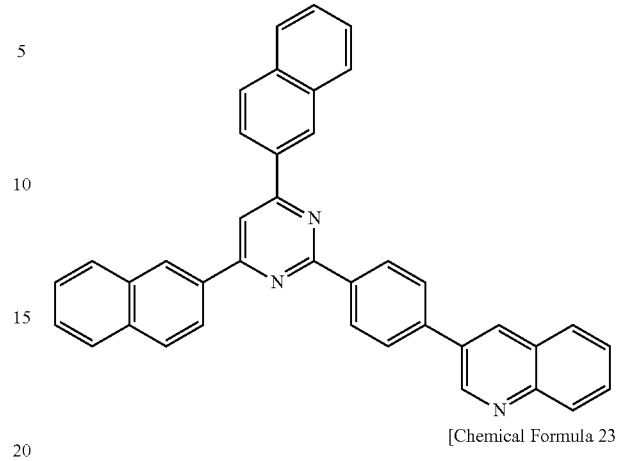
[Chemical Formula 23]
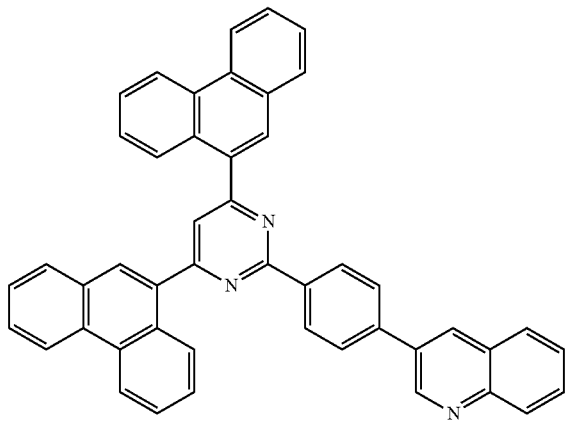
[Chemical Formula 24]
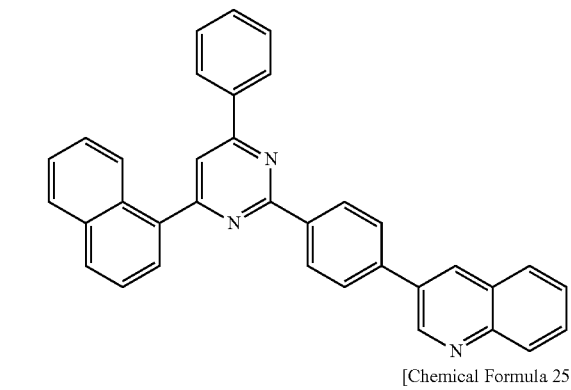
[Chemical Formula 25]
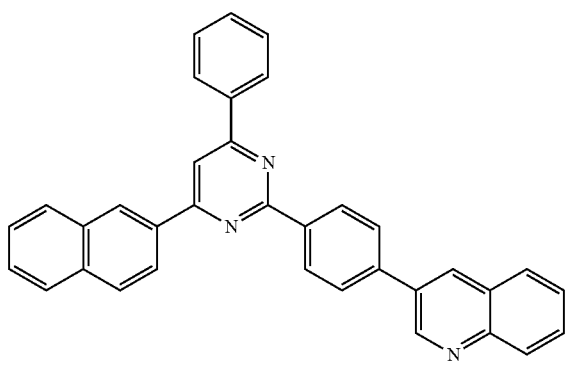

[Chemical Formula 26]
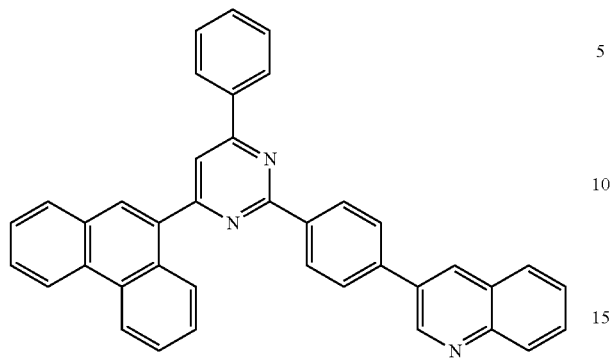
[Chemical Formula 27]
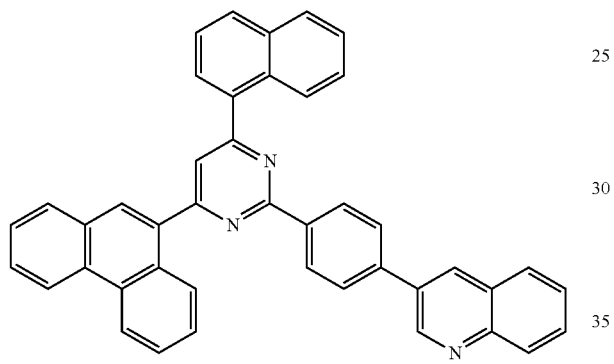
[Chemical Formula 28]
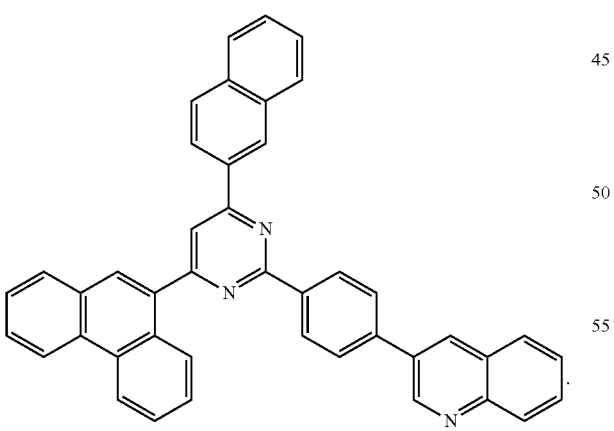
[Chemical Formula 29]
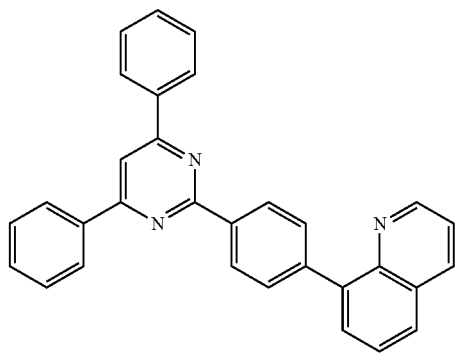
[Chemical Formula 30]
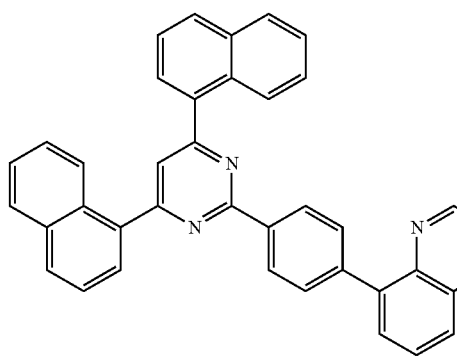
[Chemical Formula 31]
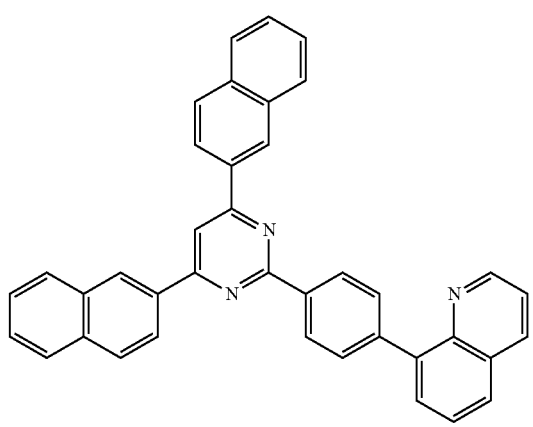
[Chemcial Formula 32]
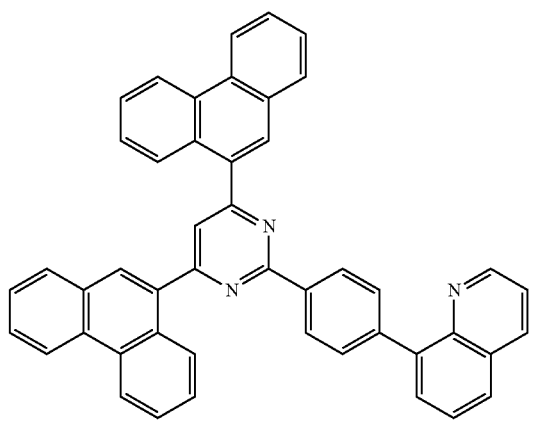
8. The compound as claimed in claim 1, wherein the compound represented by Chemical Formula 1 is represented by at least one of the following Chemical Formulae 29 to 37:

[Chemical Formula 33]
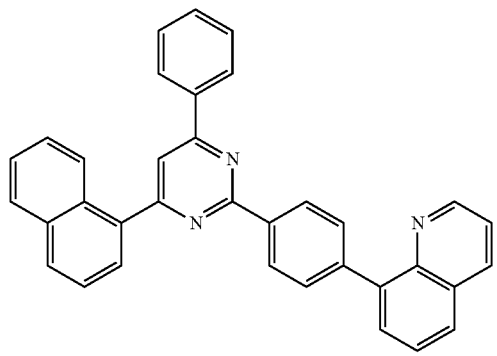
[Chemical Formula 34]
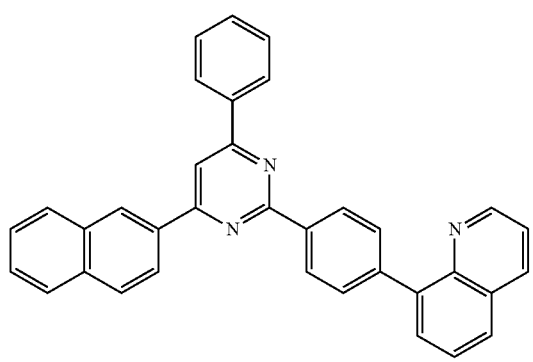
[Chemical Formula 35]
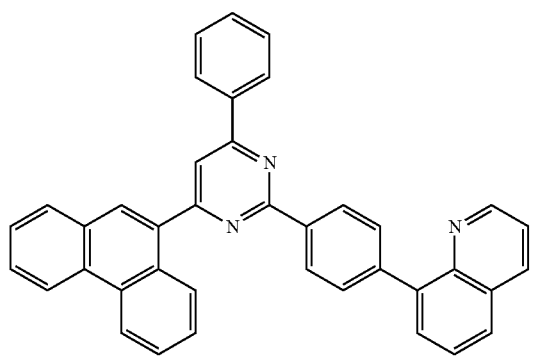
[Chemical Formula 36]
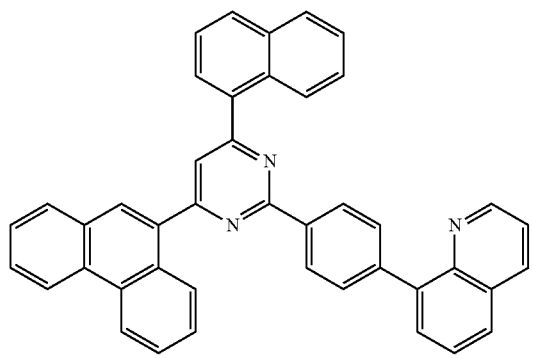
[Chemical Formula 37]
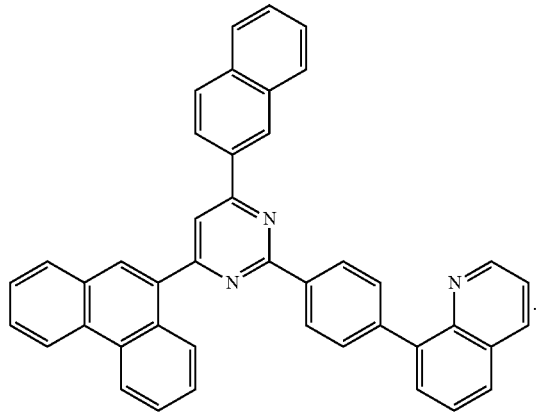
9. The compound as claimed in claim 1, wherein the compound represented by Chemical Formula 1 is represented by at least one of the following Chemical Formulae 38 to 46:
[Chemical Formula 38]
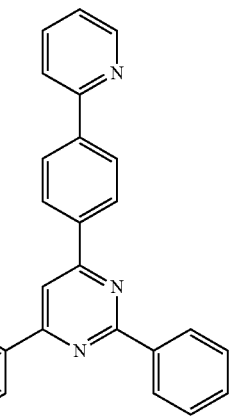
[Chemical Formula 39]
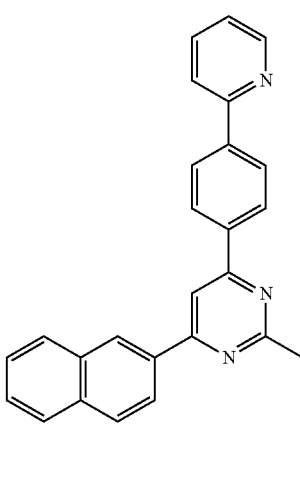

[Chemical Formula 40]
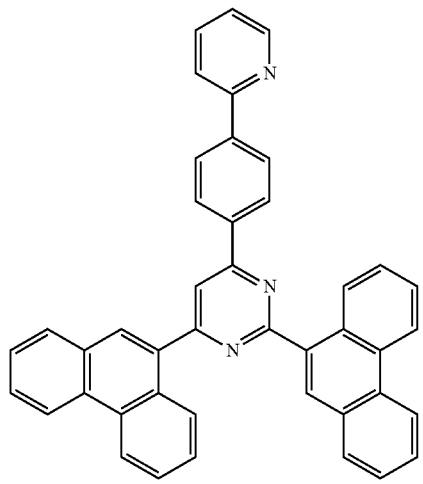
[Chemical Formula 41]
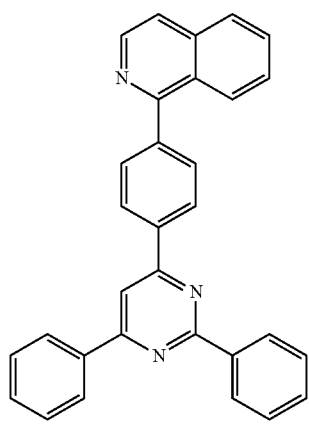
[Chemical Formula 42]
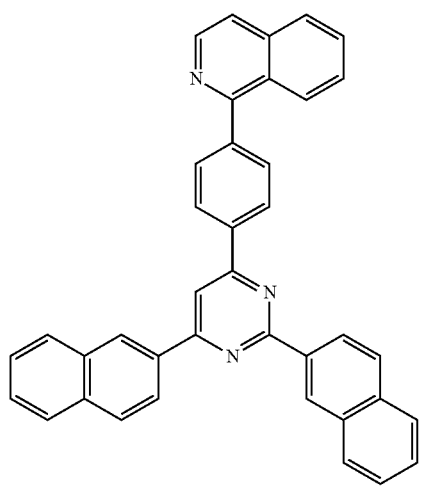
[Chemical Formula 43]
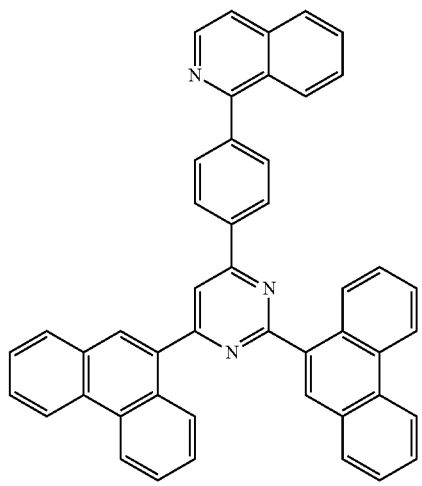
[Chemical Formula 44]
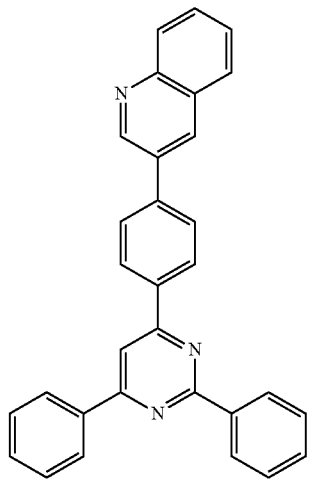
[Chemical Formula 45]
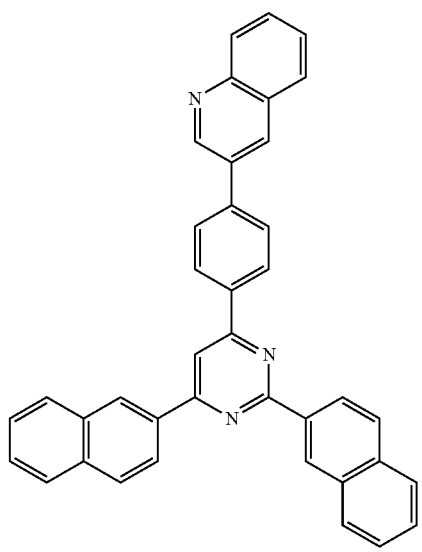

-continued

[Chemical Formula 46]

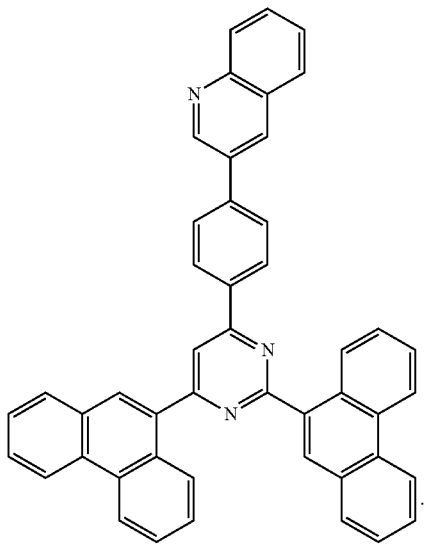

10. The compound as claimed in claim 1, wherein the compound represented by Chemical Formula 1 is represented by at least one of the following Chemical Formulae 47 to 49:

[Chemical Formula 47]

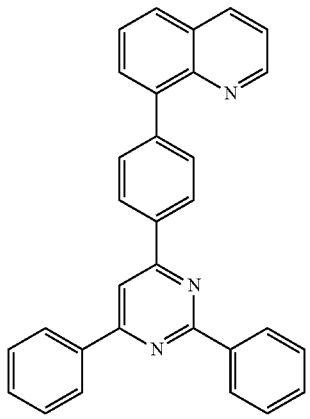

[Chemical Formula 48]

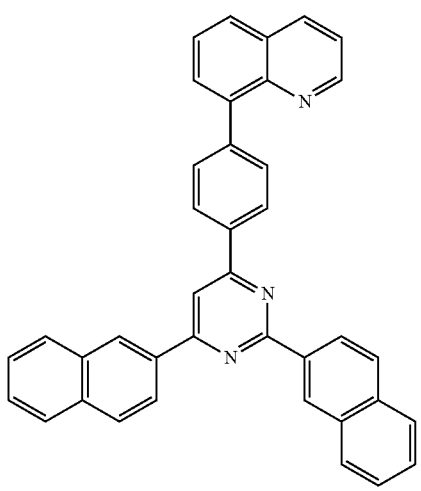

-continued

[Chemical Formula 49]

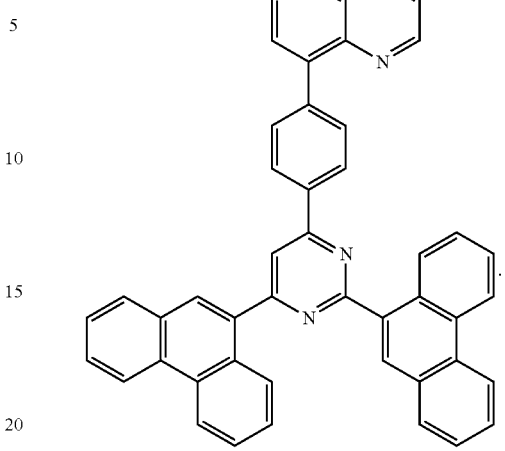

11. An organic photoelectric device, comprising:
an anode;
a cathode; and
at least one organic thin layer between the anode and cathode, wherein the at least one the organic thin layer includes the compound as claimed in claim 1.

12. The organic photoelectric device as claimed in claim 11, wherein the at least one organic thin layer includes an emission layer, a hole transport layer (HTL), a hole injection layer (HIL), an electron injection layer (EIL), a hole blocking layer, or a combination thereof.

13. The organic photoelectric device as claimed in claim 11, wherein the compound is included in an electron transport layer (ETL) or an electron injection layer (EIL) of the at least one organic thin layer.

14. The organic photoelectric device as claimed in claim 11, wherein the compound is included in an emission layer of the at least one organic thin layer.

15. The organic photoelectric device as claimed in claim 11, wherein the compound is a phosphorescent or fluorescent host in an emission layer of the at least one organic thin layer.

16. The organic photoelectric device as claimed in claim 11, wherein the compound is a fluorescent blue dopant in an emission layer of the at least one organic thin layer.

17. The organic photoelectric device as claimed in claim 11, wherein the organic photoelectric device is one of an organic light emitting diode, an organic solar cell, an organic transistor, an organic photo-conductor drum, and an organic memory device.

18. A display device comprising the organic photoelectric device as claimed in claim 11.

19. The compound as claimed in claim 1, wherein $Ar_3$ is an unsubstituted imidazole, unsubstituted thiazolyl, unsubstituted oxazolyl, unsubstituted oxadiazolyl, unsubstituted triazolyl, unsubstituted pyridinyl, unsubstituted quinolinyl, unsubstituted isoquinolinyl, unsubstituted acridinyl, unsubstituted imidazopyridinyl, unsubstituted imidazopyrimidinyl, or a combination thereof.

20. The compound as claimed in claim 1, wherein $Ar_3$ is imidazole, thiazolyl, oxazolyl, oxadiazolyl, triazolyl, pyridinyl, quinolinyl, isoquinolinyl, acridinyl, imidazopyridinyl, imidazopyrimidinyl, or a combination thereof, and
wherein $Ar_3$ is substituted with a C1 to C30 alkyl, a C1 to C10 alkylsilyl, a C3 to C30 cycloalkyl, a C1 to C30 alkoxy, a fluoro, a cyano, or a combination thereof.

21. A compound for an organic photoelectric device, the compound being represented by one of the following Chemical Formulae 2 to 49:
[Chemical Formula 2]
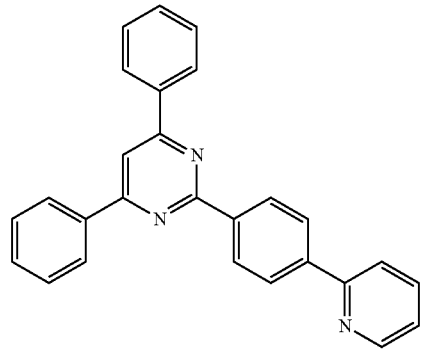
[Chemical Formula 3]
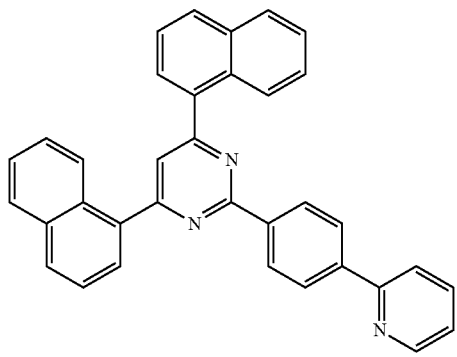
[Chemical Formula 4]
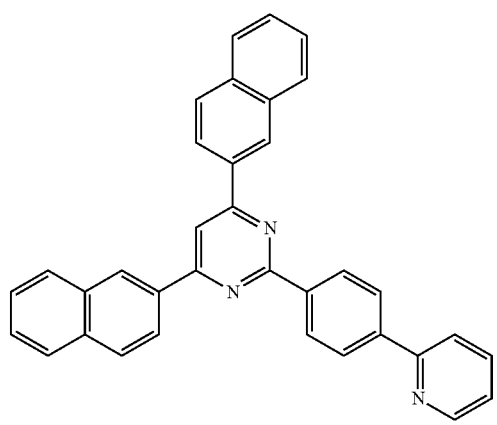
[Chemical Formula 5]
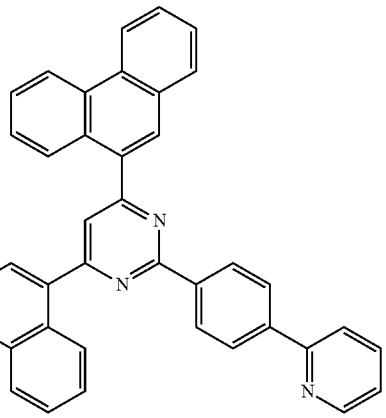
[Chemical Formula 6]
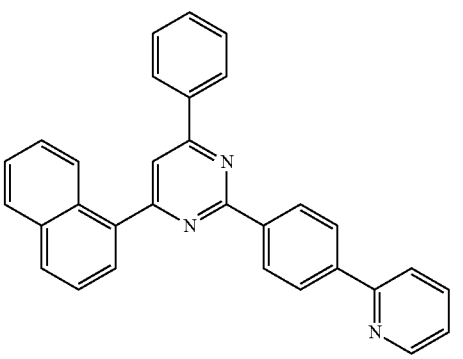
[Chemical Formula 7]
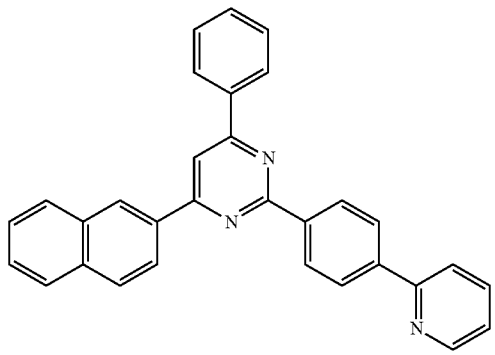
[Chemical Formula 8]
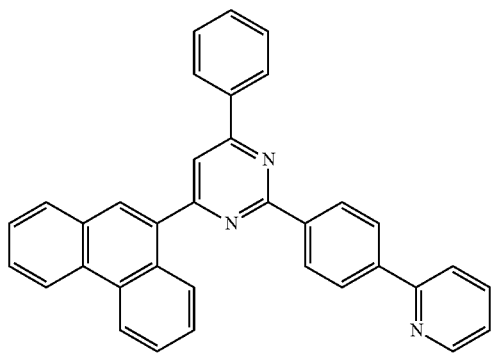

[Chemical Formula 9]
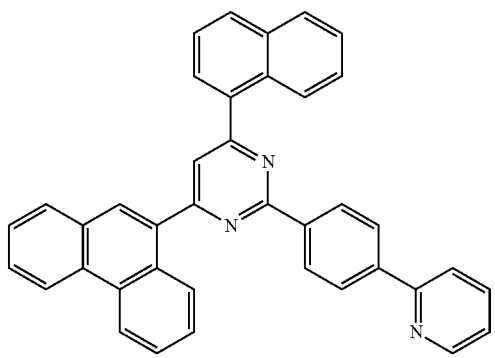
[Chemical Formula 10]
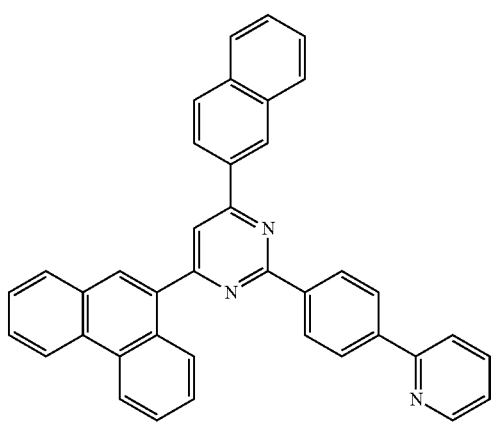
[Chemical Formula 11]
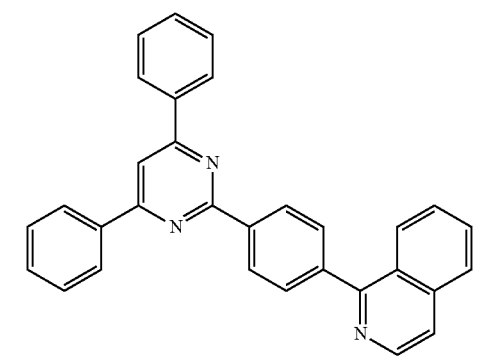
[Chemical Formula 12]
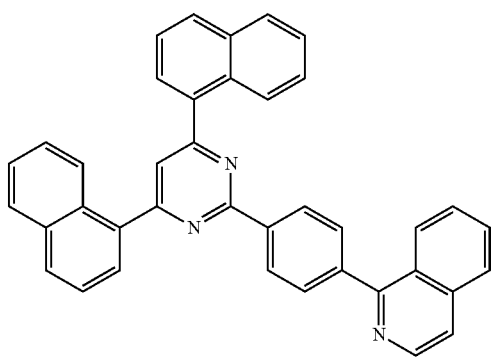
[Chemical Formula 13]
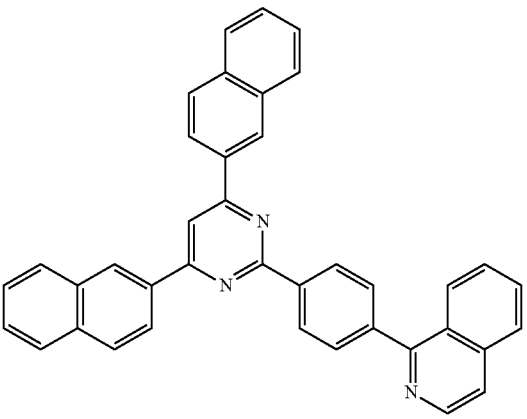
[Chemical Formula 14]
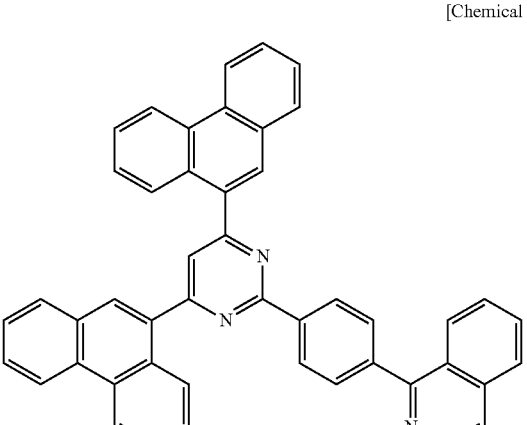
[Chemical Formula 15]
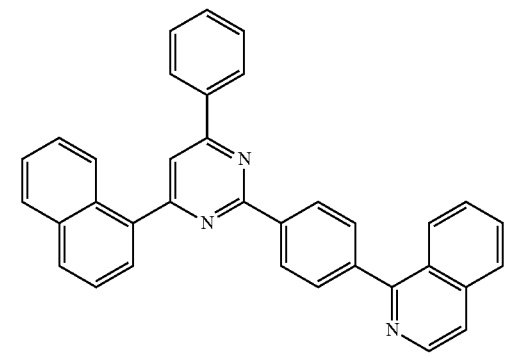
[Chemical Formula 16]
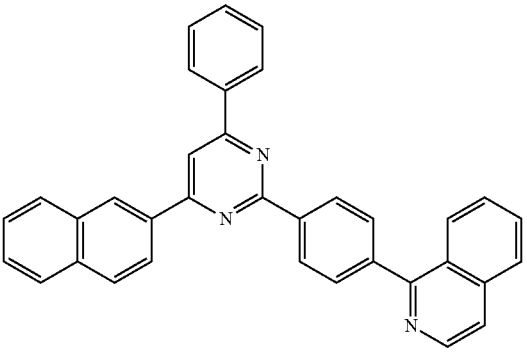

[Chemical 17]

[Chemical Formula 18]

[Chemical Formula 19]

[Chemical Formula 20]

[Chemical Formula 21]

[Chemical Formula 22]

[Chemical Formula 23]

[Chemical Formula 24]

[Chemical Formula 25]
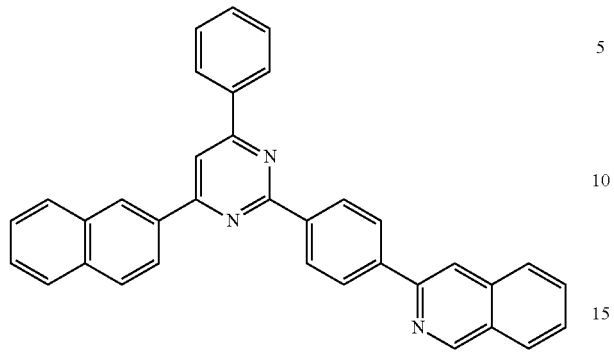
[Chemical Formula 26]
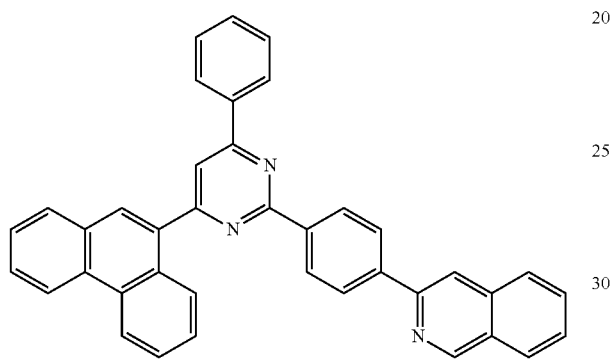
[Chemical Formula 27]
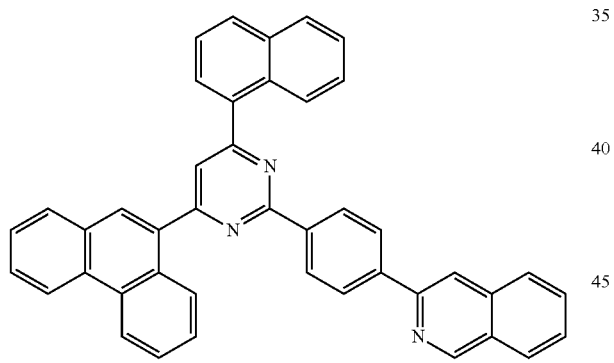
[Chemical Formula 28]
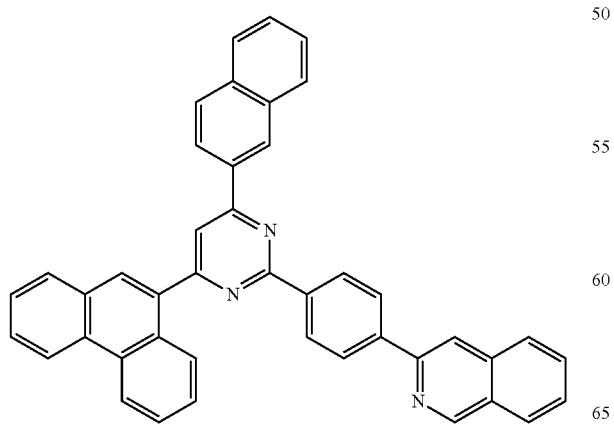
[Chemical Formula 29]
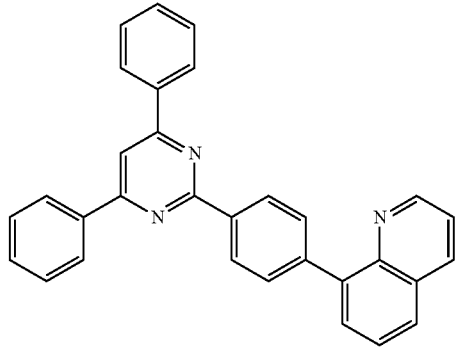
[Chemical Formula 30]
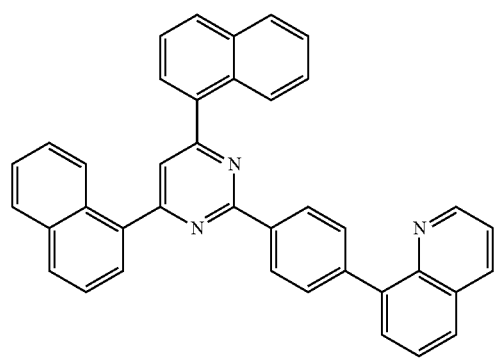
[Chemical Formula 31]
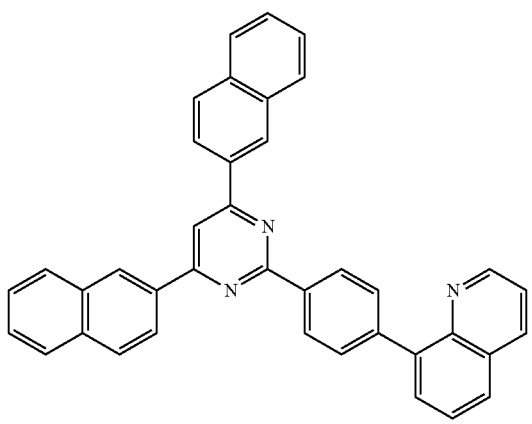
[Chemical Formula 32]
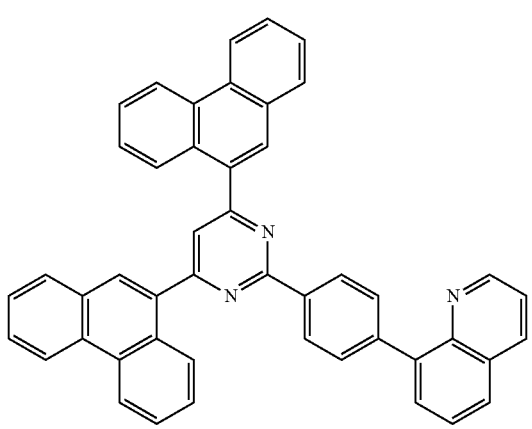

[Chemical Formula 33]
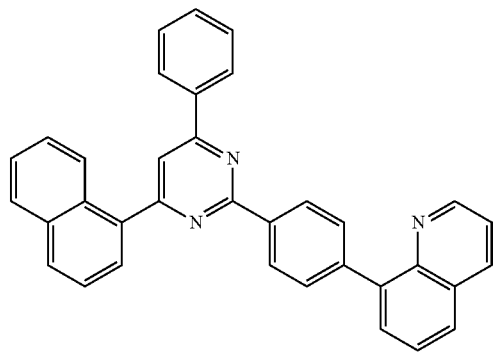
[Chemical Formula 34]
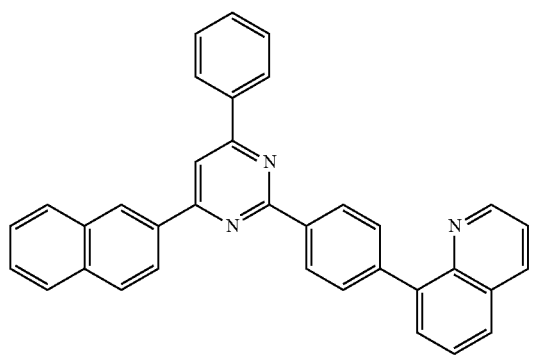
[Chemical Formula 35]
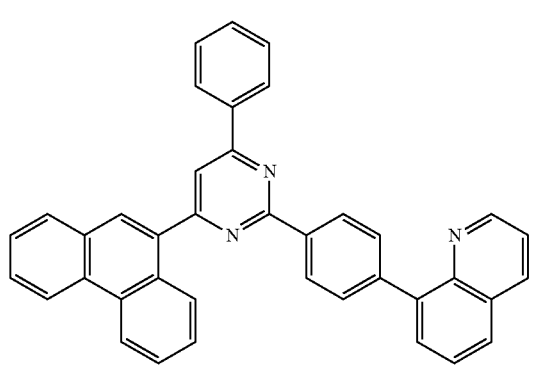
[Chemical Formula 36]
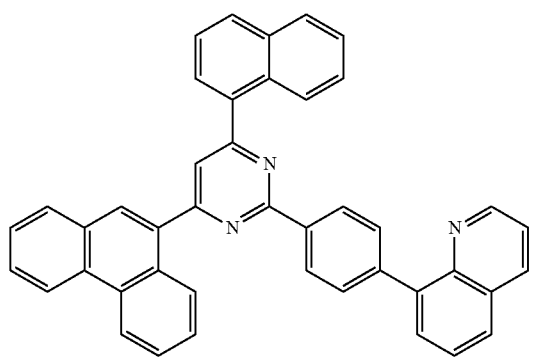
[Chemical Formula 37]
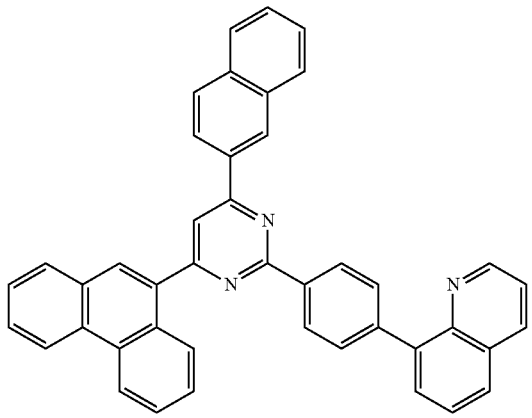
[Chemical Formula 38]
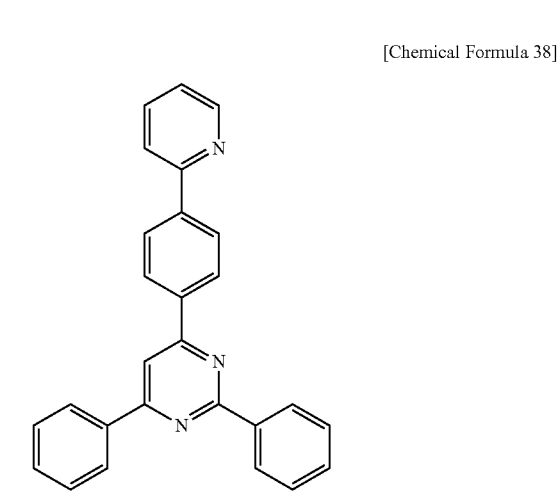
[Chemical Formula 39]
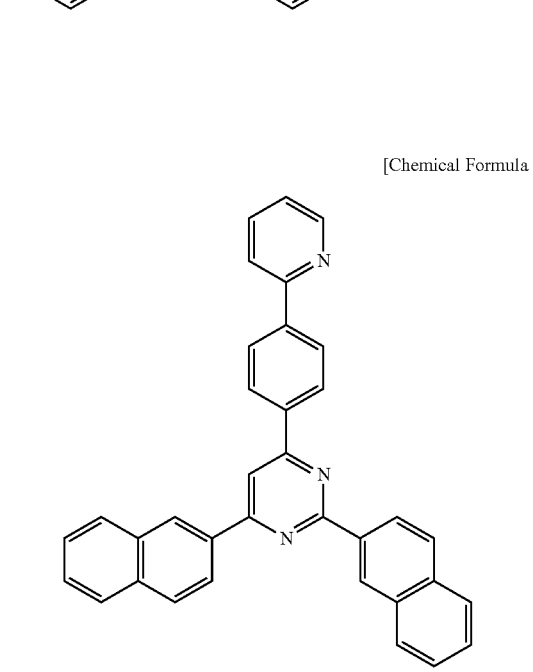

[Chemical Formula 40]
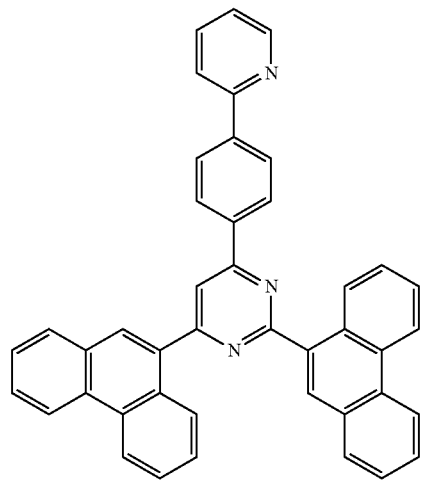
[Chemical Formula 41]
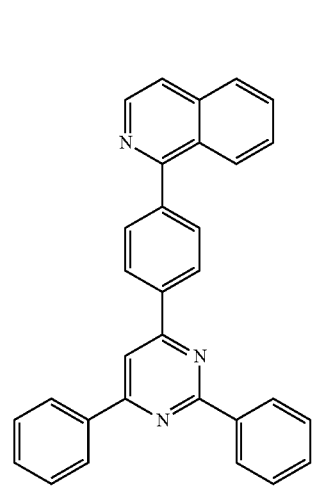
[Chemical Formula 42]
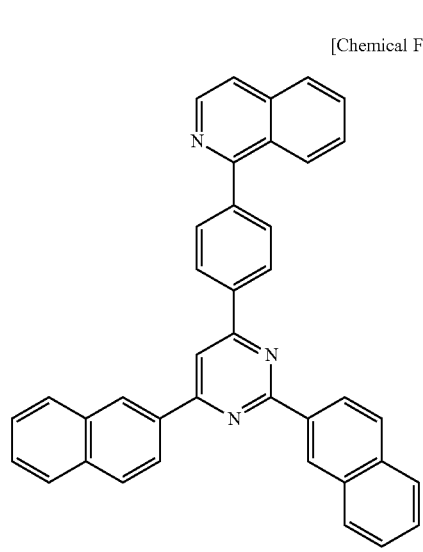
[Chemical Formula 43]
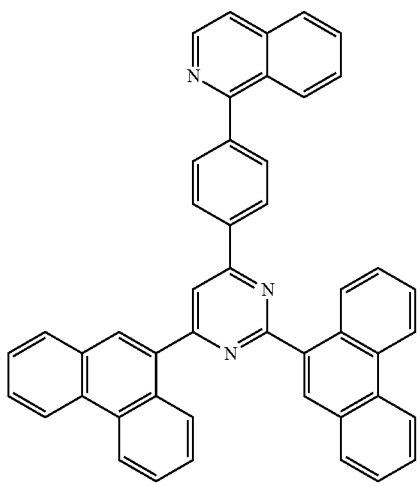
[Chemical Formula 44]
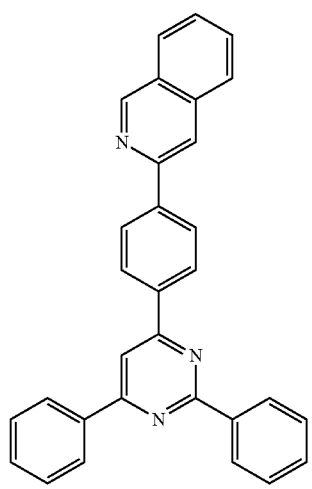
[Chemical Formula 45]
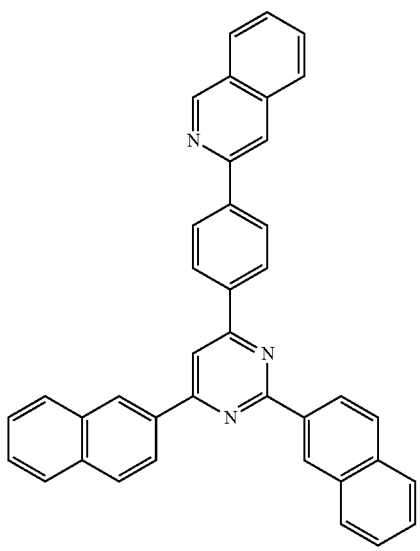

[Chemical Formula 46]
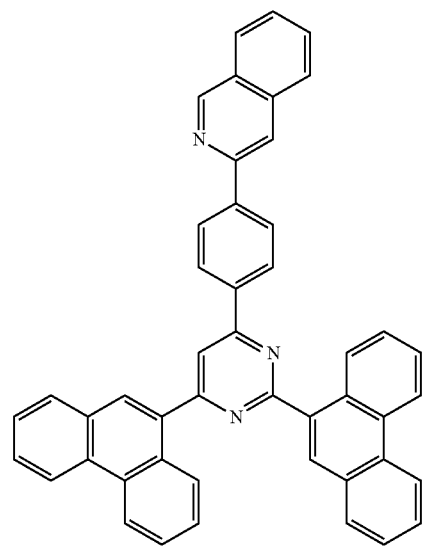
[Chemical Formula 47]
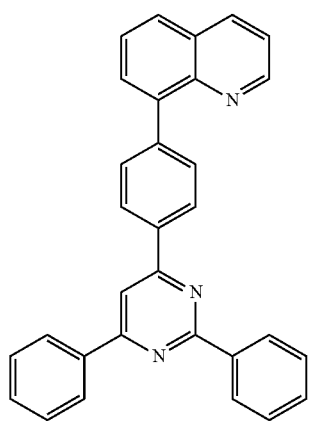
[Chemical Formula 48]
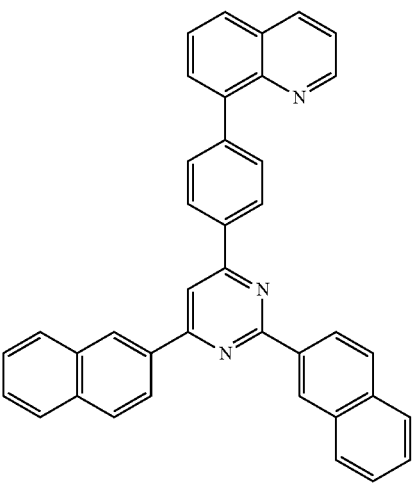
[Chemical Formula 49]
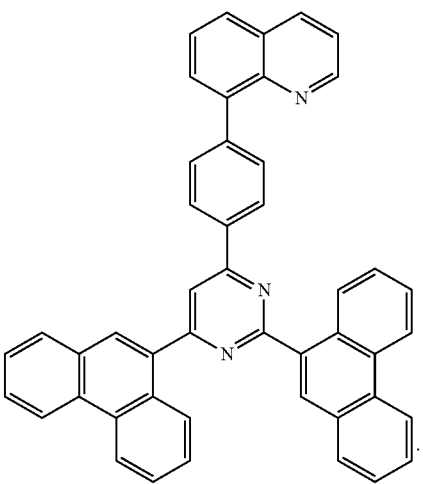
* * * * *